US011795509B2

(12) United States Patent
Li et al.

(10) Patent No.: US 11,795,509 B2
(45) Date of Patent: Oct. 24, 2023

(54) SCREENING KIT FOR PAROXYSMAL SUPRAVENTRICULAR TACHYCARDIA

(71) Applicants: SICHUAN PROVINCIAL PEOPLE'S HOSPITAL, Sichuan (CN); CHENGDU MEDICAL COLLEGE, Sichuan (CN); NANJING YSY BIOTECH COMPANY LTD., Jiangsu (CN)

(72) Inventors: Xiaoping Li, Sichuan (CN); Rong Luo, Sichuan (CN); Qingshun Zhao, Sichuan (CN); Zhenglin Yang, Sichuan (CN); Tao He, Sichuan (CN); Mingjiang Liu, Sichuan (CN)

(73) Assignees: SICHUAN PROVINCIAL PEOPLE'S HOSPITAL, Sichuan (CN); CHENGDU MEDICAL COLLEGE, Sichuan (CN); NANJING YSY BIOTECH COMPANY LTD., Jiangsu (CN)

( * ) Notice: Subject to any disclaimer, the term of this patent is extended or adjusted under 35 U.S.C. 154(b) by 0 days.

(21) Appl. No.: 17/757,911

(22) PCT Filed: Sep. 10, 2020

(86) PCT No.: PCT/CN2020/114405
§ 371 (c)(1),
(2) Date: Jun. 23, 2022

(87) PCT Pub. No.: WO2021/128950
PCT Pub. Date: Jul. 1, 2021

(65) Prior Publication Data

US 2023/0057598 A1 Feb. 23, 2023

(30) Foreign Application Priority Data

Dec. 23, 2019 (CN) ........................ 201911341609.4

(51) Int. Cl.
*C12Q 1/68* (2018.01)
*C12P 19/34* (2006.01)
*C12Q 1/6883* (2018.01)
*C12Q 1/6869* (2018.01)

(52) U.S. Cl.
CPC ......... *C12Q 1/6883* (2013.01); *C12Q 1/6869* (2013.01); *C12Q 2600/156* (2013.01)

(58) Field of Classification Search
CPC ........... G01N 33/5041; G01N 33/5044; C12Q 1/6883
See application file for complete search history.

(56) References Cited

U.S. PATENT DOCUMENTS

2004/0081988 A1 4/2004 Johnson et al.
2016/0281166 A1 9/2016 Bhattacharjee et al.

FOREIGN PATENT DOCUMENTS

CN 109652533 A 4/2019
CN 109750099 A 5/2019
CN 110982891 A 4/2020
KR 101767644 B1 8/2017
WO 2015185924 A1 12/2015

OTHER PUBLICATIONS

Thermo Scientific Prodcut Informtation—BsuRI (HaeIII) #ER0151, (2012), pp. 1-3, downloaded from tools.thermofisher.com/content/sfs/manuals/MAN0012073_BsuRI_HaeIII_10_UuL_3000U_UG.pdf (Year: 2012).*

Prime-It II Random Primer Labeling Kit Instruction Manual (Catalog #300385), Agilent Technologies, Inc., 2015, downloaded from https://www.agilent.com/cs/library/usermanuals/public/300385.pdf (Year: 2015).*

Kathleen M. Gorman, et al. "Bi-allelic Loss-of-Function CACNA1B Mutations in Progressive Epilepsy-Dyskinesia" The American Journal of Human Genetics 104, 948-956, May 2, 2019 (Year: 2019).*

Groen, Justus L. et al.; "CACNA1B mutation is linked to unique myoclonus-dystonia syndrome"; Human Molecular Genetics; vol. 24, No. 4; 2015, DOI: 10.1093/hmg/ddu513; pp. 987-993.

Seo BA et al., "*Homo sapiens* calcium voltage-gated channel subunit alpha1 B (CACNA1B), transcript variant 1, mRNA", GenBank Registry No. NM_000718.4, Sep. 27, 2019.

Liu, Xin, "The Genetic Molecular Mechanism Study of Early Repolarization Associated Sudden Cardiac Death Resulted from A Calcium Channel Gene CACNA1C Mutation", Chinese Doctoral Dissertations Full-Text Database, Medical and Health Sciences, Nov. 15, 2017, ISSN:1674-022X, pp. E062-60.

Mencacci, Niccolo E. et al.; "The CACNA1B R1389H variant is not associated with myoclonus-dystonia in a large European multicentric cohort"; Human Molecular Genetics; vol. 24, No. 18; 2015, DOI: 10.1093/hmg/ddv255; pp. 5326-5329.

Stec, Sebastian et al.; "The world's largest family with familial atrio-ventricular nodal reentry tachycardia"; Kardiologia Polska; 2015; vol. 73, No. 12; pp. 1339; ISSN: 0022-9032.

Chizner, Michael A. ; "Paroxysmal Supraventricular Tachycardia"; Clinical Cardiology Made Ridiculously Simple ; vol. 22; Jul. 31, 2018; pp. 314-315.

Wu, Bin et al.; "XI. Paroxysmal supraventricular tachycardia"; Xinxueguanbing Ji Bingfazheng De Jianbie Zhenduan Yu Zhiliao; vol. 9; Jun. 30, 2019; pp. 249-251.

* cited by examiner

*Primary Examiner* — Stephen T Kapushoc
(74) *Attorney, Agent, or Firm* — NKL Law; Allen Xue

(57) ABSTRACT

A screening kit for paroxysmal supraventricular tachycardia contains a reagent for detecting a human CACNA1B gene c. 1700A>G mutation site at base No. 1700 in a coding region of CACNA1B gene from A to G.

1 Claim, 20 Drawing Sheets

Specification includes a Sequence Listing.

Proband
CACNA1B c. 1700A/A
CACNA1B:NM_000718.3:exon12:c.1700A
>G; p (Lys567Arg)
wild
mutant

SCREENING KIT FOR PAROXYSMAL SUPRAVENTRICULAR TACHYCARDIA

INCORPORATION OF SEQUENCE LISTING

This application contains a sequence listing submitted in Computer Readable Form (CRF). The CFR file contains the sequence listing entitled "PA288-0102_ST25.txt", which was created on Mar. 29, 2023, and is 128,122 bytes in size. The information in the sequence listing is incorporated herein by reference in its entirety.

TECHNICAL FIELD

The present invention belongs to the field of molecular diagnostic kits, and especially relates to a screening kit for paroxysmal supraventricular tachycardia.

BACKGROUND TECHNOLOGY

Arrhythmia is an important group of cardiovascular diseases, with a population incidence of about 3-5%, which seriously affects human health. In recent years, the tendency for familial clustering of arrhythmias has attracted extensive attention from scholars at home and abroad, and the progress in molecular genetics has been made. Paroxysmal supraventricular tachycardia is a common arrhythmia, including atrioventricular nodal reentrant tachycardia (AVNRT) and atrioventricular reentrant tachycardia (AVRT). AVNRT is the most common type among paroxysmal supraventricular tachycardias, and accounts for about 65% of all patients abroad and 40%-50% in China. The prevalence of AVNRT is about 22.5/10,000, the annual incidence is 35/100,000, and familial AVNRT accounts for 1.27% of the patient population. The vast majority of patients with AVNRT are not associated with organic heart diseases, and the electrocardiogram (ECG) at the time of the attack is characterized by normal QRS tachycardia, with a frequency of 150-250 beats/min, regular rhythm and sudden onset and sudden termination. Although it has been clinically demonstrated that AVNRT has a dual functional pathway, i.e. a fast and slow pathway, and the slow pathway ablation by radiofrequency catheter ablation (RFCA) is a well-established treatment. However, its etiology is unknown, and its pathogenesis remains to be elucidated. Unlike normal sinus rhythm, which is transmitted to the ventricles through the atrioventricular node and causes the contraction of heart, the anatomical and electrophysiological basis of AVNRT is the anisotropic conduction of the transitional cell region between the atrial muscle and the atrioventricular node, forming a fast and slow pathway, that is, dual atrioventricular nodal pathway (DAVNP). It has been suggested that the dual pathway is a congenital abnormality formed during the embryonic cardiac development. Clinically, the slow-fast type of AVNRT conducted in anterograde direction by the slow pathway and in retrograde direction by the fast pathway is the most common, and accounts for about 90% of AVNRT. In general, it is believed that in patients with DAVNT, the fast pathway has a long anterograde refractory period and a faster conduction velocity, while the slow pathway has a short anterograde refractory period and a slower conduction velocity. Sinus excitation can be conducted in the forward direction along both the fast and slow pathways at the same time. Because the conduction velocity of the slow pathway is slow, when the excitation is transmitted along the slow pathway to the lower pathway, the conduction is blocked due to the refractory period formed after the anterograde conduction along the fast pathway. However, during premature atrial contraction or stimulation, the excitation can be slowly and directly transmitted to the ventricle along the slow pathway after its conduction is blocked in the fast path with a long refractory period, and suddenly, a significantly prolonged PR interval appears on ECG, showing the characteristics of DAVNP conduction. At this time, as long as the excitation has a sufficient conduction delay in the slow pathway, it can be conducted back to the atrium along the fast pathway that has been out of the refractory period to form reentry, which can form slow-fast atrioventricular nodal reentrant tachycardia.

The heart receives dual innervation of the sympathetic and parasympathetic nerves. It has been shown that when sympathetic nerves are excited, the nerve endings release norepinephrine, which acts on β receptors of the heart, causing an increase in $Na^+$ and $Ca^{2+}$ influx, and thereby resulting in an increase in heart rate, a decrease in atrioventricular conduction time, and an increase in atrial and ventricular muscle contractility. When the vagus nerve is excited, the nerve endings release acetylcholine, which acts on M receptor, causes the change in the permeability of $K^+$ ion channels on the cell membrane, increases $K^+$ outflow, results in slower heart rate, prolongs atrioventricular conduction time, and reduces myocardial contractility. It is well known that when sympathetic activity is enhanced, it effectively shortens the effective refractory period of DAVNP by releasing norepinephrine, and thus promotes the induction and persistence of tachycardia; on the contrary, when vagal activity is enhanced, it can terminate or reduce the occurrence of supraventricular tachycardia by releasing acetylcholine and prolonging the atrioventricular (AV) nodal refractory period. Clinically, intravenous infusion of isoproterenol with sympathetic excitation was used to induce AVNRT and to evaluate the efficacy of clinical radiofrequency ablation. Although AVNRT is caused by a well-defined reentrant mechanism, its specific etiology is unknown. According to a recent European multicenter study, there is the presence of AVNRT in a family, suggesting that the disease may be related to genetic factors, but until now, no pathogenic genes have been reported.

$Ca^{2+}$ channels are one of the most important intracellular messengers widely present in the body, and almost all life activities are related to calcium signals. $Ca^{2+}$ channels are divided into voltage-gated, receptor-gated, and mechanically gated calcium channels, where the voltage-gated calcium channel (Cavs) is a transmembrane protein complex composed of $\alpha_1$, β, $\alpha_2\delta$, and γ subunits. α1 subunit is the main pore structure and contains four homologous repeat regions (I-IV) consisted of six transmembrane fragments (S1-S6); β, $\alpha_2\delta$, and γ are auxiliary subunits. $\alpha_1$ subunit determines the activity, electrophysiological properties, and pharmacology of calcium channels. $Ca^{2+}$ channels are divided into different channels according to the structure of $\alpha_1$ subunits: Cav1 (Cav1.1-1.4, collectively referred to as L-type), Cav2 (Cav2.1-P/Q, Cav2.2-N and Cav2.3-R), Cav3 (Cav3.1-3.3, collectively referred to as T-type), in which L-type and T-type of calcium channels are mainly distributed in cardiac myocytes. However, N-, P/Q- and R-type of calcium channels are mainly distributed in the nervous system. Cav2.2α1 subunit of N-type calcium channel is encoded by CACNAB gene. International research on the function of Cav2.2 calcium channel shows that Cav2.2 is an N-type calcium channel, which is mainly distributed in the presynaptic membrane of sympathetic nerve terminals and also expressed in parasympathetic nerve terminals. It regulates $Ca^{2+}$ influx and the release of neurotransmitter, and plays a leading role in the function of sympathetic nerve regulating cardiac conduction system. When the nerve impulse is transmitted to the nerve endings, Cav2.2 calcium channel opens and then $Ca^{2+}$ enter the cell, resulting in the release of neurotransmitters and corresponding biological effects.

Cav2.2 calcium channel coding gene, CACNA1B, is located in the long arm 9q34.3 of human chromosome 9. Its cDNA is 10.3 kb and encodes Cav2.2 calcium channel protein containing 2339 amino acid residue, which is mainly expressed in the nervous system, adrenal gland, testis and heart.

At present, voltage-gated calcium channels are known to play an important role in maintaining the calcium homeostasis, the normal structure and the physiological function of excitable cells, but there is no international study to prove that point mutation of CACNA1B gene is related to the occurrence of AVNRT. International colleagues have reported that CACNA1B has a point mutation (Cav2.2 R1389H) in three patients with arrhythmias in a family with myoclonic syndrome (CACNA1B mutation is linked to unique myoclonus-dystonia syndrome. Hum Mol Genet. 2015, 24(4): 987-993), but in subsequent sporadic patients, it has been demonstrated that the point mutation is a polymorphism that occurs in normal subjects, and its mutation rate does not differ between patients and normal subjects (The CACNA1B R1389H variant is not associated with myoclonus-dystonia in a large European multicentric cohort. Hum Mol Genet. 2015, 24(18): 5326-9).

In recent years, there have been scattered reports on AVNRT families (e.g. The world's largest family with familial atrioventricular nodal reentry tachycardia. Kardiol Pol. 2015; 73: 1339). If relevant pathogenic genes can be found, molecular diagnostic screening of AVNRT will be helpful for eugenics. However, there is little knowledge about its genetics. So far, no pathogenic genes have been reported, and relevant molecular diagnostic methods or kits have not been found yet.

Content of the Invention

The present invention is based on the study of AVNRT families, and using CACNA1B-K565R point mutation model in rats, determines whether N-calcium channel point mutation causes the occurrence of AVNRT by affecting $Ca^{2+}$ influx, the release of neurotransmitters, the activity of sympathetic nerves and $Ca^{2+}$/CaM/CaMKII signaling pathway, and elucidates the molecular pathological mechanism of the point mutation of CACNA1B gene causing the occurrence of familial AVNRT, so as to establish the first pathogenic gene and provide new targets and ideas for the diagnosis and treatment of AVNRT.

The object of the present invention is to provide a screening kit for paroxysmal supraventricular tachycardia.

The technical solutions of the present invention comprise:

A mutant gene fragment, which is a human CACNA1B gene with a c.1700A>G mutation site (The 1700$^{th}$ base is mutated from A to G in a coding region of CACNA1B gene).

A screening kit for paroxysmal supraventricular tachycardia, which comprises an optional reagent for detecting the c.1700A>G mutation site of the human CACNA1B gene.

A kit as described above, which further comprises an optional agent for amplifying a genomic DNA fragment comprising the mutation site.

A kit as described above, in which said reagents used to detect the c.1700A>G mutation site of the human CACNA1B gene are those used in sequencing.

A kit as described above, in which the related reagents used to detect the c.1700A>G mutation site of the human CACNA1B gene are those used in fluorescent quantitative PCR, restriction fragment length polymorphism methods, or a single-strand conformation polymorphism analysis.

A kit as described above, in which said paroxysmal supraventricular tachycardia is AVNRT.

The use of the agent for the detection of a c.1700A>G mutation site in the human CACNA1B gene in the preparation of a screening kit for paroxysmal supraventricular tachycardia;

said c.1700A>G mutation site in CACNA1B gene refers to the mutation site where base 1700 in the coding region of the CACNA1B gene changes from A to G.

The use mentioned above, in which said kit further comprises an optional agent for amplification of a genomic DNA fragment comprising the mutation site.

The use mentioned above, in which said relevant reagent for detecting the c.1700A>G mutation site in human CACNA1B gene is those used in sequencing, fluorescence quantitative PCR, a restriction fragment length polymorphism method, or a single strand conformation polymorphism analysis.

The use mentioned above, in which said paroxysmal supraventricular tachycardia is AVNRT.

A method for establishing an animal model of paroxysmal supraventricular tachycardia, which is to mutate the CACNA1B gene of an animal, so that amino acid 565 of the translated CACNA1B protein is mutated from K (lysine, corresponding to codon AAG or AAA) to R (arginine, corresponding to codons CGA, CGT, CGC, CGG, AGG, AGA); preferably, the animal is a rat.

The method for establishment of animal models mentioned above, wherein the technology used for gene mutation is the technology of CRISPR/Cas9.

In the present invention, it is found that the mutation of CACNA1B gene (c.1700A>G) is a genetic factor of AVNRT, and by detecting the mutation, paroxysmal supraventricular tachycardia, especially AVNRT, can be screened. The kit developed based on this principle could assist the diagnosis of paroxysmal supraventricular tachycardia (especially AVNRT), contribute to eugenics, guide doctors to prescribe the right medicine, and have a good application prospect. It can also help to build corresponding animal models and be used for drug screening.

In the present invention, using a rat model of CACNA1B-K565R point mutation, it is proved that the point mutation (c.1700A>G) of CACNA1B gene in the nervous system is related to the autonomic nerve, which can further lead to autonomic nerve-related arrhythmias, such as AVNRT, AVRT, etc. Therefore, the reagents detecting the mutation in CACNA1B gene (c.1700A>G) can be used to screen the patients with autonomic nerve-related arrhythmias, and can also provide new clinical therapeutic targets and ideas for AVNRT, atrial fibrillation and other diseases related to autonomic nerves, that is, cilnidipine, a relatively specific inhibitor of N-type calcium channels in nervous system, can be used to treat arrhythmias related to autonomic nerve. The clinical application prospect is very good.

Obviously, based on the above content of the present invention, according to the common technical knowledge and the conventional means in the field, without department from the above basic technical spirits, other various modifications, alternations, or changes can further be made.

By following specific examples of said embodiments, the above content of the present invention is further illustrated.

But it should not be construed that the scope of the above subject matter of the present invention is limited to the following examples. The techniques realized based on the above content of the present invention are all within the scope of the present invention.

EXAMPLES

Figure 1:
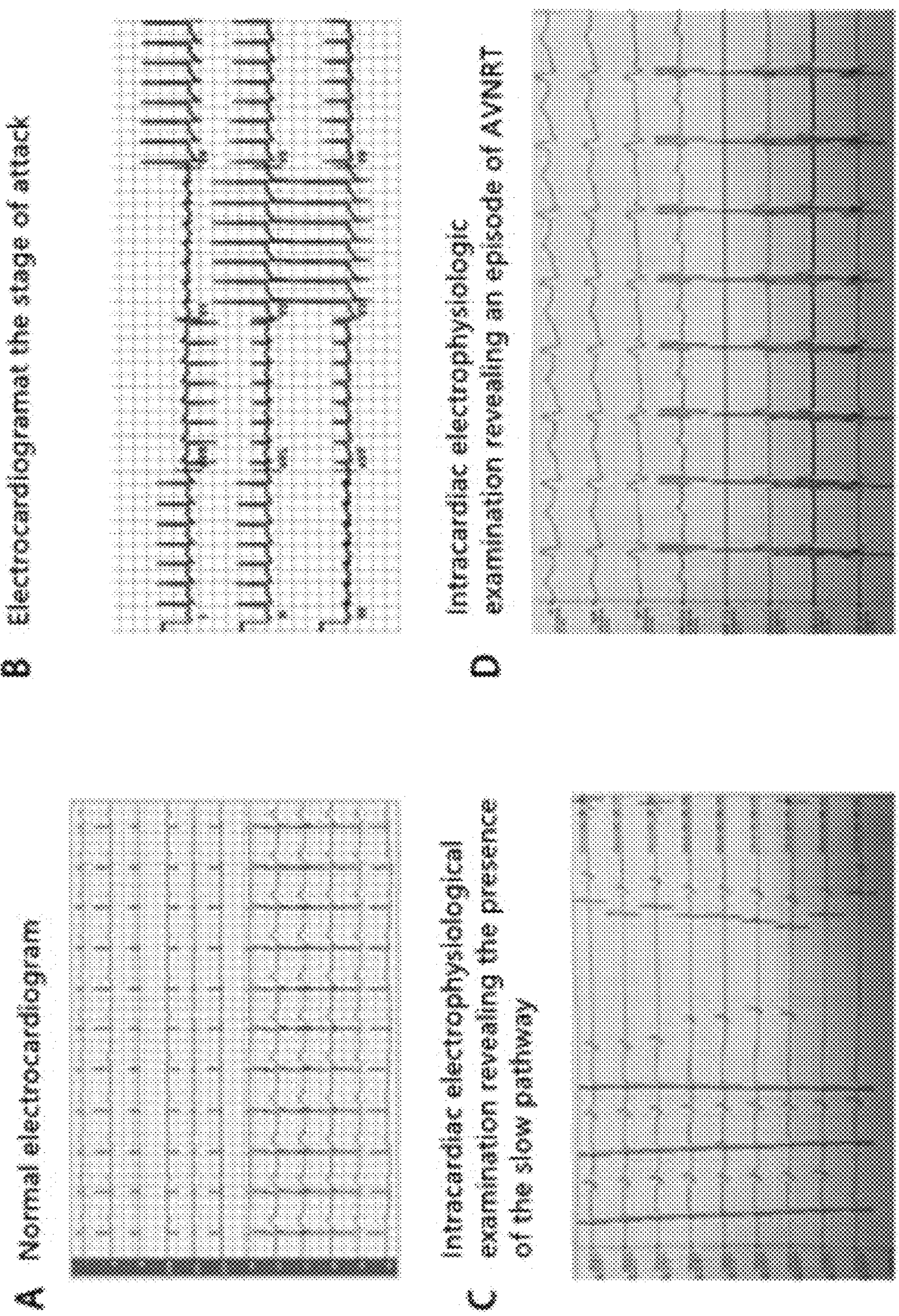
FIG. 1. Electrocardiographic and intracardiac electrophysiological findings of the proband.

Example 1 The Kit of the Present Invention (Sanger Sequencing Kit)

1. The Content of the Kit

The kit of the present invention comprised amplification reagents for amplifying gene CACNA1B (whose CDS is shown by SEQ ID NO:3 and the amino acid sequence is shown by SEQ ID NO:4), and Sanger sequencing reagents.

1.1 Amplification Reagents

PCR amplification reagents were used to amplify a DNA sequence where the SNP site was located, and its composition is shown in Table 1.

TABLE 1

PCR amplification reagents.

| Components | Concentration | Volume |
|---|---|---|
| PCRmixed solution | 2× | 600 μl |
| Primer pair | 10 μM | 100 μl |
| Pure water | | 2 ml |

The PCR mixture in Table 1 includes Taq enzyme, dNTP, magnesium ion and other components required for conventional PCR; the information of primer pair is shown in Table 2.

TABLE 2

Primers for gene amplification

| Primer name | SEQ ID | Sequence(5'→3') |
|---|---|---|
| Primer-F | SEQ ID NO: 1 | GATGGTTCCTTACGGAGA GGT |
| Primer-R | SEQ ID NO: 2 | AAGCACCCTGTGTGGCT GAT |

1.2 Sequencing Reagents

Sequencing reagents included the constituents listed in Table 3.

TABLE 3

Detection reagents for gene mutation typing (including reagents for purification)

| Constituents | Volume |
|---|---|
| Serum alkaline phosphatase | 120 μl |
| Restriction exonuclease | 6 μl |
| Purification buffer | 5 μl |
| Bigdye Mix | 15 μl |
| 5× buffer | 100 μl |
| $ddH_2O$ | 1 ml |
| F primer | 50 μl |

Wherein, F primer was a sequencing amplification primer, and its sequence was shown by SEQ ID NO:1.

2. Method of Use

DNA Extraction 2 ml of whole blood (anticoagulated with EDTA) was collected from the patients, whose genomic DNA was then extracted.

The DNA fragments containing the detected mutation sites were amplified by PCR, and the PCR amplification system for each mutation site was shown in Table 4.

TABLE 4

Amplification system.

| Constitents | Concentration | Volume |
|---|---|---|
| DNA sample | 50 ng/μl and above | 1 μl |
| PCR reagent mixture | 2× | 10 μl |
| Primer pair | 10 μM | 2 μl |
| Pure water | | 7 μl |

The reaction procedure is shown in Table 5.

TABLE 5

The reaction procedure.

| Procedure | Temperature | Time |
|---|---|---|
| 1 | 94° C. | 3 min |
| 2 | 94° C. | 30 s |
| 3 | 60° C. | 30 s |

TABLE 5-continued

The reaction procedure.

| Procedure | Temperature | Time |
|---|---|---|
| 5 | 72° C. | 1 min |
| 6 | Making two steps backwards, with a total of 30 times | |
| 7 | 72° C. | 5 min |

Detection of PCR Products:

PCR products were detected by 2% agarose gel electrophoresis, to observe the effect of PCR reaction and determine the amount added as template in the subsequent reaction.

3) Sanger Sequencing Assay

Step 1: Purification of PCR Products

The system is shown in Table 6.

TABLE 6

Purification system of PCR products.

| Constituents | Volume |
|---|---|
| PCRproducts | 4 μl |
| Serum alkaline phosphatase | 2 μl |
| Restriction exonuclease | 0.1 μl |
| Purification buffer | 0.1 μl |

Reaction Conditions:

| | |
|---|---|
| 1. Enzymatic digestion at 37° C. | 30 min |
| 2. Inactivation at 80° C. | 15 min |
| 3. Preservation at 4° C. | |

Step 2: Sanger Sequencing

The aforementioned typing detection reagent was used as a sequencing amplification reagent for Sanger sequencing of the PCR product purified in the first step.

If the 1700th base of the coding region of gene CACNA1B was G according to the sequencing result, the mutation to be detected in the present invention had been carried out, indicating that the subject was susceptible to AVNRT.

It should be understood that the present example was a sequencing kit, which aimed to detect whether there was a mutation at base 1700 in the coding region of gene CACNA1B. According to the common knowledge in the art, all means that could detect gene mutation, such as fluorescence quantitative PCR, restriction fragment length polymorphism detection, single strand conformation polymorphism analysis, etc., could detect whether the 1700th base of the coding region of gene CACNA1B was mutated.

The beneficial effects of the present invention would be further demonstrated by way of experimental examples in the following.

Experimental Example 1 Family Clinical Validation

1. The Proband of AVNRT in a Pedigree and the Family Status (1) Proband: The proband was a middle-aged woman who presented with paroxysmal palpitations, which could be self-terminated after attack for tens of minutes to several hours. The electrocardiogram indicated the paroxysmal supraventricular tachycardia, and the cardiac ultrasound report showed the normal heart size and function, and thus she was diagnosed with AVNRT in Sichuan Provincial People's Hospital. The electrocardiographic and intracardiac electrophysiological results are shown in FIG. 1.

(2) Family: When asking about the medical history, it was known that the patient was in a tachycardia family. After asking for history of tachycardia, ambulatory electrocardiogram, through esophagus atrial pacing, intracardiac electrophysiological examination and so on, it was found that there were 4 patients in this family. The pedigree is shown in FIG. 2.

2. Sequencing Validation

Figure 2:
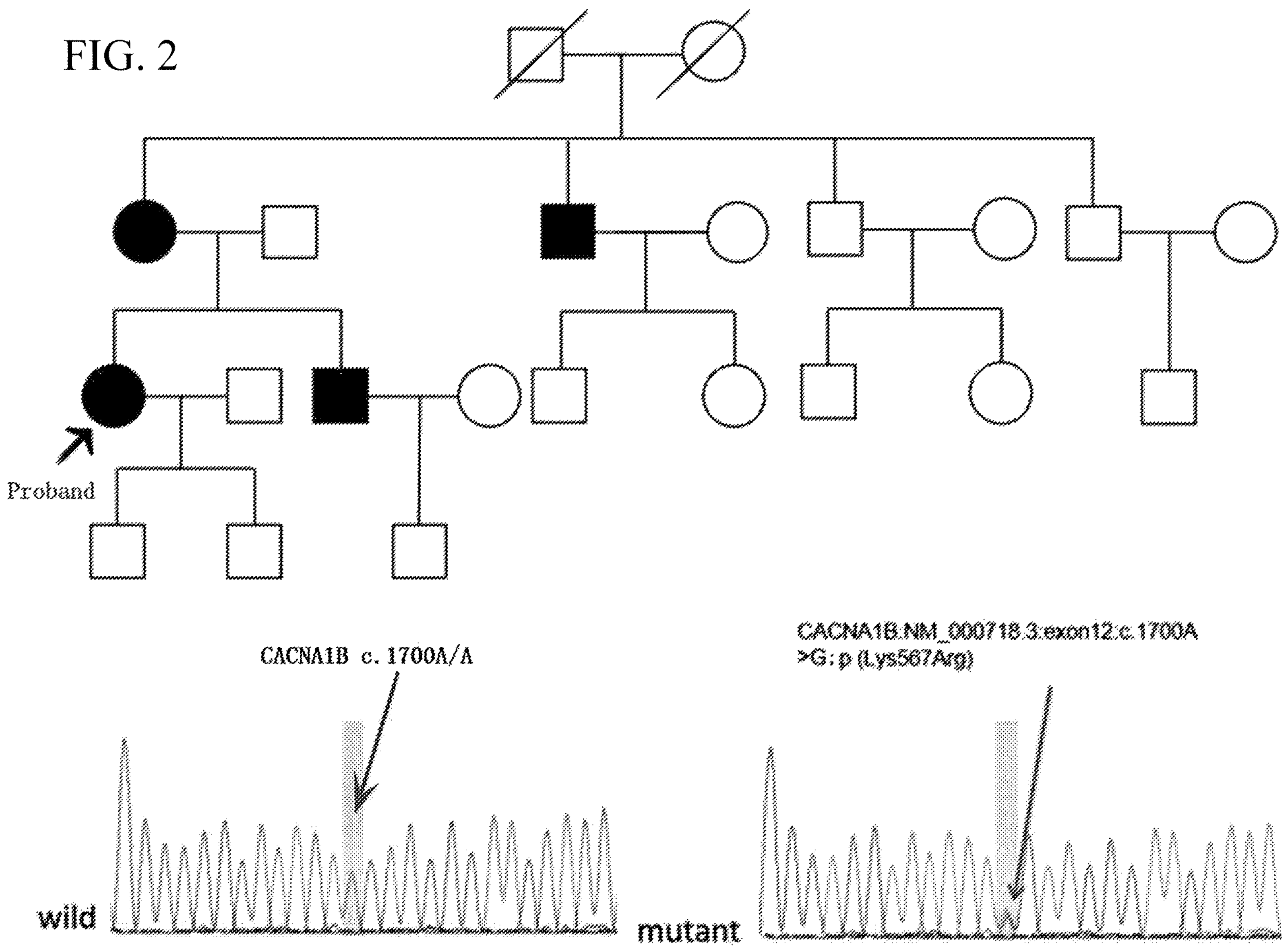
FIG. 2. The pedigree and the sequencing diagram of the proband. In the figure, arrow, indicating the proband; filled circles and filled squares, indicating the patient; slashes, indicating the death; wild, indicating no mutation; and mutant, indicating the mutation.

Sanger sequencing of gene CACNA1B from all living members of the patient's family revealed that the mutation of CACNA1B(c.1700A>G,p.K567R) was present in all patients, but not in normal subjects, as shown in FIG. 2.

This experimental example demonstrated that the mutation of CACNA1B(c.1700A>G,p.K567R) was significantly associated with AVNRT; the screening of AVNRT could be realized by detecting the presence or absence of this mutation.

AVNRT is the main subtype of paroxysmal supraventricular tachycardia, and theoretically, detecting the mutation of CACNA1B(c.1700A>G,p.K567R) could also be used for preliminary screening of paroxysmal supraventricular tachycardia.

Experimental Example 2 Bioinformatics Analysis

The conservation of CACNA1B calcium channel protein was analyzed by phylogenetic tree, and PolyPhen was used to predict whether the mutation of CACNA1B(c.1700A>G) was harmful.

Figure 3:
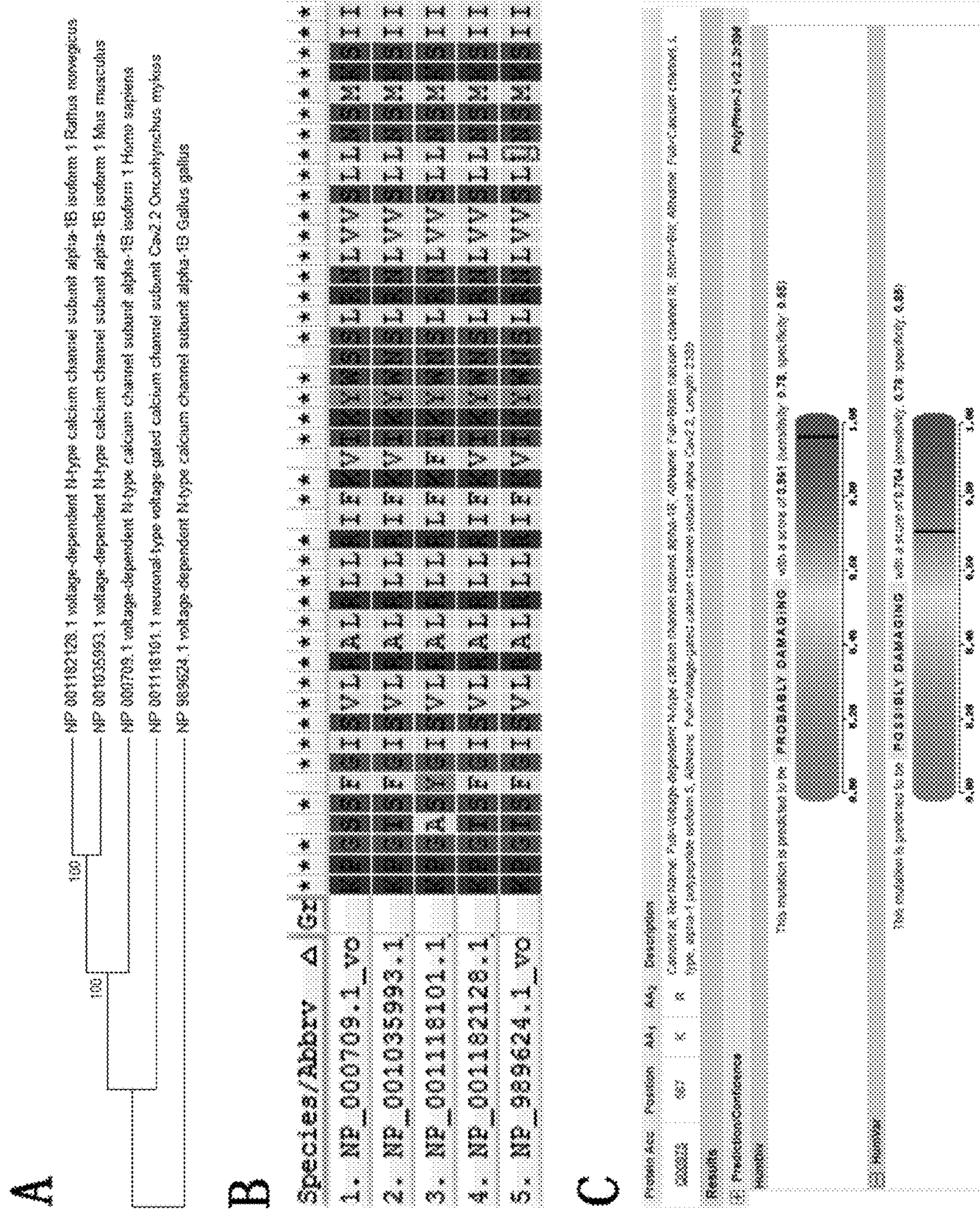
FIG. 3. The phylogenetic tree, the similarity comparison of protein sequences and the deleterious results of gene mutations predicted by a software. In Section B, NP_000709.1 is of the amino acid sequence represented by SEQ ID NO: 4; NP_001035993.1 is of the amino acid sequence represented by SEQ ID NO: 9; NP_001118101.1 is of the amino acid sequence represented by SEQ ID NO: 10; NP_001182128.1 is of the amino acid sequence represented by SEQ ID NO: 8; and NP_989624.1 is of the amino acid sequence represented by SEQ ID NO: 11.

Phylogenetic analysis showed that human CACNA1B calcium channel protein and gene CACNA1B in genomes of rats, mouse and zebrafishes were evolutionarily highly conserved. Protein sequence alignment showed that the 567$^{th}$ amino acid residues of human CACNA1B were all K (lysine), and gene CACNA1B was highly conserved in all species. The bioinformatics online software PolyPhen2 predicted that the mutation of CACNA1B(c.1700A>G) was harmful (FIG. 3).

Experimental Example 3 Zebrafish Embryo Assays

1. Method

In order to evaluate the function of human gene CACNA1B with point mutations, the present inventors first cloned the full-length CDS of human gene CACNA1B with or without point mutations (c.1700A>G), which was constructed into plasmids, to obtain recombinant plasmids, and then the corresponding mRNA was prepared by in vitro transcription (using mMESSAGE mMACHINE™T7 Ultra Transcription Kit(Ambion), according to the instructions). Fertilized eggs of zebrafishes were collected by conventional methods, and then the wild-type mRNA and the point-mutant mRNA of gene CACNA1B were microinjected into zebrafish embryos at 50 ng/ml, 100 ng/ml, and 200 ng/ml, respectively(with an injection volume of 1 ml/embryo). Zebrafish embryos were collected after development to 48 hpf (48 h after fertilization) (at the same time, the uninjected embryos at the same development stage were collected as controls). Micromorphology of embryos was observed one by one, and the heart rate was counted. When development to 48 hpf and 72 hpf, the transcriptomes of zebrafish embryos were sequenced for pathway enrichment analysis.

Wherein, the method used for the construction of recombinant plasmids was as follows:

The CDS was synthesized by a commercial company and cloned into pXT7 vectors. EcoRI (no such cleavage site in CDS) cleavage site was introduced at the 5'-end, while SpeI (no such cleavage site in CDS) cleavage site was introduced at the 3'-end, and pXT7-CACNA1B(WT) was finally obtained.

The synthesized pUC57-CACNA1B(WT) was used as the original plasmid, and the point mutation sequence AgeI-CACNA1B(MUT-part)-SalI (an incomplete CACNA1B sequence containing the mutation site, as shown by SEQ ID NO:5) was obtained by overlapping PCR. pUC57-CACNA1B(MUT) was obtained by homologous recombination, and then CDS was inserted into pXT7 vector by double enzyme digestion.

Wherein, the heart rate counting method was as follows:

Zebrafish larvae were anesthetized with 0.2 mg/mL of tricaine (ethyl 3-aminobenzoate methanesulfonate), and their heartbeat was observed under the microscope and counted by a counter for 20 seconds. Twenty embryos were randomly selected from each group at each stage.

2. Results 2.1 Proportion of Pericardial Edema

As shown in Table 7, the pericardial edema was lower in each group (less than 5%), suggesting that the pericardial edema was not obvious.

TABLE 7

Proportion of pericardial edema(wt, wild type; mut, mutant type).

| | Injection concentration | | | | | | |
|---|---|---|---|---|---|---|---|
| | wt mRNA | | | mut mRNA | | | Uninjected |
| Abnormal proportion | 50 ng/μl | 100 ng/μl | 200 ng/μl | 50 ng/μl | 100 ng/μl | 200 ng/μl | control 0 |
| Pericardial edema counts | 3 | 1 | 0 | 0 | 0 | 4 | 1 |
| Total amount observed | 146 | 98 | 163 | 196 | 135 | 125 | 189 |
| Percentage (%) | 2.05% | 1.02% | 0 | 0 | 0 | 3.2% | 0.53% |

2.2 Proportion of Malformations

As shown in Table 8, malformations other than pericardial edema were also lower in each group (less than 5%, except for 5.6% in 200 ng/μl group), suggesting that teratogenicity was not evident.

TABLE 8

Proportion of malformations(wt, wild type; mut, mutant type).

| | Injection concentration | | | | | | |
|---|---|---|---|---|---|---|---|
| | wt mRNA | | | mut mRNA | | | Uninjected |
| Abnormal proportion | 50 ng/μl | 100 ng/μl | 200 ng/μl | 50 ng/μl | 100 ng/μl | 200 ng/μl | control 0 |
| Malformation counts | 1 | 1 | 0 | 0 | 3 | 7 | 1 |
| Total amount observed | 146 | 98 | 163 | 196 | 135 | 125 | 189 |
| Percentage (%) | 0.68% | 1.02% | 0 | 0 | 2.22% | 5.6% | 0 |

2.3 Heart Rate

Figure 4:
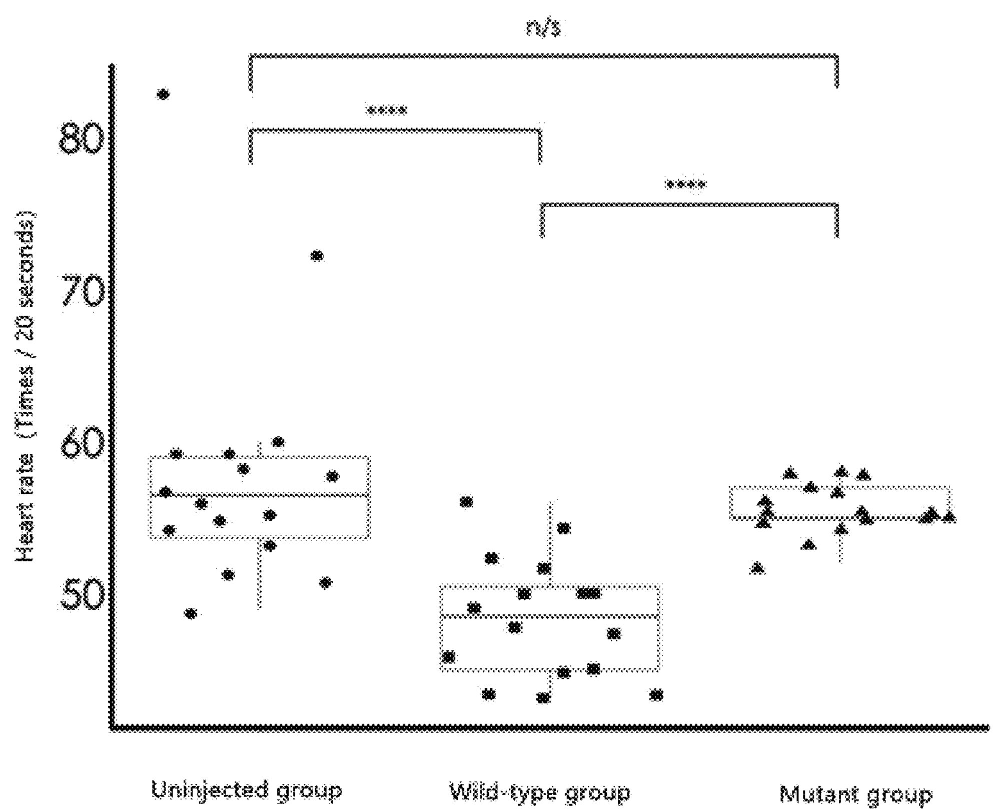
FIG. 4. Results of overexpression of human CACNA1B (c.1700A>G/p.K567R) in zebrafish embryos. As shown, the heart rate of 48 hpf embryos was significantly lower ($P<0.0001$) than that of the control group after overexpression of wild-type human CACNA1B mRNA (50 ng/μl) in zebrafish embryos, while the heart rate of 48 hpf embryos injected with mutant mRNA (50 ng/μl) was not different from that of the control 48 hpf embryos ($P>0.05$).

The heart rate of the embryos injected with wild-type mRNA was significantly lower than that of the control, and also significantly lower than that of the embryos injected with point-mutated mRNA; however, the heart rate of the control was not significantly different from that of the embryos injected with point-mutated mRNA (FIG. 4), suggesting that the point mutation of CACNA1B (c.1700 A>G/p.K567R) was associated with the heart rate.

2.4 Transcriptome Analysis

Figure 5:
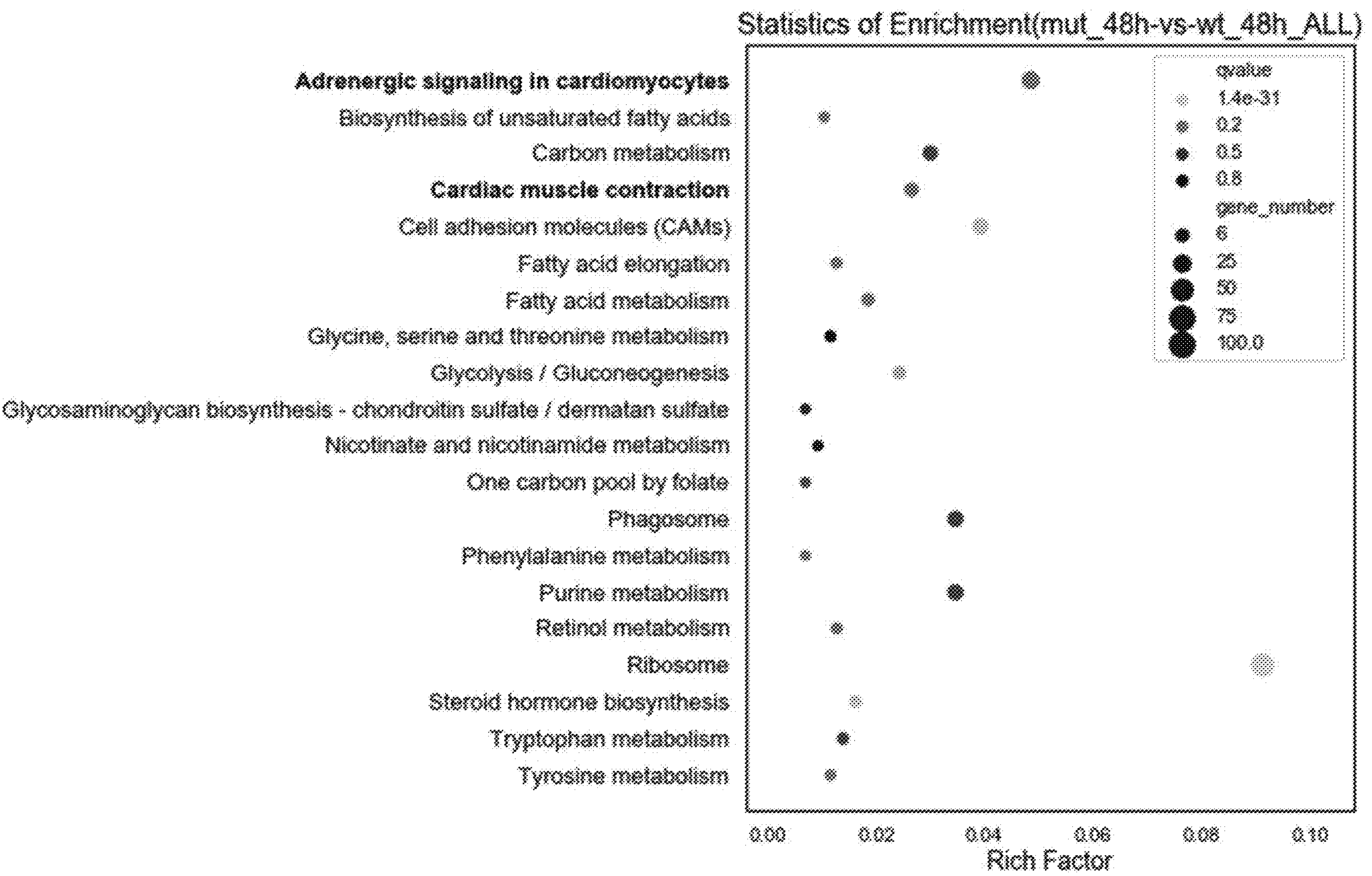
FIG. 5. Comparison of pathway enrichment analysis of differential gene expression in 48 hpf embryos (comparison of wild type and mutant type).
Figure 6:
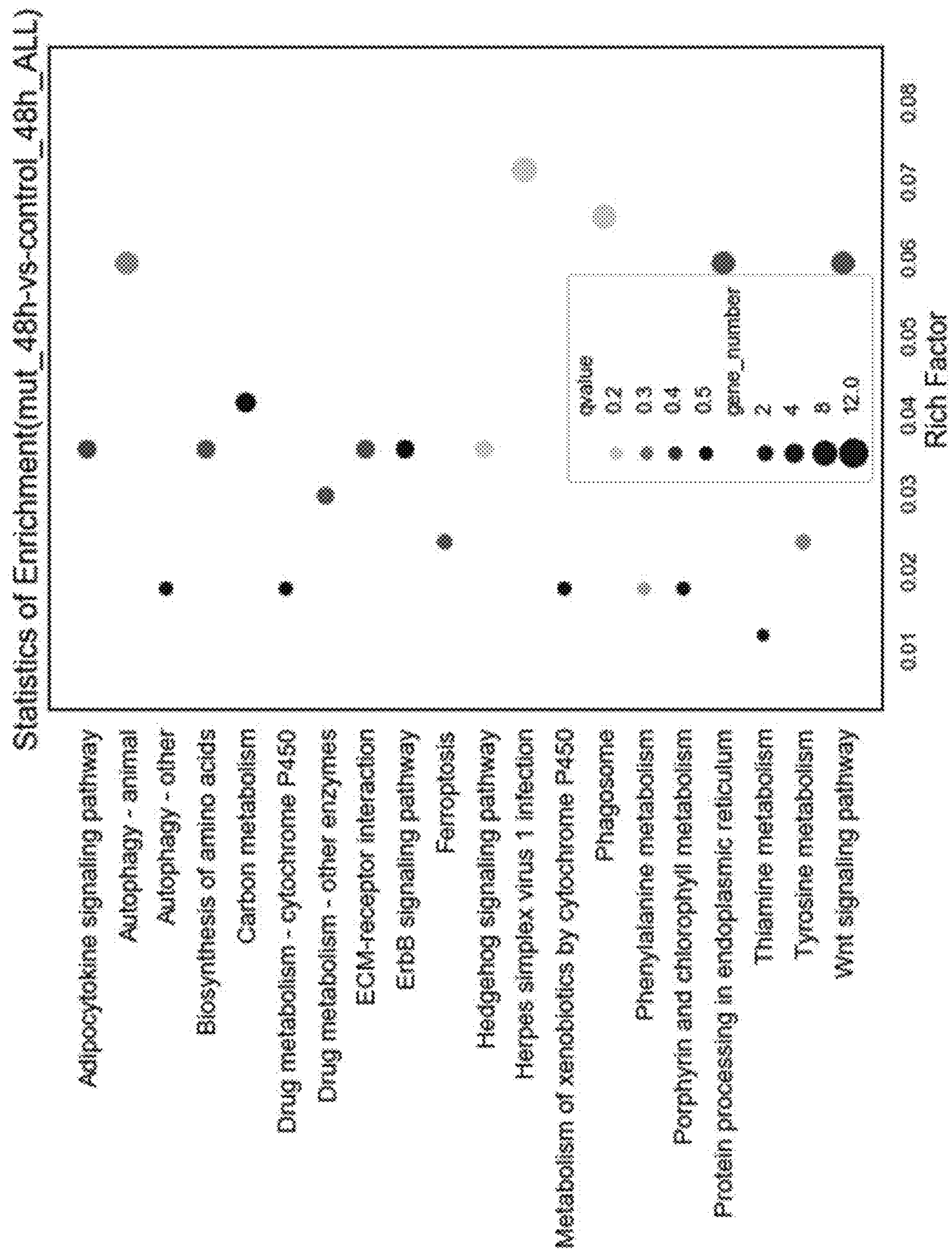
FIG. 6. Comparison of pathway enrichment analysis of differential gene expression in 48 hpf embryos (comparison of wild type and the control).
Figure 7:
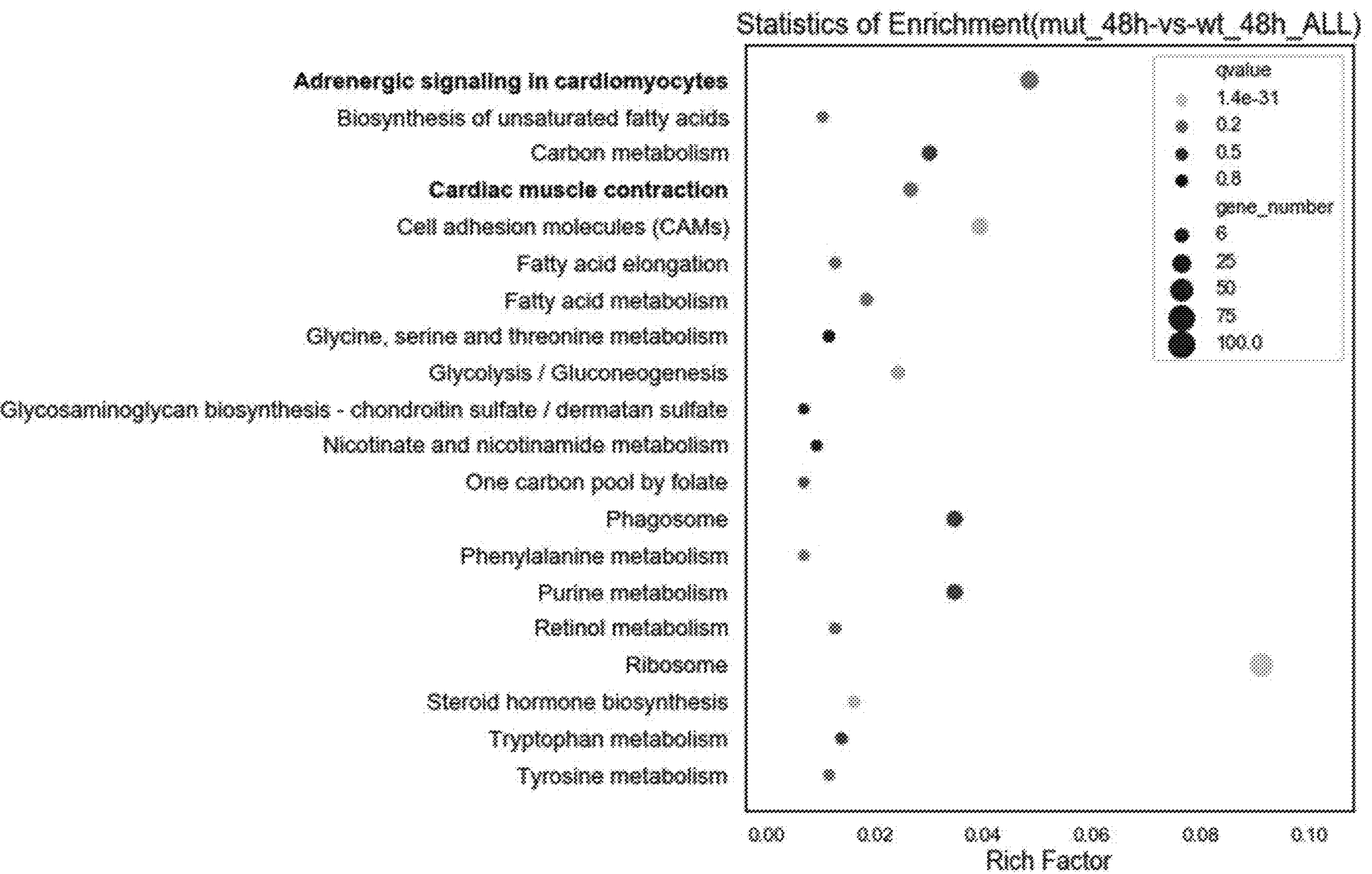
FIG. 7. Comparison of pathway enrichment analysis of differential gene expression in 72 hpf embryos (comparison of wild type and mutant type).
Figure 8:
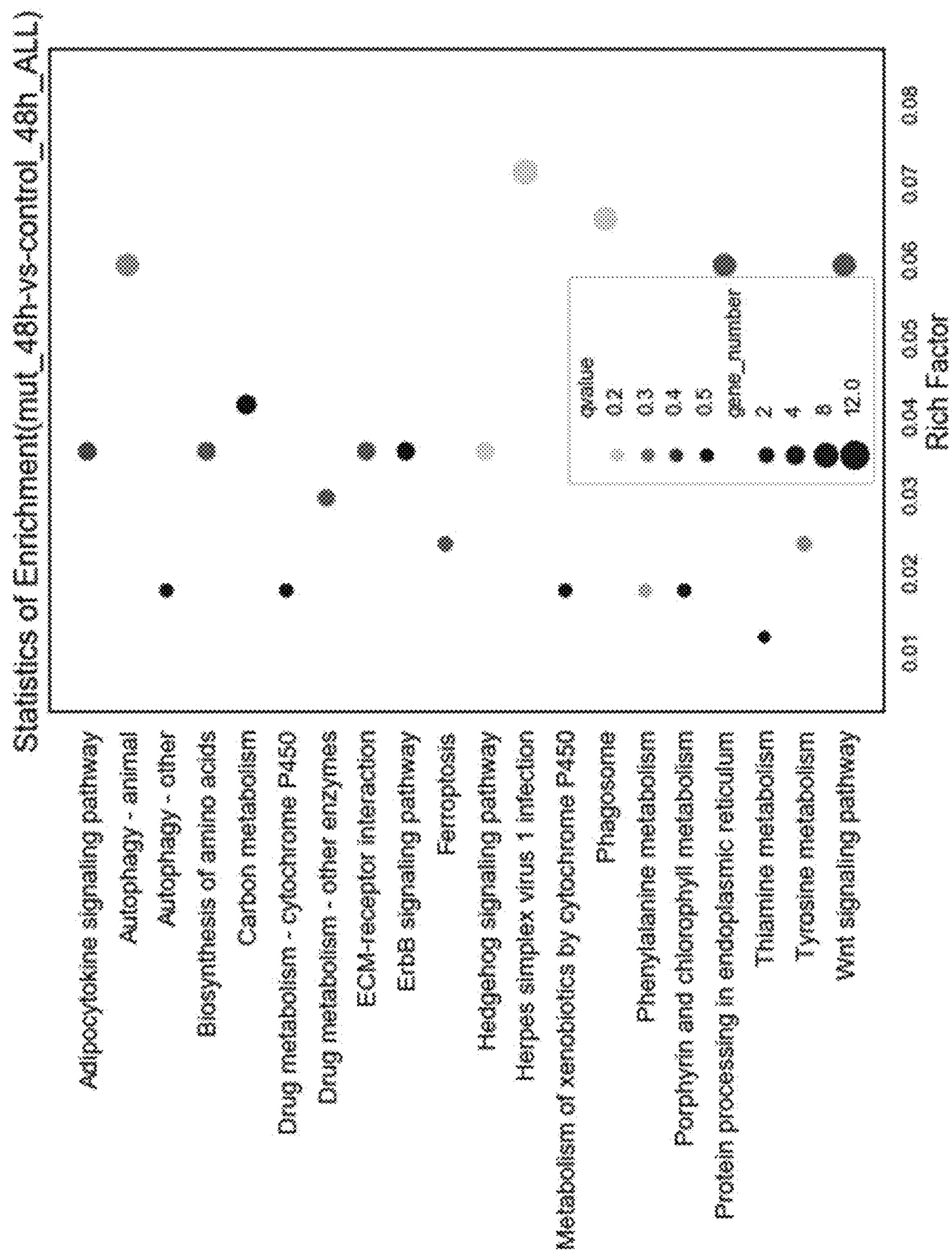
FIG. 8. Comparison of pathway enrichment analysis of differential gene expression in 72 hpf embryos (comparison of wild type and the control).

As shown in FIGS. 5 and 6, the expression of genes related to cardiac adrenergic signaling and cardiac contractile pathways (the first 20 pathways being enriched) in zebrafishes overexpressing point-mutant human CACNA1B (c.1700A>G/p.K567R) was significantly abnormal at 48 hpf, compared with zebrafishes overexpressing wild-type human CACNA1B mRNA and uninjected controls. As shown in FIGS. 7 and 8, the expression of genes related to cardiac adrenergic signaling, calcium signaling, and cardiac contractile pathways (the first 20 pathways being enriched) in zebrafishes overexpressing point-mutant human CACNA1B(c.1700A>G/p.K567R) was significantly abnormal at 72 hpf, compared with zebrafishes overexpressing wild-type human CACNA1B mRNA and uninjected controls.

The results of this experimental example showed that the overexpression of CACNA1B with/without mutations did not cause organic cardiac diseases, which was consistent with AVNRT; the overexpression of gene CACNA1B could induce cardiac dysfunction in zebrafishes, which was characterized by arrhythmia (lowering), while gene CACNA1B with point mutation (c.1700A>G) lost the function of inducing arrhythmia in zebrafishes, showing a dominant negative effect (loss of function). This phenomenon was also confirmed in transcriptome analysis.

This experimental example further demonstrated that the c.1700A>G mutant type of CACNA1B gene may cause a higher heart rate than the wild type of CACNA1B gene, and the mutation did not lead to organic cardiac diseases. The c.1700A>G mutation of CACNA1B gene is an important cause of tachycardia.

Experimental Example 4 Experiment of Cacna1b(K565R)Point Mutation in Rats

In order to further verify the effect of c.1700A>G mutation in gene CACNA1B (the amino acid mutation of the corresponding protein is the mutation of K to R, abbreviated as p.K567R) on the heart rate, the inventors used CRISPR/Cas9 technology, a conventional gene point mutation technology in the art, to construct the mutated rats having point-mutant CACNA1B (the mutant site was p.K565R in rats due to the difference between human and rat gene sequences), to observe whether the rats presented the clinical features of AVNRT.

1. Method

The CRISPR/Cas9 technology was used to construct the mutated rats having point-mutant CACNA1B(p.K565R), and the procedures were as follows:

gRNA was designed and synthesized by in vitro transcription, and a homologous recombination vector (Donor vector) was constructed. Cas9, gRNA and Donor vector were microinjected into fertilized eggs of rats at the same time. Cas9 protein bound to the target site under gRNA guidance, and thus caused DNA double-strand breaks. Donor vector repaired the broken double-strand by homologous recombination, thereby realizing the gene modification of the target site. The fertilized eggs after microinjection were transplanted into the uterus of rats, and then F0 rats were born. The point mutation-positive rats were obtained by PCR and sequencing. Then, the male and female F0 rats with a positive point mutation were mated to obtain F1 generation. The rats having point-mutant CACNA1B(p.K565R) were obtained by PCR and sequencing.

The related sequence was as follows:

| Name | Sequence | SEQ ID |
|---|---|---|
| gRNA | GTCTGGGCTGCCATCAAGCC | SEQ ID NO: 6 |
| Donor | GGTACTGTTTCTTTCAGGTGATT GTGGGGAGTATCTTTGAAGTAGT CTGGGCTGCCATT**CGG**CCAGGAA CCTCCTTCGGAATCAGTGTGCTG CGGGCTCTCCGACTGCTGAGGAT TTTCA | SEQ ID NO: 7 |

The gRNA-targeted PAM sequence was AGG; the bold part in Donor was the target point mutation sequence, and the underlined part was the synonymous mutation base for the mutation of PAM.

Figure 9:
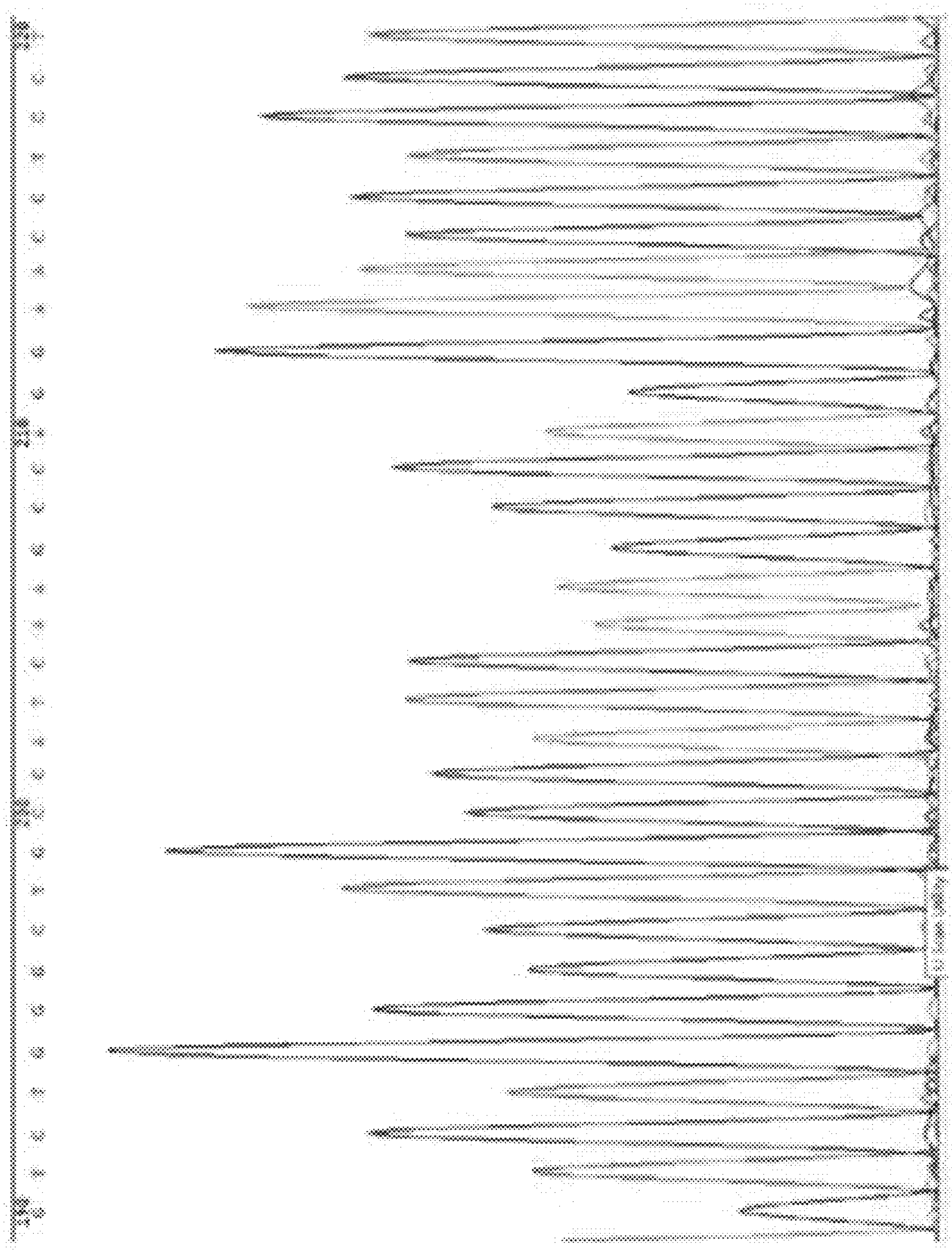
FIG. 9. Sequencing result of a wild-type rat.
Figure 10:
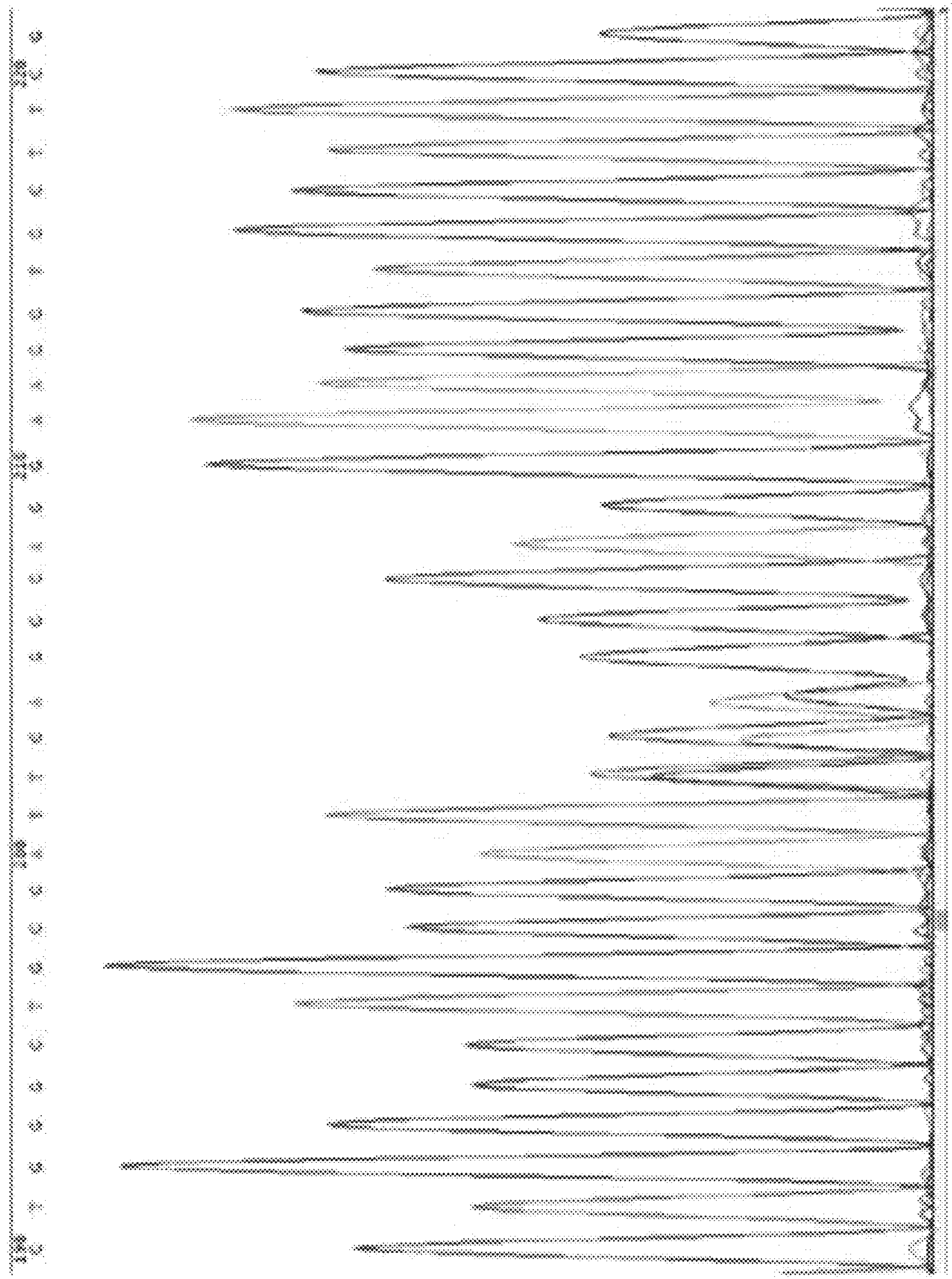
FIG. 10. Sequencing result of heterozygous rat with a Cacna1b point mutation (c.1694A>G/p.K565R, the 567th amino acid mutation caused by a point mutation in the human CACNA1B gene corresponding to the 565th amino acid in the rat.).
Figure 11:
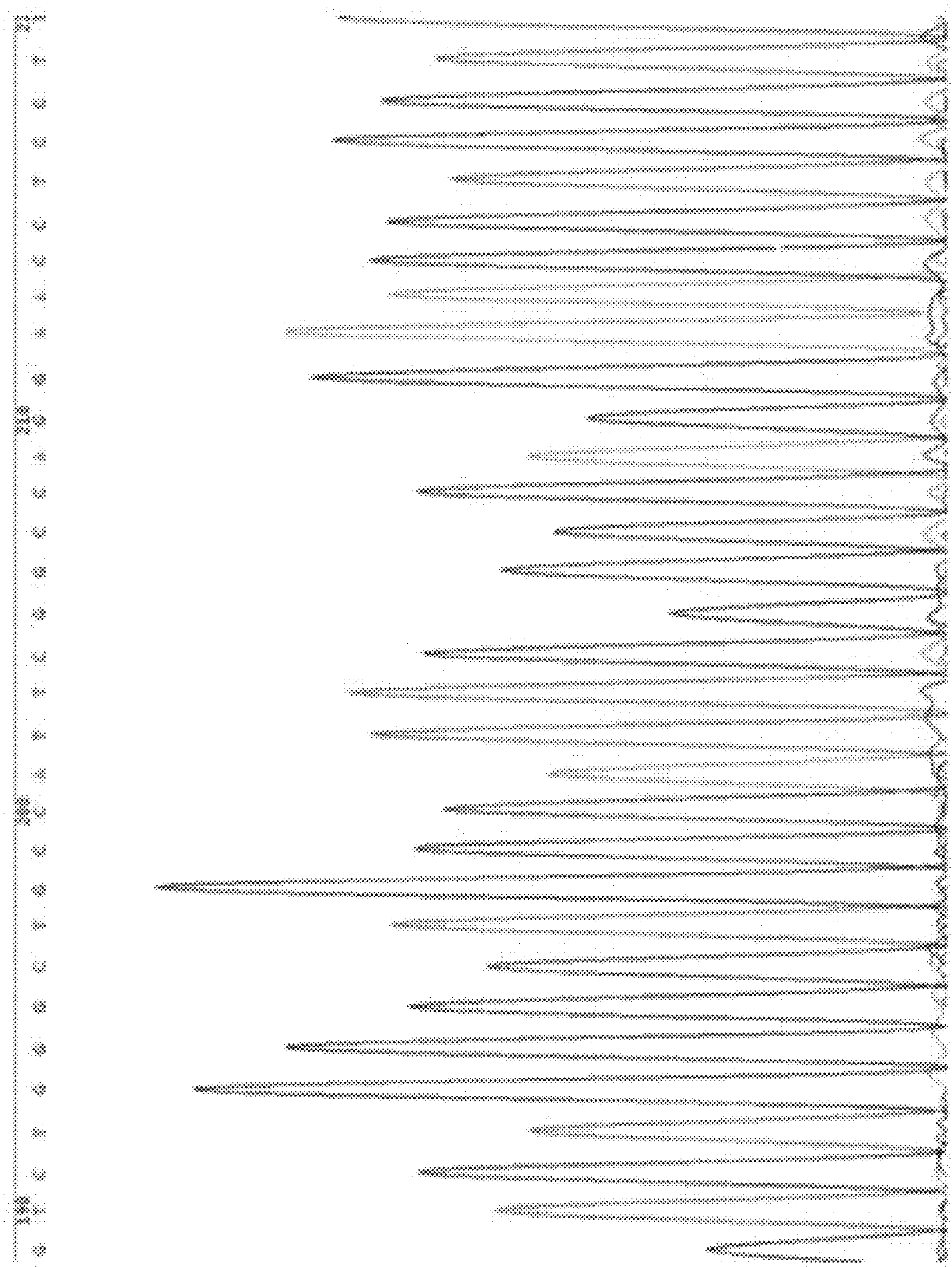
FIG. 11. Sequencing result of a homozygous rat with a Cacna1b point mutation (c.1694A>G/p.K565R). The sequences in FIGS. 9-11 are from the nucleotide sequence represented by SEQ ID NO: 12.

After obtaining the mutated rat shaving CACNA1B (p.K565R) point mutations, the genotypes were sequenced and identified (FIG. 9-11). Genotype identification and results of breeding rats:the target gene sequence of wild-type rat was ATCAAG, and the encoded amino acids were isoleucine and lysine; the corresponding sequences of heterozygous rats with point mutations were ATCAAG and ATTCGG, in which the first three bases ATC were synonymouslymutatedas ATT, and the encoded amino acid was isoleucine, while the latter three bases AAG were mutated as CGG, and the encoded amino acid was mutated from lysine to arginine. The corresponding sequence of homozygous rats having point mutations was ATTCGG.

The body weight, long-term average heart rate, electrocardiogram, blood pressure and body temperature of rats were monitored, and the depress reflex and intracardiac electrophysiology of rats were examined.

After the above monitoring/examination, rats were sacrificed, and the cardiac shape and size as well as the myocardial tissue (HE staining) were compared for homozygous rats with CACNA1b point mutations, heterozygous rats with CACNA1b point mutation and wild-type rats.

2. Results 2.1 General Conditions of Rats with CACNA1B(p.K565R) Point Mutations

Figure 12:
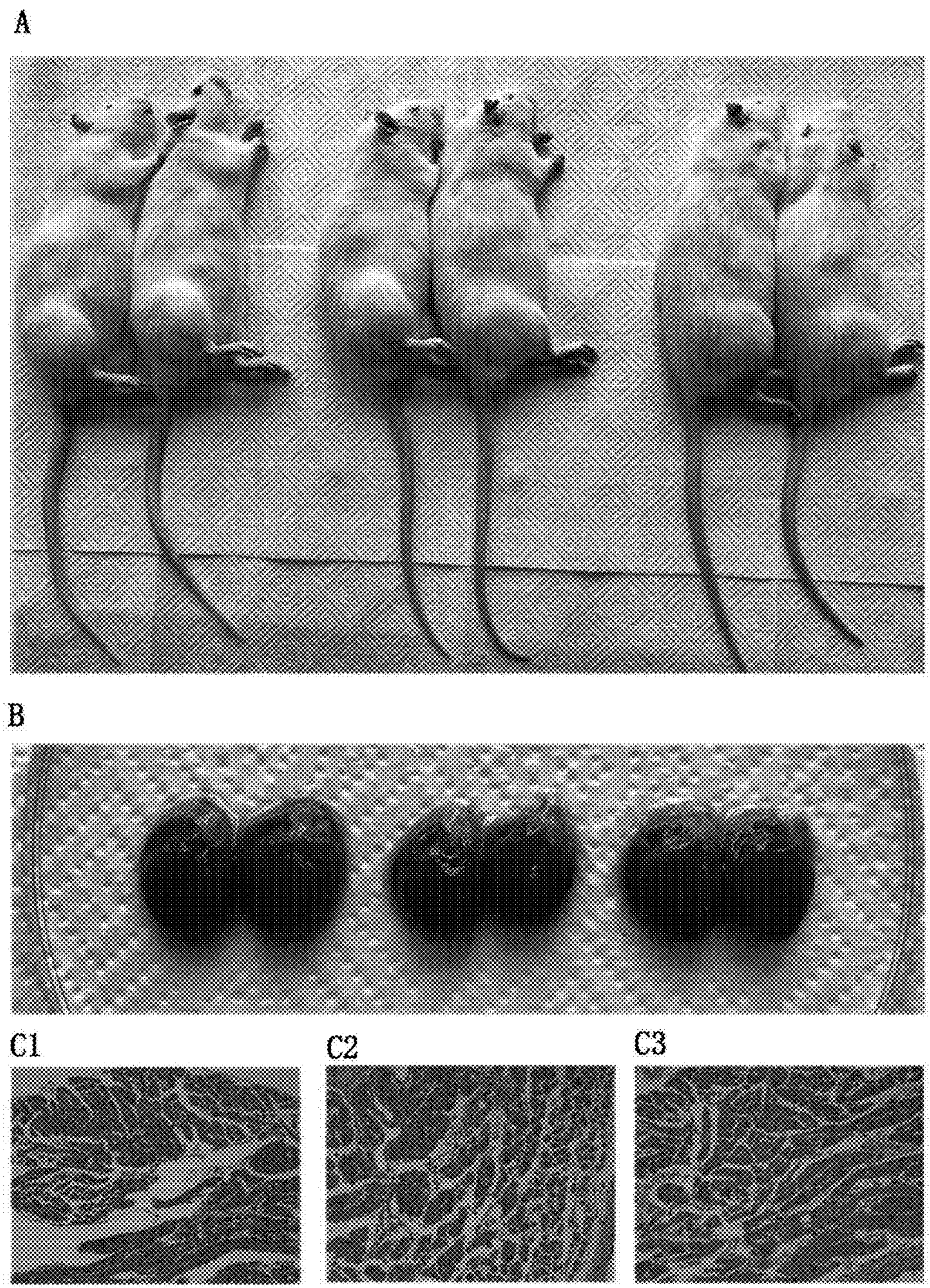
FIG. 12. Observations on general conditions in rats with point mutations. A, growth and development; B, heart size; C1-C3, HE staining of heart tissue; A, wild-type rats, heterozygous rats with a point mutant and homozygous rats with a point mutant; B, hearts of wild-type rats, heterozygous rats with a point mutant and homozygous rats with a point mutant; C, the results for HE staining of heart tissues of wild-type rats, heterozygous rats with a point mutant and homozygous rats with a point mutant.

For homozygous rats with CACNA1b point mutations, heterozygous rats with CACNA1b point mutation and wild-type rats, there were no differences in the growth and development, heart size, and HE staining of heart tissues (FIG. 12).

Figure 13:
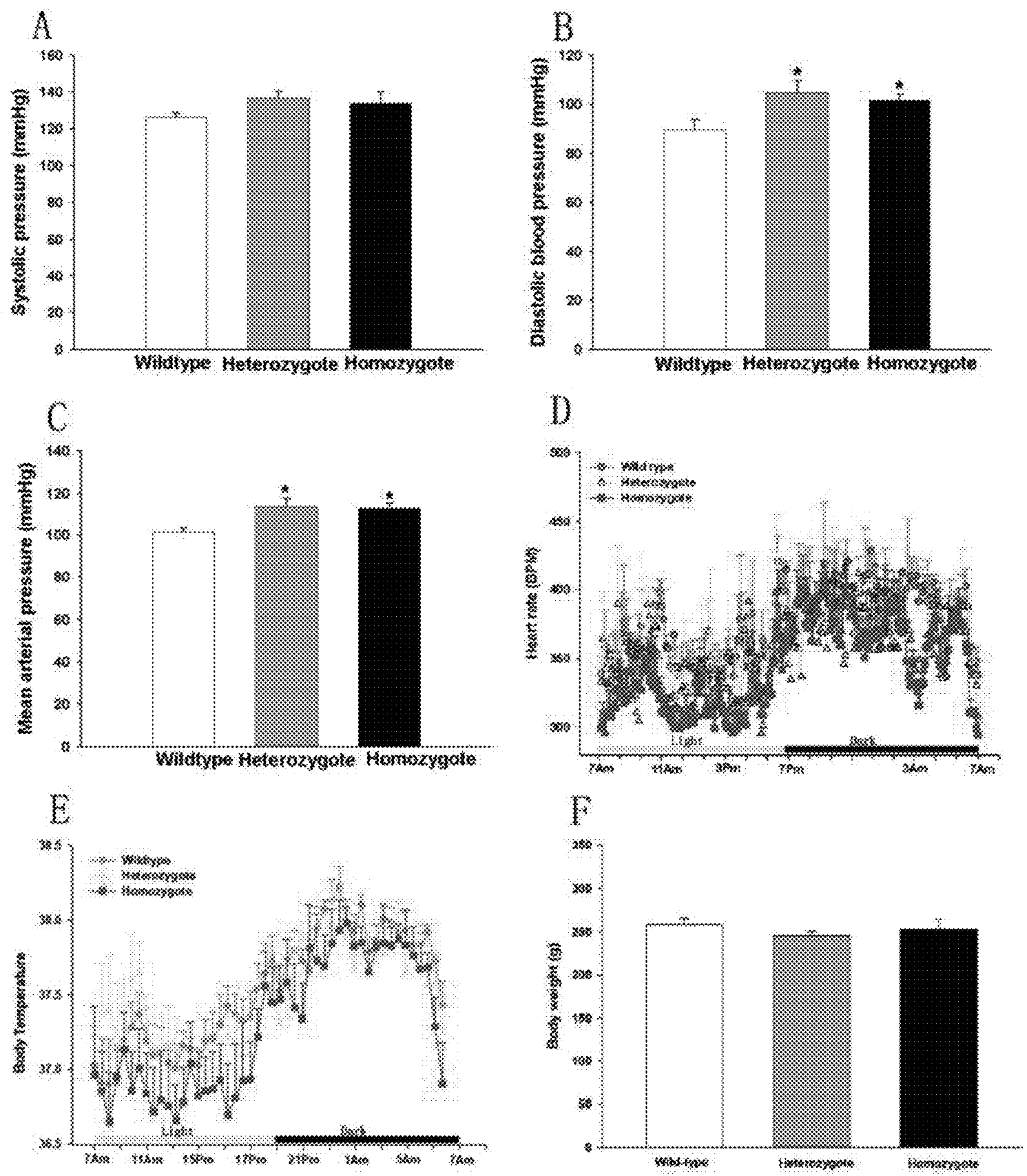
FIG. 13. Results of systolic pressure, diastolic pressure, mean arterial pressure, heart rate, body temperature and body weight for three groups of rats (3-month-old females). A, systolic pressure; B, diastolic pressure; C, mean arterial pressure; D,24-h ambulatory heart rate; E,24-h temperature change; F, weight. Wildtype: wild-type rat; Heterozygote, heterozygous rats with a point mutant; Homozygote, homozygous rats with a point mutant.

2.2 Monitoring Results of Body Weight, Heart Rate and Activity of Rats having CACNA1B(p.K565R) Point Mutations For homozygous rats with CACNA1b point mutations, heterozygous rats with CACNA1b point mutation and wild-type rats, there were no differences in the body weight, long-term mean heart rates, and the temperature, and only the diastolic pressure and the mean arterial pressure were slightly increased (FIG. 13).

2.3 Depress Reflex

Figure 14:
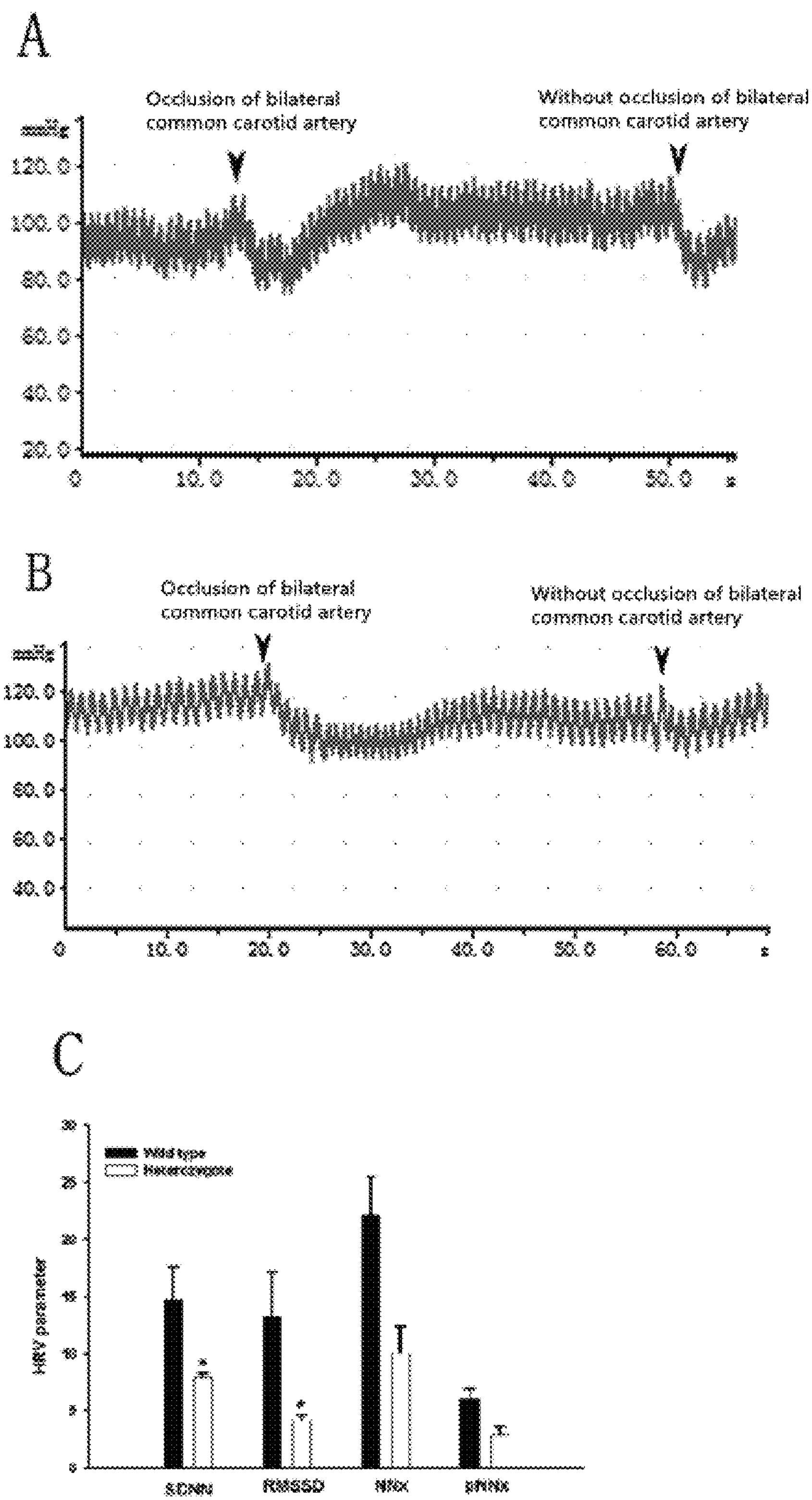
FIG. 14. Detection of blood pressure and heart rate variability in depressure reflex of heterozygous rats with point mutations. A, depressure reflex in wild-type rats; B, depressure reflex in heterozygous rats with a point mutation; C, heart rate variability indicators: SDNN, RMSSD, NNx, pNNx.

Compared with wild-type rats, the depress reflex of heterozygous rats having CACNA1b(K565R) point mutants was not obvious (FIG. 14 panel A and panel B); compared with wild-type rats, the index of heart rate variability of heterozygous rats having CACNA1b(K565R) point mutants was decreased, suggesting the parasympathetic activity was reduced (FIG. 14 panel C).

2.4 Wireless Telemetry Electrocardiogram

Figure 15:
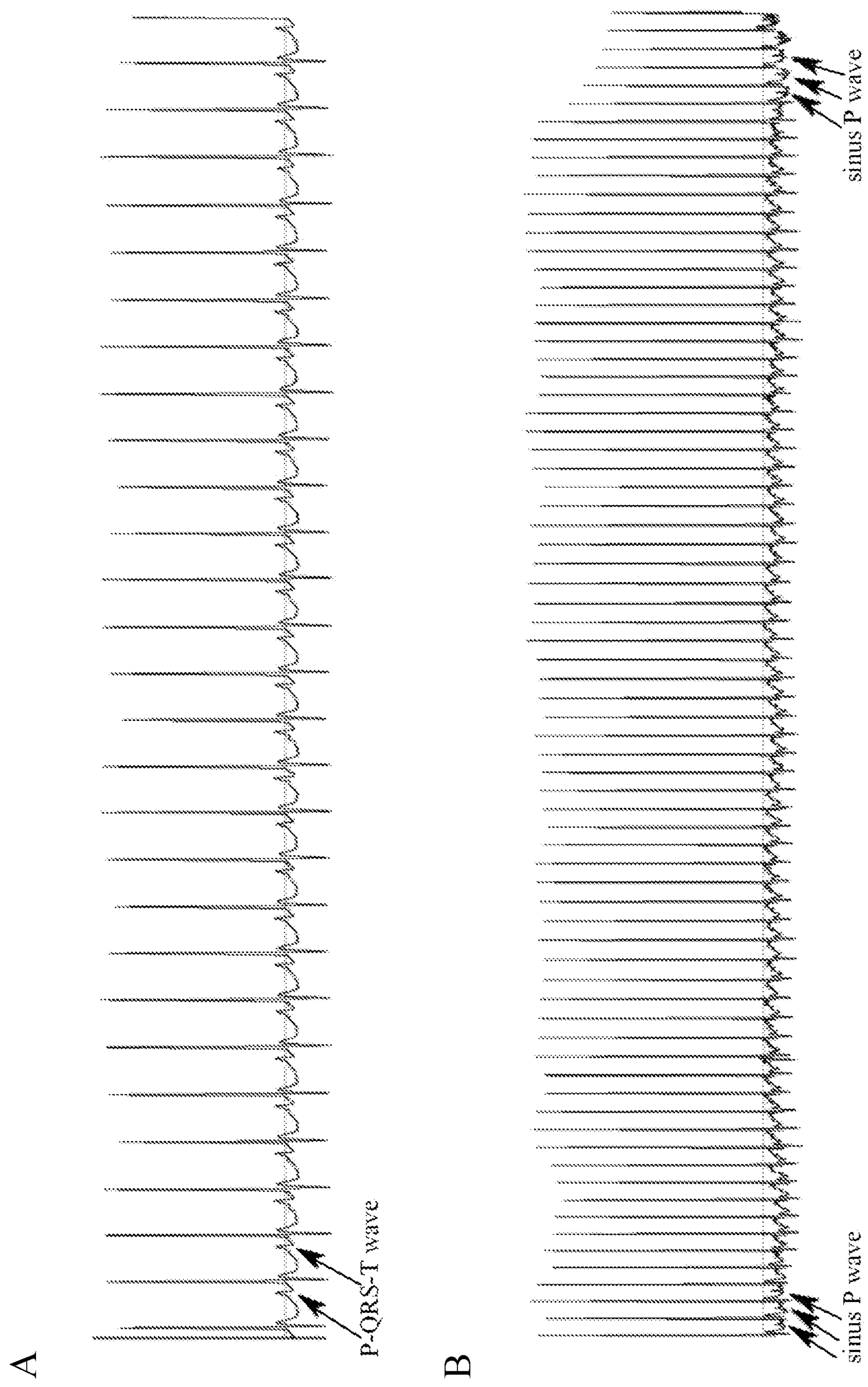
FIG. 15. Wireless telemetry electrocardiography (ECG) in three groups of rats. A, normal ECG of wild-type rats, having regular presence of P-QRS-T wave, 250-450 times/min of frequency, a screen duration of 5 seconds; B, the onset and termination ECG of paroxysmal supraventricular tachycardia (PST) (narrow QRS tachycardia) in mutant heterozygous rats, which present sudden onset and sudden termination, disappearance of sinus P wave during the onset, supraventricular QRS wave, ST-T segment depression, regular heart rate (about 490 beats/min), and after a duration of nearly 10 seconds, which present spontaneous termination, and a sinus P wave (indicated by the arrow), with a screen duration of 9.8 seconds.
Figure 15:
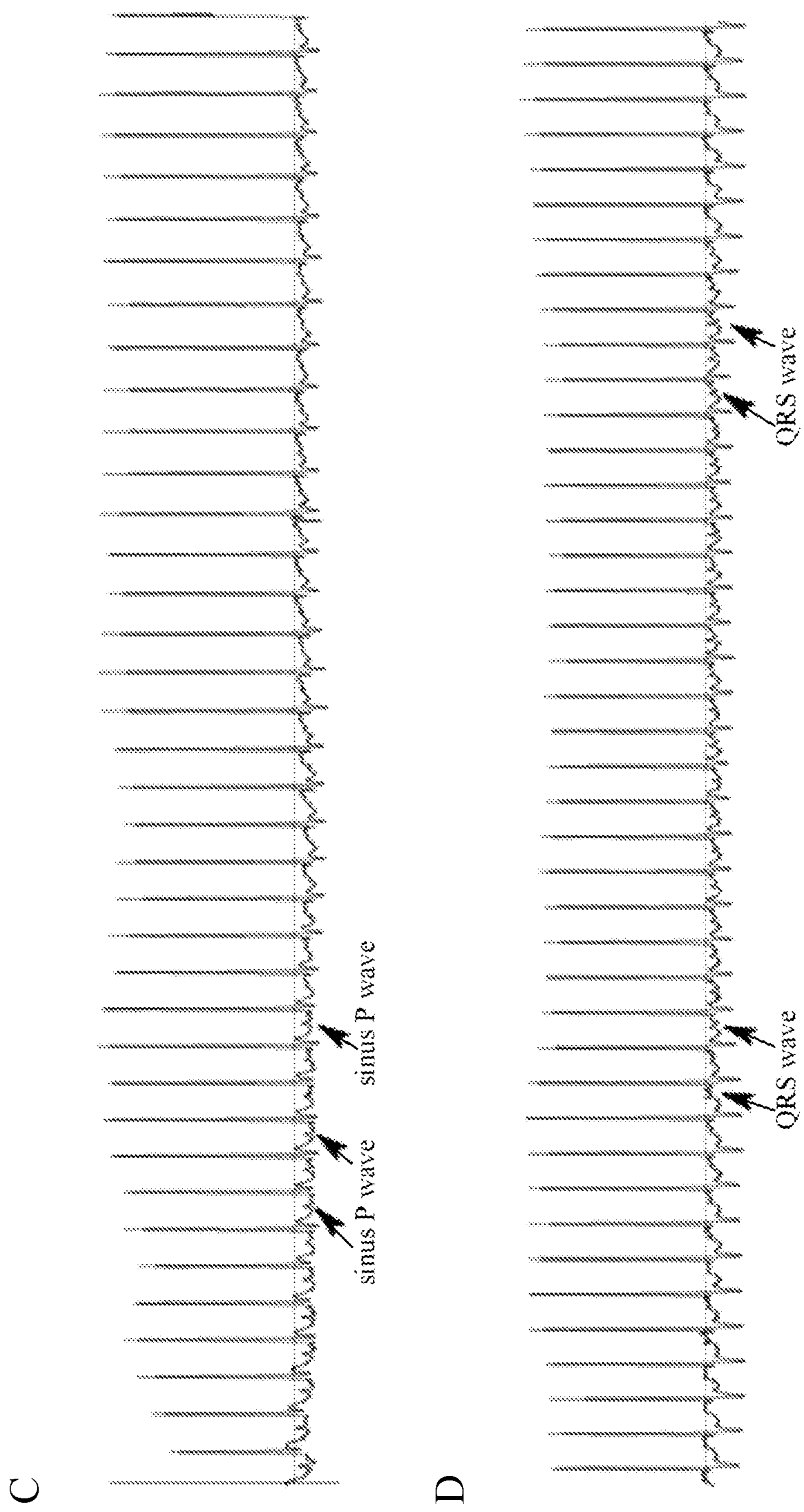

Arrhythmia was detected in a heterozygous rat by wireless telemetry ECG (FIG. 15). The arrow in the figure indicates P wave, and the electrocardiogram was lead II. No P wave was seen in the middle segment of arrhythmia. The amplitude of S wave was increased, which might be "false S wave", and T wave was inverted.

2.5 Intracardiac Electrophysiological Examination

Figure 16:
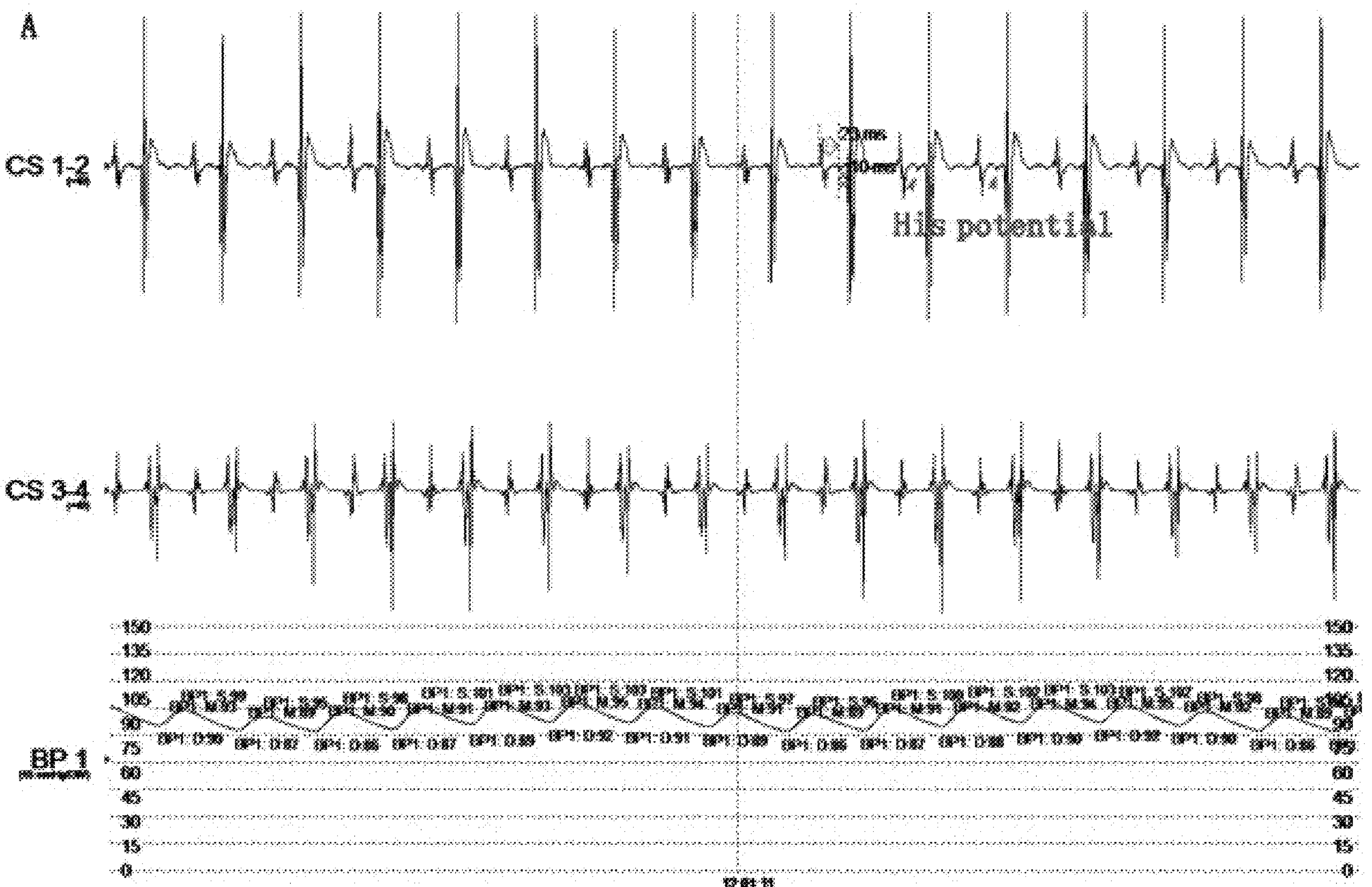
FIG. 16. Intracardiac electrophysiological examination. A, His potential, AH interval and HV interval in normal rats (the arrow showing His potential, 23 ms of AH interval, and 10 ms of HV interval); B, the endocaridal electrogram of wild-type rats stimulated with S1S2,which can clearly record A waves, AH interval and V waves, combined with blood pressure waveforms, because the surface electrocardiogram and the endocaridal electrogram were monitored in real time; C1, C2, S1S2 (AS2, due to more interference, chosing AS2 atrial premature beat instead of S1S2 premature beat stimulation) in homozygous rats with Cacna1b (K565R) point mutation, in which when AS2 interval decreases from 90 ms to 80 ms, AV interval (atrioventricular interval) increases from 70 ms to 100 ms, accompanied by a reversed atrial echo (A wave) in fast-pathway.
Figure 16:
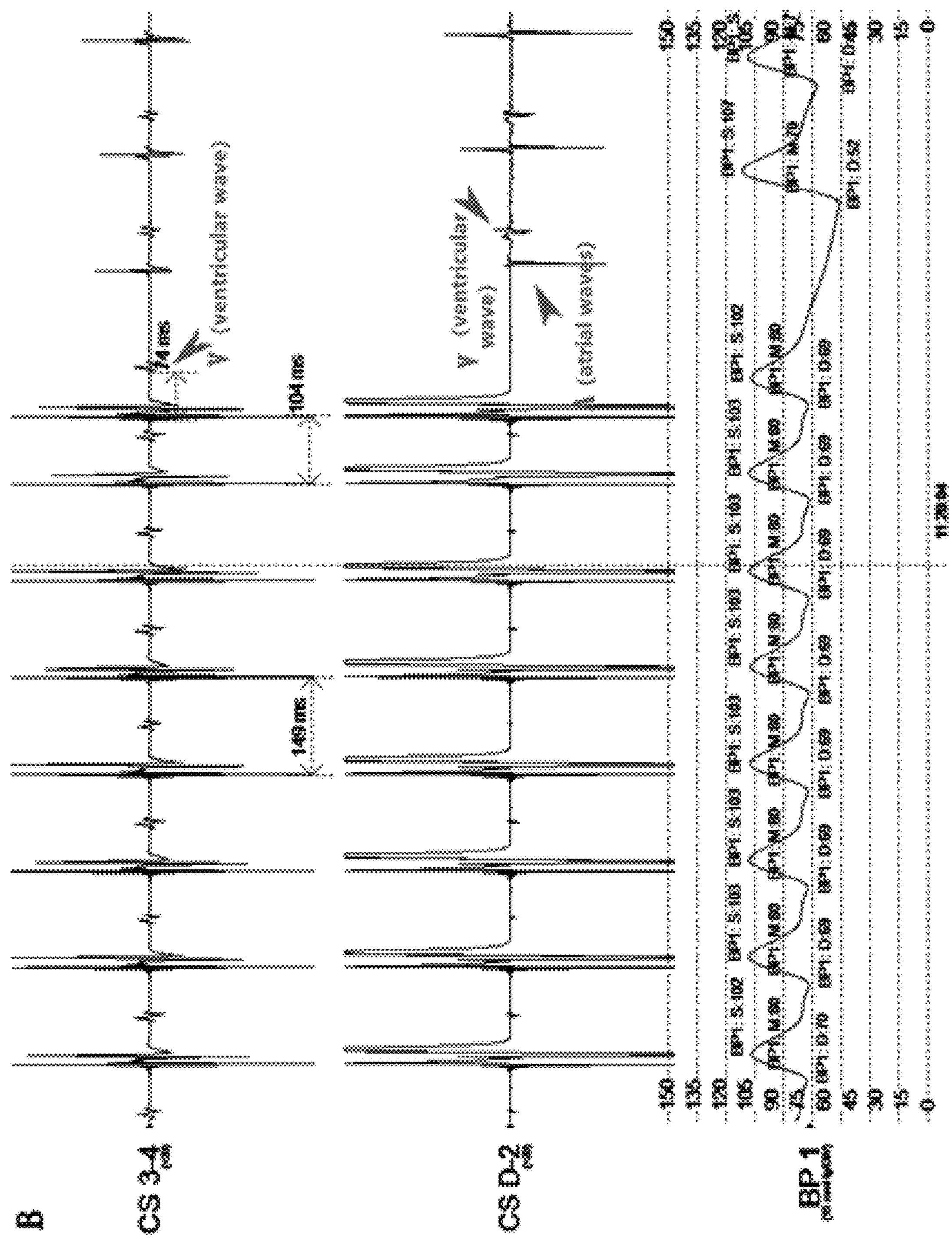
Figure 16:
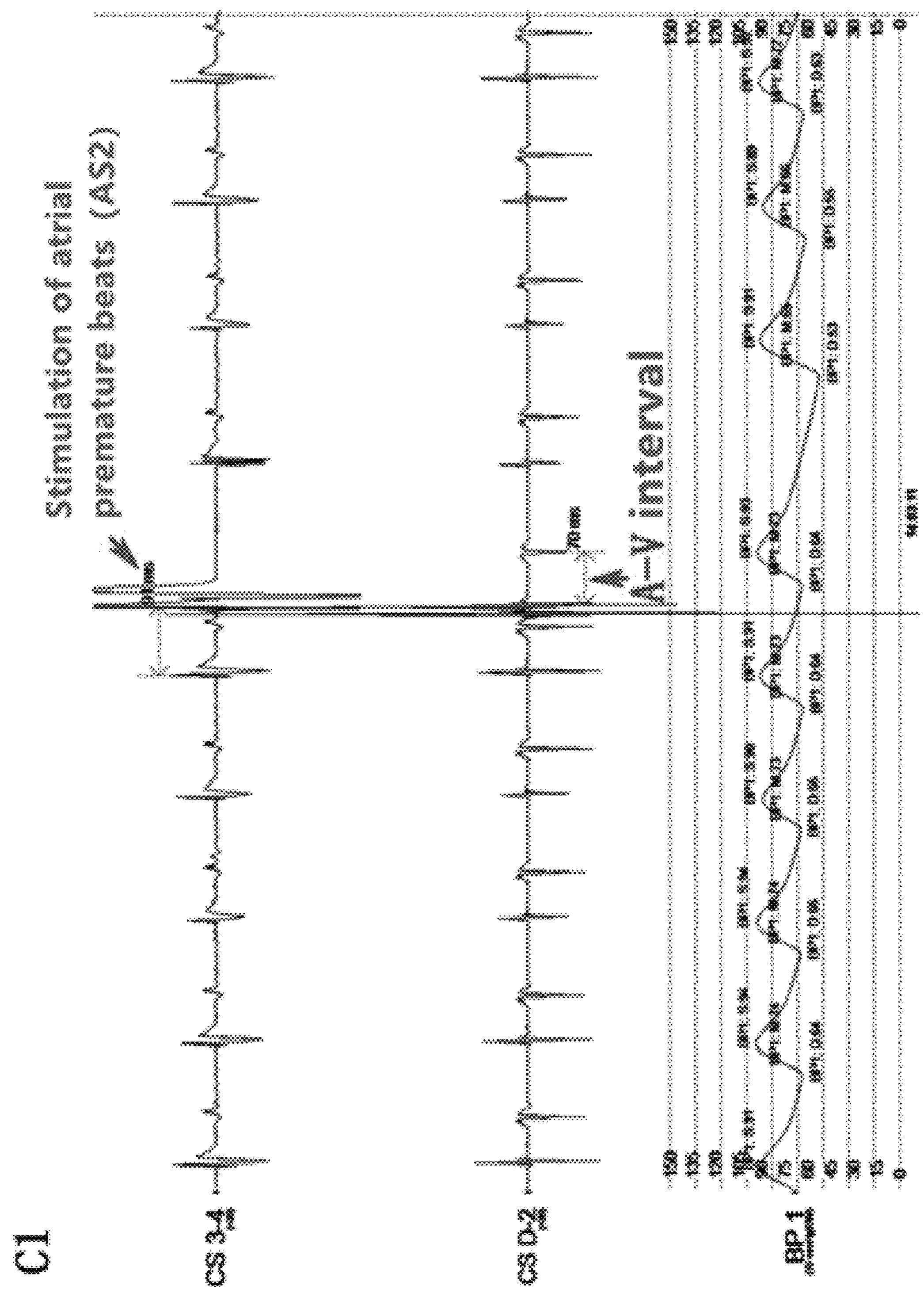
Figure 16:
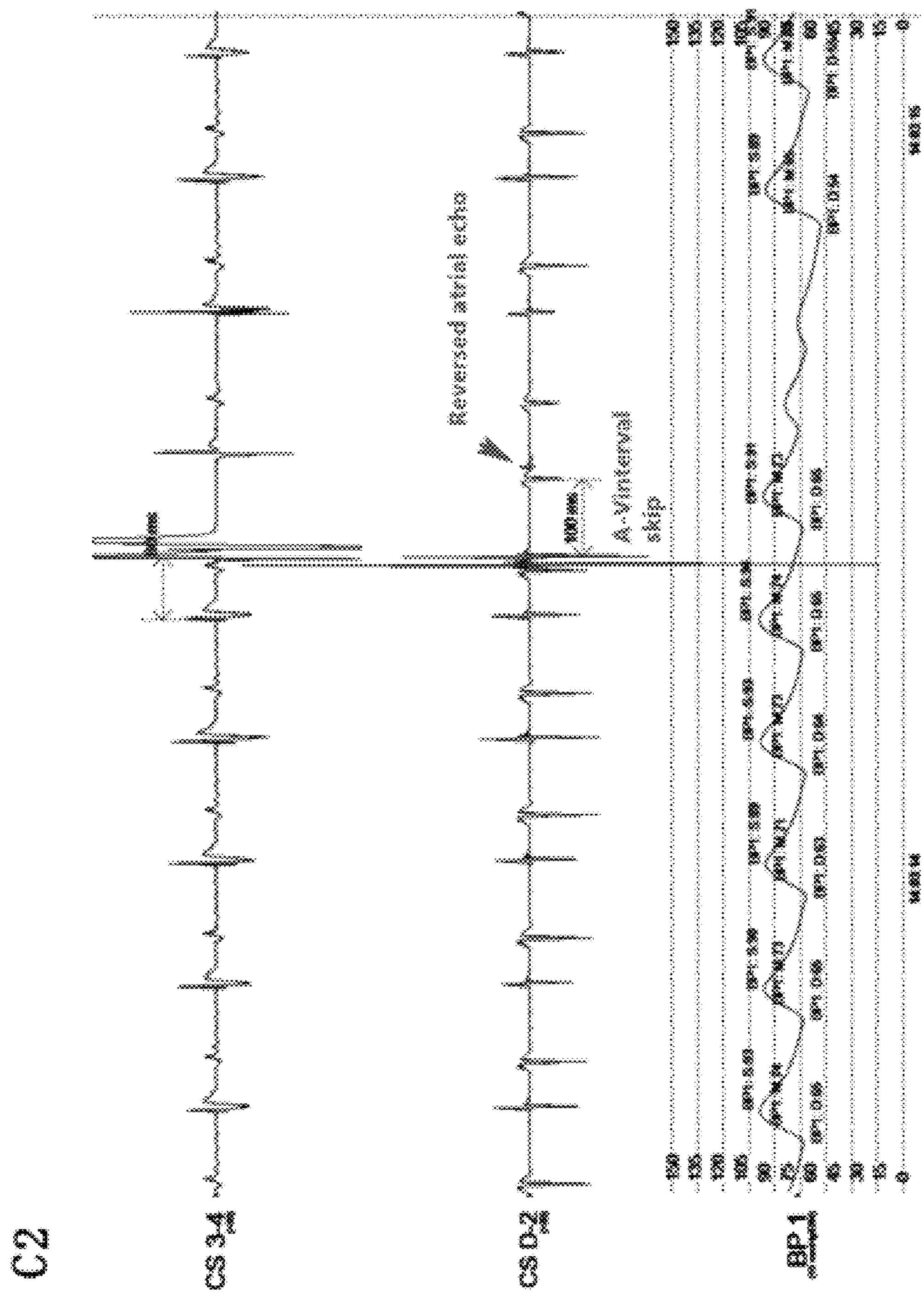

The results indicated that by intracardiac electrophysiologic examination, homozygous rats with point mutations were shown to have multiple double-pathway phenomena and fast-pathway retrograde atrial echoes (FIG. 16), consistent with the characteristics of AVNRT.

The results of this experimental example further confirmed that the human CACNA1B p.K567R mutation could cause paroxysmal tachycardia; CACNA1B c.1700A>G could cause the mutation of CACNA1B p.K567R; therefore, CACNA1B c.1700A>G could also cause paroxysmal tachycardia, which was the clinical feature of AVNRT.

Theoretically, the construction of mutated rats with CACNA1B p.K567R mutations could establish the animal model having increased heart rates, and the mutation was proved to be associated with AVNRT in experimental example 1. Thus, the animal model could be used as the AVNRT model, and used in the development of drugs for the treatment of AVNRT.

In summary, the clinical experiments of the present invention showed that the c.1700A>G or p.K567R mutation of CACNA1B gene was an important genetic factor of AVNRT; the c.1700A>G or p.K567R mutation of CACNA1B gene was related to tachycardia using both zebrafish and rat models. The results were consistent with the results of clinical experiments, further verifying the reliability of clinical experiments. Therefore, the screening kit of the present invention could assist the diagnosis of paroxysmal supraventricular tachycardia (especially AVNRT), was helpful for eugenics, and might guide doctors to treat diseases; it could also provide new clinical therapeutic targets and ideas for the diseases related to autonomic nerves, such as AVNRT and atrial fibrillation, and had excellent clinical application prospect.

| Partial sequence: |
|---|
| 1. CACNA1Bgene CDS (SEQ ID NO: 3):<br>ATGGTCCGCTTCGGGGACGAGCTGGGCGGCCGCTATGGGGGCCCCGGCG<br>GCGGAGAGCGGGCCCGGGGCGGCGGGGCCGGCGGGGCGGGGGGCCCGGG<br>TCCCGGGGGGCTGCAGCCCGGCCAGCGGGTCCTCTACAAGCAATCGATC<br>GCGCAGCGCGCGGACCATGGCGCTGTACAACCCCATCCCGGTCAAGC<br>AGAACTGCTTCACCGTCAACCGCTCGCTCTTCGTCTTCAGCGAGGACAA<br>CGTCGTCCGCAAATACGCGAAGCGCATCACCGAGTGGCCTCCATTCGAG<br>TATATGATCCTGGCCACCATCATCGCCAACTGCATCGTGCTGGCCCTGG<br>AGCAGCACCTCCCTGATGGGGACAAAACGCCCATGTCCGAGCGGCTGGA<br>CGACACGGAGCCCTATTTCATCGGGATCTTTTGCTTCGAGGCAGGGATC<br>AAAATCATCGCTCTGGGCTTTGTCTTCCACAAGGGCTCTTACCTGCGGA<br>ACGGCTGGAACGTCATGGACTTCGTGGTCGTCCTCACAGGGATCCTTGC<br>CACGGCTGGAACTGACTTCGACCTGCGAACACTGAGGGCTGTGCGTGTG<br>CTGAGGCCCCTGAAGCTGGTGTCTGGGATTCCAAGTTTGCAGGTGGTGC<br>TCAAGTCCATCATGAAGGCCATGGTTCCACTCCTGCAGATTGGGCTGCT<br>TCTCTTCTTTGCCATCCTCATGTTTGCCATCATTGGCCTGGAGTTCTAC<br>ATGGGCAAGTTCCACAAGGCCTGTTTCCCCAACAGCACAGATGCGGAGC<br>CCGTGGGTGACTTCCCCTGTGGCAAGGAGGCCCCAGCCCGGCTGTGCGA<br>GGGCGACACTGAGTGCCGGGAGTACTGGCCAGGACCCAACTTTGGCATC<br>ACCAACTTTGACAATATCCTGTTTGCCATCTTGACGGTGTTCCAGTGCA<br>TCACCATGGAGGGCTGGACTGACATCCTCTATAATACAAACGATGCGGC<br>CGGCAACACCTGGAACTGGCTCTACTTCATCCCTCTCATCATCATCGGC<br>TCCTTCTTCATGCTCAACCTGGTGCTGGGCGTGCTCTCGGGGGAGTTTG<br>CCAAGGAGCGAGAGAGGGTGGAGAACCGCCGCGCCTTCCTGAAGCTGCG<br>CCGGCAGCAGCAGATCGAGCGAGAGCTCAACGGGTACCTGGAGTGGATC<br>TTCAAGGCGGAGGAAGTCATGCTGGCCGAGGAGGACAGGAATGCAGAGG<br>AGAAGTCCCCTTTGGACGTGCTGAAGAGAGCGGCCACCAAGAAGAGCAG<br>AAATGACCTGATCCACGCAGAGGAGGGAGAGGACCGGTTTGCAGATCTC<br>TGTGCTGTTGGATCCCCCTTCGCCCGCGCCAGCCTCAAGAGCGGGAAGA<br>CAGAGAGCTCGTCATACTTCCGGAGGAAGGAGAAGATGTTCCGGTTTTT<br>TATCCGGCGCATGGTGAAGGCTCAGAGCTTCTACTGGGTGGTGCTGTGC<br>GTGGTGGCCCTGAACACACTGTGTGTGGCCATGGTGCATTACAACCAGC<br>CGCGGCGGCTTACCACGACCCTGTATTTTGCAGAGTTTGTTTTCCTGGG<br>TCTCTTCCTCACAGAGATGTCCCTGAAGATGTATGGCCTGGGGCCCAGA<br>AGCTACTTCCGGTCCTCCTTCAACTGCTTCGACTTTGGGGTCATCGTGG<br>GGAGCGTCTTTGAAGTGGTCTGGGCGGCCATCAAGCCGGGAAGCTCCTT<br>TGGGATCAGTGTGCTGCGGGCCCTCCGCCTGCTGAGGATCTTCAAAGTC<br>ACGAAGTACTGGAGCTCCCTGCGGAACCTGGTGGTGTCCCTGCTGAACT<br>CCATGAAGTCCATCATCAGCCTGCTCTTCTTGCTCTTCCTGTTCATTGT<br>GGTCTTCGCCCTGCTGGGGATGCAGCTGTTTGGGGGACAGTTCAACTTC<br>CAGGATGAGACTCCCACAACCAACTTCGACACCTTCCCTGCCGCCATCC<br>TCACTGTCTTCCAGATCCTGACGGGAGAGGACTGGAATGCAGTGATGTA<br>TCACGGGATCGAATCGCAAGGCGGCGTCAGCAAAGGCATGTTCTCGTCC<br>TTTTACTTCATTGTCCTGACACTGTTCGGAAACTACACTCTGCTGAATG<br>TCTTTCTGGCCATCGCTGTGGACAACCTGGCCAACGCCCAAGAGCTGAC<br>CAAGGATGAAGAGGAGATGGAAGAAGCAGCCAATCAGAAGCTTGCTCTG<br>CAAAAGGCCAAAGAAGTGGCTGAAGTCAGCCCCATGTCTGCCGCGAACA<br>TCTCCATCGCCGCCAGGCAGCAGAACTCGGCCAAGGCGCGCTCGGTGTG<br>GGAGCAGCGGGCCAGCCAGCTACGGCTGCAGAACCTGCGGGCCAGCTGC<br>GAGGCGCTGTACAGCGAGATGGACCCCGAGGAGCGGCTGCGCTTCGCCA<br>CTACGCGCCACCTGCGGCCCGACATGAAGACGCACCTGGACCGGCCGCT<br>GGTGGTGGAGCTGGGCCGCGACGGCGCGCGGGGGCCCGTGGGAGGCAAA<br>GCCCGACCTGAGGCTGCGGAGGCCCCCGAGGGCGTCGACCCTCCGCGCA<br>GGCACCACCGGCACCGCGACAAGGACAAGACCCCCGCGGCGGGGGACCA<br>GGACCGAGCAGAGGCCCCGAAGGCGGAGAGCGGGGAGCCCGGTGCCCGG<br>GAGGAGCGGCCGCGGCCGCACCGCAGCCACAGCAAGGAGGCCGCGGGGC<br>CCCCGGAGGCGCGGAGCGAGCGCGGCCGAGGCCCAGGCCCCGAGGGCGG<br>CCGGCGGCACCACCGGCGCGGCTCCCCGGAGGAGGCGGCCGAGCGGGAG<br>CCCCGACGCCACCGCGCGCACCGGCACCAGGATCCGAGCAAGGAGTGCG |

-continued

Partial sequence:

CCGGCGCCAAGGGCGAGCGGCGCGCGGCACCGCGGCGGCCCCCGAGC
GGGGCCCCGGGAGGCGGAGAGCGGGGAGGAGCCGGCGCGGCGGCACCGG
GCCCGGCACAAGGCGCAGCCTGCTCACGAGGCTGTGGAGAAGGAGACCA
CGGAGAAGGAGGCCACGGAGAAGGAGGCTGAGATAGTGGAAGCCGACAA
GGAAAAGGAGCTCCGGAACCACCAGCCCCGGGAGCCACACTGTGACCTG
GAGACCAGTGGGACTGTGACTGTGGGTCCCATGCACACACTGCCCAGCA
CCTGTCTCCAGAAGGTGGAGGAACAGCCAGAGGATGCAGACAATCAGCG
GAACGTCACTCGCATGGGCAGTCAGCCCCCAGACCCGAACACTATTGTA
CATATCCCAGTGATGCTGACGGGCCCTCTTGGGGAAGCCACGGTCGTTC
CCAGTGGTAACGTGGACCTGGAAAGCCAAGCAGAGGGGAAGAAGGAGGT
GGAAGCGGATGACGTGATGAGGAGCGGCCCCCGGCCTATCGTCCCATAC
AGCTCCATGTTCTGTTTAAGCCCCACCAACCTGCTCCGCCGCTTCTGCC
ACTACATCGTGACCATGAGGTACTTCGAGGTGGTCATTCTCGTGGTCAT
CGCCTTGAGCAGCATCGCCCTGGCTGCTGAGGACCCAGTGCGCACAGAC
TCGCCCAGGAACAACGCTCTGAAATACCTGGATTACATTTTCACTGGTG
TCTTTACCTTTGAGATGGTGATAAAGATGATCGACTTGGGACTGCTGCT
TCACCCTGGAGCCTATTTCCGGGACTTGTGGAACATTCTGGACTTCATT
GTGGTCAGTGGCGCCCTGGTGGCGTTTGCTTTCTCAGGATCCAAAGGGA
AAGACATCAATACCATCAAGTCTCTGAGAGTCCTTCGTGTCCTGCGGCC
CCTCAAGACCATCAAACGGCTGCCCAAGCTCAAGGCTGTGTTTGACTGT
GTGGTGAACTCCCTGAAGAATGTCCTCAACATCTTGATTGTCTACATGC
TCTTCATGTTCATATTTGCCGTCATTGCGGTGCAGCTCTTCAAAGGGAA
GTTTTTCTACTGCACAGATGAATCCAAGGAGCTGGAGAGGGACTGCAGG
GGTCAGTATTTGGATTATGAGAAGGAGGAAGTGGAAGCTCAGCCCAGGC
AGTGGAAGAAATACGACTTTCACTACGACAATGTGCTCTGGGCTCTGCT
GACGCTGTTCACAGTGTCCACGGGAGAAGGCTGGCCCATGGTGCTGAAA
CACTCCGTGGATGCCACCTATGAGGAGCAGGGTCCAAGCCCTGGGTACC
GCATGGAGCTGTCCATCTTCTACGTGGTCTACTTTGTGGTCTTTCCCTT
CTTCTTCGTCAACATCTTTGTGGCTTTGATCATCATCACCTTCCAGGAG
CAGGGGGACAAGGTGATGTCTGAATGCAGCCTGGAGAAGAACGAGAGGG
CTTGCATTGACTTCGCCATCAGCGCCAAACCCCTGACACGGTACATGCC
CCAAAACCGGCAGTCGTTCCAGTATAAGACGTGGACATTTGTGGTCTCC
CCGCCCTTTGAATACTTCATCATGGCCATGATAGCCCTCAACACTGTGG
TGCTGATGATGAAGTTCTATGATGCACCCTATGAGTACGAGCTGATGCT
GAAATGCCTGAACATCGTGTTCACATCCATGTTCTCCATGGAATGCGTG
CTGAAGATCATCGCCTTTGGGGTGCTGAACTATTTCAGAGATGCCTGGA
ATGTCTTTGACTTTGTCACTGTGTTGGGAAGTATTACTGATATTTTAGT
AACAGAGATTGCGGAAACGAACAATTTCATCAACCTCAGCTTCCTCCGC
CTCTTTCGAGCTGCGCGGCTGATCAAGCTGCTCCGCCAGGGCTACACCA
TCCGCATCCTGCTGTGGACCTTTGTCCAGTCCTTCAAGGCCCTGCCCTA
CGTGTGTCTGCTCATTGCCATGCTGTTCTTCATCTACGCCATCATCGGC
ATGCAGGTGTTTGGGAATATTGCCCTGGATGATGACACCAGCATCAACC
GCCACAACAACTTCCGGACGTTTTTGCAAGCCCTGATGCTGCTGTTCAG
GAGCGCCACGGGGGAGGCCTGGCACGAGATCATGCTGTCCTGCCTGAGC
AACCAGGCCTGTGATGAGCAGGCCAATGCCACCGAGTGTGGAAGTGACT
TTGCCTACTTCTACTTCGTCTCCTTCATCTTCCTGTGCTCCTTTCTGAT
GTTGAACCTCTTTGTGGCTGTGATCATGGACAATTTTGAGTACCTCACG
CGGGACTCTTCCATCCTAGGTCCTCACCACTTGGATGAGTTCATCCGGG
TCTGGGCTGAATACGACCCGGCTGCGTGTGGGCGCATCAGTTACAATGA
CATGTTTGAGATGCTGAAACACATGTCCCCGCCTCTGGGGCTGGGGAAG
AAATGCCCTGCTCGAGTTGCTTACAAGCGCCTGGTTCGCATGAACATGC
CCATCTCCAACGAGGACATGACTGTTCACTTCACGTCCACGCTGATGGC
CCTCATCCGGACGGCACTGGAGATCAAGCTGGCCCCAGCTGGGACAAAG
CAGCATCAGTGTGACGCGGAGTTGAGGAAGGAGATTTCCGTTGTGTGGG
CCAATCTGCCCCAGAAGACTTTGGACTTGCTGGTACCACCCCATAAGCC
TGATGAGATGACAGTGGGGAAGGTTTATGCAGCTCTGATGATATTCGAC
TTCTACAAGCAGAACAAAACCACCAGAGACCAGATGCAGCAGGCTCCTG
GAGGCCTCTCCCAGATGGGTCCTGTGTCCCTGTTCCACCCTCTGAAGGC
CACCCTGGAGCAGACACAGCCGGCTGTGCTCCGAGGAGCCCGGGTTTTC
CTTCGACAGAAGAGTTCCACCTCCCTCAGCAATGGCGGGGCCATACAAA
ACCAAGAGAGTGGCATCAAAGAGTCTGTCTCCTGGGGCACTCAAAGGAC
CCAGGATGCACCCCATGAGGCCAGGCCACCCCTGGAGCGTGGCCACTCC
ACAGAGATCCCTGTGGGGCGGTCAGGAGCACTGGCTGTGGACGTTCAGA
TGCAGAGCATAACCCGGAGGGGCCCTGATGGGGAGCCCCAGCCTGGGCT
GGAGAGCCAGGGTCGAGCGGCCTCCATGCCCCGCCTTGCGGCCGAGACT
CAGCCCGTCACAGATGCCAGCCCCATGAAGCGCTCCATCTCCACGCTGG
CCCAGCGGCCCCGTGGGACTCATCTTTGCAGCACCACCCCGGACCGCCC
ACCCCCTAGCCAGGCGTCGTCGCACCACCACCACCACCGCTGCCACCGC
CGCAGGGACAGGAAGCAGAGGTCCCTGGAGAAGGGGCCCAGCCTGTCTG
CCGATATGGATGGCGCACCAAGCAGTGCTGTGGGGCCGGGGCTGCCCCC
GGGAGAGGGGCCTACAGGCTGCCGGCGGGAACGAGAGCGCCGGCAGGAG
CGGGGCCGGTCCCAGGAGCGGAGGCAGCCCTCATCCTCCTCCTCGGAGA
AGCAGCGCTTCTACTCCTGCGACCGCTTTGGGGGCCGTGAGCCCCCGAA
GCCCAAGCCCTCCCTCAGCAGCCACCCAACGTCGCCAACAGCTGGCCAG
GAGCCGGGACCCCACCCACAGGGCAGTGGTTCCGTGAATGGGAGCCCCT
TGCTGTCAACATCTGGTGCTAGCACCCCCGGCCGCGGTGGGCGGAGGCA
GCTCCCCCAGACGCCCCTGACTCCCCGCCCCAGCATCACCTACAAGACG
GCCAACTCCTCACCCATCCACTTCGCCGGGGCTCAGACCAGCCTCCCTG
CCTTCTCCCCAGGCCGGCTCAGCCGTGGGCTTTCCGAACACAACGCCCT
GCTGCAGAGAGACCCCCTCAGCCAGCCCCTGGCCCCTGGCTCTCGAATT
GGCTCTGACCCTTACCTGGGGCAGCGTCTGGACAGTGAGGCCTCTGTCC
ACGCCCTGCCTGAGGACACTCTCACTTTCGAGGAGGCTGTGGCCACCAA
CTCGGGCCGCTCCTCCAGGACTTCCTACGTGTCCTCCCTGACCTCCCAG
TCTCACCCTCTCCGCCGCGTGCCCAACGGTTACCACTGCACCCTGGGAC
TCAGCTCGGGTGGCCGAGCACGGCACAGCTACCACCACCCTGACCAAGA
CCACTGGTGCTAG

2. Amino acid sequence of CACNA1B(SEQ ID NO: 4)
MVRFGDELGGRYGGPGGGERARGGGAGGAGGPGPGGLQPGQRVLYKQSI
AQRARTMALYNPIPVKQNCFTVNRSLFVFSEDNVVRKYAKRITEWPPFE
YMILATIIANCIVLALEQHLPDGDKTPMSERLDDTEPYFIGIFCFEAGI
KIIALGFVFHKGSYLRNGWNVMDFVVVLTGILATAGTDFDLRTLRAVRV
LRPLKLVSGIPSLQVVLKSIMKAMVPLLQIGLLLFFAILMFAIIGLEFY
MGKFHKACFPNSTDAEPVGDFPCGKEAPARLCEGDTECREYWPGPNFGI
TNFDNILFAILTVFQCITMEGWTDILYNTNDAAGNTWNWLYFIPLIIIG
SFFMLNLVLGVLSGEFAKERERVENRRAFLKLRRQQQIERELNGYLEWI
FKAEEVMLAEEDRNAEEKSPLDVLKRAATKKSRNDLIHAEEGEDRFADL
CAVGSPFARASLKSGKTESSSYFRRKEKMFRFFIRRMVKAQSFYWVVLC
VVALNTLCVAMVHYNQPRRLTTTLYFAEFVFLGLFLTEMSLKMYGLGPR
SYFRSSFNCFDFGVIVGSVFEVVWAAIKPGSSFGISVLRALRLLRIFKV
TKYWSSLRNLVVSLLNSMKSIISLLFLLFLFIVVFALLGMQLFGGQFNF
QDETPTTNFDTFPAAILTVFQILTGEDWNAVMYHGIESQGGVSKGMFSS
FYFIVLTLFGNYTLLNVFLAIAVDNLANAQELTKDEEEMEEAANQKLAL
QKAKEVAEVSPMSAANISIAARQQNSAKARSVWEQRASQLRLQNLRASC
EALYSEMDPEERLRFATTRHLRPDMKTHLDRPLVVELGRDGARGPVGGK
ARPEAAEAPEGVDPPRRHHRHRDKDKTPAAGDQDRAEAPKAESGEPGAR
EERPRPHRSHSKEAAGPPEARSERGRGPGPEGGRRHHRRGSPEEAAERE
PRRHRAHRHQDPSKECAGAKGERRARHRGGPRAGPREAESGEEPARRHR
ARHKAQPAHEAVEKETTEKEATEKEAEIVEADKEKELRNHQPREPHCDL
ETSGTVTVGPMHTLPSTCLQKVEEQPEDADNQRNVTRMGSQPPDPNTIV
HIPVMLTGPLGEATVVPSGNVDLESQAEGKKEVEADDVMRSGPRPIVPY
SSMFCLSPTNLLRRFCHYIVTMRYFEVVILVVIALSSIALAAEDPVRTD
SPRNNALKYLDYIFTGVFTFEMVIKMIDLGLLLHPGAYFRDLWNILDFI
VVSGALVAFAFSGSKGKDINTIKSLRVLRVLRPLKTIKRLPKLKAVFDC
VVNSLKNVLNILIVYMLFMFIFAVIAVQLFKGKFFYCTDESKELERDCR
GQYLDYEKEEVEAQPRQWKKYDFHYDNVLWALLTLFTVSTGEGWPMVLK
HSVDATYEEQGPSPGYRMELSIFYVVYFVVFPFFFVNIFVALIIITFQE
QGDKVMSECSLEKNERACIDFAISAKPLTRYMPQNRQSFQYKTWTFVVS
PPFEYFIMAMIALNTVVLMMKFYDAPYEYELMLKCLNIVFTSMFSMECV
LKIIAFGVLNYFRDAWNVFDFVTVLGSITDILVTEIAETNNFINLSFLR
LFRAARLIKLLRQGYTIRILLWTFVQSFKALPYVCLLIAMLFFIYAIIG
MQVFGNIALDDDTSINRHNNFRTFLQALMLLFRSATGEAWHEIMLSCLS
NQACDEQANATECGSDFAYFYFVSFIFLCSFLMLNLFVAVIMDNFEYLT
RDSSILGPHHLDEFIRVWAEYDPAACGRISYNDMFEMLKHMSPPLGLGK
KCPARVAYKRLVRMNMPISNEDMTVHFTSTLMALIRTALEIKLAPAGTK
QHQCDAELRKEISVVWANLPQKTLDLLVPPHKPDEMTVGKVYAALMIFD
FYKQNKTTRDQMQQAPGGLSQMGPVSLFHPLKATLEQTQPAVLRGARVF
LRQKSSTSLSNGGAIQNQESGIKESVSWGTQRTQDAPHEARPPLERGHS
TEIPVGRSGALAVDVQMQSITRRGPDGEPQPGLESQGRAASMPRLAAET
QPVTDASPMKRSISTLAQRPRGTHLCSTTPDRPPPSQASSHHHHHRCHR
RRDRKQRSLEKGPSLSADMDGAPSSAVGPGLPPGEGPTGCRRERERRQE
RGRSQERRQPSSSSSEKQRFYSCDRFGGREPPKPKPSLSSHPTSPTAGQ
EPGPHPQGSGSVNGSPLLSTSGASTPGRGGRRQLPQTPLTPRPSITYKT
ANSSPIHFAGAQTSLPAFSPGRLSRGLSEHNALLQRDPLSQPLAPGSRI
GSDPYLGQRLDSEASVHALPEDTLTFEEAVATNSGRSSRTSYVSSLTSQ
SHPLRRVPNGYHCTLGLSSGGRARHSYHHPDQDHWC 3. AgeI-CACNA1B(MUT-part)-SalIsequence
(SEQ ID NO: 5):
ACCGGTTTGCAGATCTCTGTGCTGTTGGATCCCCCTTCGCCCGCGCCAG
CCTCAAGAGCGGGAAGACAGAGAGCTCGTCATACTTCCGGAGGAAGGAG
AAGATGTTCCGGTTTTTTATCCGGCGCATGGTGAAGGCTCAGAGCTTCT
ACTGGGTGGTGCTGTGCGTGGTGGCCCTGAACACACTGTGTGTGGCCAT
GGTGCATTACAACCAGCCGCGGCGGCTTACCACGACCCTGTATTTTGCA
GAGTTTGTTTTCCTGGGTCTCTTCCTCACAGAGATGTCCCTGAAGATGT
ATGGCCTGGGGCCCAGAAGCTACTTCCGGTCCTCCTTCAACTGCTTCGA
CTTTGGGGTCATCGTGGGGAGCGTCTTTGAAGTGGTCTGGGCGGCCATC
AGGCCGGGAAGCTCCTTTGGGATCAGTGTGCTGCGGGCCCTCCGCCTGC
TGAGGATCTTCAAAGTCACGAAGTACTGGAGCTCCCTGCGGAACCTGGT
GGTGTCCCTGCTGAACTCCATGAAGTCCATCATCAGCCTGCTCTTCTTG
CTCTTCCTGTTCATTGTGGTCTTCGCCCTGCTGGGGATGCAGCTGTTTG
GGGGACAGTTCAACTTCCAGGATGAGACTCCCACAACCAACTTCGACAC
CTTCCCTGCCGCCATCCTCACTGTCTTCCAGATCCTGACGGGAGAGGAC
TGGAATGCAGTGATGTATCACGGGATCGAATCGCAAGGCGGCGTCAGCA -continued

| Partial sequence: |
|---|
| AAGGCATGTTCTCGTCCTTTTACTTCATTGTCCTGACACTGTTCGGAAA<br>CTACACTCTGCTGAATGTCTTTCTGGCCATCGCTGTGGACAACCTGGCC<br>AACGCCCAAGAGCTGACCAAGGATGAAGAGGAGATGGAAGAAGCAGCCA<br>ATCAGAAGCTTGCTCTGCAAAAGGCCAAAGAAGTGGCTGAAGTCAGCCC<br>CATGTCTGCCGCGAACATCTCCATCGCCGCCAGGCAGCAGAACTCGGCC<br>AAGGCGCGCTCGGTGTGGGAGCAGCGGGCCAGCCAGCTACGGCTGCAGA<br>ACCTGCGGGCCAGCTGCGAGGCGCTGTACAGCGAGATGGACCCCGAGGA |

-continued

| Partial sequence: |
|---|
| GCGGCTGCGCTTCGCCACTACGCGCCACCTGCGGCCCGACATGAAGACG<br>CACCTGGACCGGCCGCTGGTGGTGGAGCTGGGCCGCGACGGCGCGCGGG<br>GGCCCGTGGGAGGCAAAGCCCGACCTGAGGCTGCGGAGGCCCCCGAGGG<br>CGTCGAC |

(Note: the underlined parts at the beginning and the end were the cleavage sites, and the bold and underlined partin the middlewas the codonafter mutation.)

The invention claimed is:

1. A method of assaying the risk of paroxysmal supraventricular tachycardia in a human subject, comprising:

obtaining a sample of genetic material from said human subject;

amplifying a genomic DNA fragment in the sample using a forward primer consisting of a nucleotide sequence represented by SEQ ID NO: 1 and a reverse primer consisting of a nucleotide sequence represented by SEQ ID NO: 2; and assaying the sample and detecting a G nucleotide at the position corresponding to position 1700 of SEQ ID NO: 3, wherein the assaying comprises sequencing, fluorescent quantitative PCR, restriction fragment length polymorphism methods, or a single-strand conformation polymorphism analysis, wherein the presence of the polymorphism indicates said human subject has an increased risk of paroxysmal supraventricular tachycardia.

* * * * *

SEQUENCE LISTING

```
<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: synthesized

<400> SEQUENCE: 1

gatggttcct tacggagagg t                                                21


<210> SEQ ID NO 2
<211> LENGTH: 20
<212> TYPE: DNA
<213> ORGANISM: Artificial Sequence
<220> FEATURE:
<223> OTHER INFORMATION: synthesized

<400> SEQUENCE: 2

aagcaccctg tgtggctgat                                                  20


<210> SEQ ID NO 3
<211> LENGTH: 7020
<212> TYPE: DNA
<213> ORGANISM: Homo sapiens

<400> SEQUENCE: 3

atggtccgct tcggggacga gctgggcggc cgctatgggg gccccggcgg cggagagcgg      60

gcccggggcg gcggggccgg cggggcgggg ggcccgggtc ccggggggct gcagcccggc     120

cagcgggtcc tctacaagca atcgatcgcg cagcgcgcgc ggaccatggc gctgtacaac     180

cccatcccgg tcaagcagaa ctgcttcacc gtcaaccgct cgctcttcgt cttcagcgag     240

gacaacgtcg tccgcaaata cgcgaagcgc atcaccgagt ggcctccatt cgagtatatg     300

atcctggcca ccatcatcgc caactgcatc gtgctggccc tggagcagca cctccctgat     360

ggggacaaaa cgcccatgtc cgagcggctg gacgacacgg agccctattt catcgggatc     420

ttttgcttcg aggcagggat caaaatcatc gctctgggct ttgtcttcca caagggctct     480

tacctgcgga acggctggaa cgtcatggac ttcgtggtcg tcctcacagg gatccttgcc     540

acggctggaa ctgacttcga cctgcgaaca ctgagggctg tgcgtgtgct gaggcccctg     600

aagctggtgt ctgggattcc aagtttgcag gtggtgctca agtccatcat gaaggccatg     660

gttccactcc tgcagattgg gctgcttctc ttctttgcca tcctcatgtt tgccatcatt     720

ggcctggagt tctacatggg caagttccac aaggcctgtt tccccaacag cacagatgcg     780

gagcccgtgg gtgacttccc ctgtggcaag gaggccccag cccggctgtg cgagggcgac     840

actgagtgcc gggagtactg gccaggaccc aactttggca tcaccaactt tgacaatatc     900

ctgtttgcca tcttgacggt gttccagtgc atcaccatgg agggctggac tgacatcctc     960
```

-continued

```
tataatacaa acgatgcggc cggcaacacc tggaactggc tctacttcat ccctctcatc   1020
atcatcggct ccttcttcat gctcaacctg gtgctgggcg tgctctcggg ggagtttgcc   1080
aaggagcgag agagggtgga gaaccgccgc gccttcctga agctgcgccg gcagcagcag   1140
atcgagcgag agctcaacgg gtacctggag tggatcttca aggcggagga agtcatgctg   1200
gccgaggagg acaggaatgc agaggagaag tcccctttgg acgtgctgaa gagagcggcc   1260
accaagaaga gcagaaatga cctgatccac gcagaggagg gagaggaccg gtttgcagat   1320
ctctgtgctg ttggatcccc cttcgcccgc gccagcctca agagcgggaa gacagagagc   1380
tcgtcatact tccggaggaa ggagaagatg ttccggtttt ttatccggcg catggtgaag   1440
gctcagagct tctactgggt ggtgctgtgc gtggtggccc tgaacacact gtgtgtggcc   1500
atggtgcatt acaaccagcc gcggcggctt accacgaccc tgtattttgc agagtttgtt   1560
ttcctgggtc tcttcctcac agagatgtcc ctgaagatgt atggcctggg gcccagaagc   1620
tacttccggt cctccttcaa ctgcttcgac tttggggtca tcgtggggag cgtctttgaa   1680
gtggtctggg cggccatcaa gccgggaagc tcctttggga tcagtgtgct gcgggccctc   1740
cgcctgctga ggatcttcaa agtcacgaag tactggagct ccctgcggaa cctggtggtg   1800
tccctgctga actccatgaa gtccatcatc agcctgctct tcttgctctt cctgttcatt   1860
gtggtcttcg ccctgctggg gatgcagctg tttgggggac agttcaactt ccaggatgag   1920
actcccacaa ccaacttcga caccttccct gccgccatcc tcactgtctt ccagatcctg   1980
acgggagagg actggaatgc agtgatgtat cacgggatcg aatcgcaagg cggcgtcagc   2040
aaaggcatgt tctcgtcctt ttacttcatt gtcctgacac tgttcggaaa ctacactctg   2100
ctgaatgtct ttctggccat cgctgtggac aacctggcca acgcccaaga gctgaccaag   2160
gatgaagagg agatggaaga agcagccaat cagaagcttg ctctgcaaaa ggccaaagaa   2220
gtggctgaag tcagccccat gtctgccgcg aacatctcca tcgccgccag gcagcagaac   2280
tcggccaagg cgcgctcggt gtgggagcag cgggccagcc agctacggct gcagaacctg   2340
cgggccagct gcgaggcgct gtacagcgag atggaccccg aggagcggct gcgcttcgcc   2400
actacgcgcc acctgcggcc cgacatgaag acgcacctgg accggccgct ggtggtggag   2460
ctgggccgcg acggcgcgcg ggggcccgtg ggaggcaaag cccgacctga ggctgcggag   2520
gcccccgagg gcgtcgaccc tccgcgcagg caccaccggc accgcgacaa ggacaagacc   2580
cccgcggcgg gggaccagga ccgagcagag gccccgaagg cggagagcgg ggagcccggt   2640
gcccgggagg agcggccgcg gccgcaccgc agccacagca aggaggccgc ggggcccccg   2700
gaggcgcgga gcgagcgcgg ccgaggccca ggccccgagg gcggccggcg gcaccaccgg   2760
cgcggctccc cggaggaggc ggccgagcgg gagccccgac gccaccgcgc gcaccggcac   2820
caggatccga gcaaggagtg cgccggcgcc aagggcgagc ggcgcgcgcg gcaccgcggc   2880
ggccccgag cggggccccg ggaggcggag agcggggagg agccggcgcg gcggcaccgg    2940
gcccggcaca aggcgcagcc tgctcacgag gctgtggaga aggagaccac ggagaaggag   3000
gccacggaga aggaggctga gatagtggaa gccgacaagg aaaaggagct ccggaaccac   3060
cagccccggg agccacactg tgacctggag accagtggga ctgtgactgt gggtcccatg   3120
cacacactgc ccagcacctg tctccagaag gtggaggaac agccagagga tgcagacaat   3180
cagcggaacg tcactcgcat gggcagtcag cccccagacc cgaacactat tgtacatatc   3240
ccagtgatgc tgacgggccc tcttggggaa gccacggtcg ttcccagtgg taacgtggac   3300
```

-continued ctggaaagcc aagcagaggg gaagaaggag gtggaagcgg atgacgtgat gaggagcggc 3360
ccccggccta tcgtcccata cagctccatg ttctgtttaa gccccaccaa cctgctccgc 3420
cgcttctgcc actacatcgt gaccatgagg tacttcgagg tggtcattct cgtggtcatc 3480
gccttgagca gcatcgccct ggctgctgag gacccagtgc gcacagactc gcccaggaac 3540
aacgctctga aatacctgga ttacattttc actggtgtct ttacctttga gatggtgata 3600
aagatgatcg acttgggact gctgcttcac cctggagcct atttccggga cttgtggaac 3660
attctggact tcattgtggt cagtggcgcc ctggtggcgt ttgctttctc aggatccaaa 3720
gggaaagaca tcaataccat caagtctctg agagtccttc gtgtcctgcg gcccctcaag 3780
accatcaaac ggctgcccaa gctcaaggct gtgtttgact gtgtggtgaa ctccctgaag 3840
aatgtcctca acatcttgat tgtctacatg ctcttcatgt tcatatttgc cgtcattgcg 3900
gtgcagctct tcaaagggaa gtttttctac tgcacagatg aatccaagga gctggagagg 3960
gactgcaggg gtcagtattt ggattatgag aaggaggaag tggaagctca gcccaggcag 4020
tggaagaaat acgactttca ctacgacaat gtgctctggg ctctgctgac gctgttcaca 4080
gtgtccacgg gagaaggctg gcccatggtg ctgaaacact ccgtggatgc cacctatgag 4140
gagcagggtc caagccctgg gtaccgcatg gagctgtcca tcttctacgt ggtctacttt 4200
gtggtctttc ccttcttctt cgtcaacatc tttgtggctt tgatcatcat caccttccag 4260
gagcaggggg acaaggtgat gtctgaatgc agcctggaga agaacgagag ggcttgcatt 4320
gacttcgcca tcagcgccaa acccctgaca cggtacatgc cccaaaaccg gcagtcgttc 4380
cagtataaga cgtggacatt tgtggtctcc ccgccctttg aatacttcat catggccatg 4440
atagccctca acactgtggt gctgatgatg aagttctatg atgcacccta tgagtacgag 4500
ctgatgctga aatgcctgaa catcgtgttc acatccatgt tctccatgga atgcgtgctg 4560
aagatcatcg cctttggggt gctgaactat ttcagagatg cctggaatgt ctttgacttt 4620
gtcactgtgt tgggaagtat tactgatatt ttagtaacag agattgcgga aacgaacaat 4680
ttcatcaacc tcagcttcct ccgcctcttt cgagctgcgc ggctgatcaa gctgctccgc 4740
cagggctaca ccatccgcat cctgctgtgg acctttgtcc agtccttcaa ggccctgccc 4800
tacgtgtgtc tgctcattgc catgctgttc ttcatctacg ccatcatcgg catgcaggtg 4860
tttgggaata ttgccctgga tgatgacacc agcatcaacc gccacaacaa cttccggacg 4920
tttttgcaag ccctgatgct gctgttcagg agcgccacgg gggaggcctg gcacgagatc 4980
atgctgtcct gcctgagcaa ccaggcctgt gatgagcagg ccaatgccac cgagtgtgga 5040
agtgactttg cctacttcta cttcgtctcc ttcatcttcc tgtgctcctt tctgatgttg 5100
aacctctttg tggctgtgat catggacaat tttgagtacc tcacgcggga ctcttccatc 5160
ctaggtcctc accacttgga tgagttcatc cgggtctggg ctgaatacga cccggctgcg 5220
tgtgggcgca tcagttacaa tgacatgttt gagatgctga aacacatgtc cccgcctctg 5280
gggctgggga agaaatgccc tgctcgagtt gcttacaagc gcctggttcg catgaacatg 5340
cccatctcca acgaggacat gactgttcac ttcacgtcca cgctgatggc cctcatccgg 5400
acggcactgg agatcaagct ggccccagct gggacaaagc agcatcagtg tgacgcggag 5460
ttgaggaagg agatttccgt tgtgtgggcc aatctgcccc agaagacttt ggacttgctg 5520
gtaccacccc ataagcctga tgagatgaca gtggggaagg tttatgcagc tctgatgata 5580
ttcgacttct acaagcagaa caaaaccacc agagaccaga tgcagcaggc tcctggaggc 5640
ctctcccaga tgggtcctgt gtccctgttc caccctctga aggccaccct ggagcagaca 5700

```
cagccggctg tgctccgagg agcccgggtt ttccttcgac agaagagttc cacctccctc   5760

agcaatggcg gggccataca aaaccaagag agtggcatca aagagtctgt ctcctggggc   5820

actcaaagga cccaggatgc accccatgag gccaggccac ccctggagcg tggccactcc   5880

acagagatcc ctgtggggcg gtcaggagca ctggctgtgg acgttcagat gcagagcata   5940

acccggaggg gccctgatgg ggagccccag cctgggctgg agagccaggg tcgagcggcc   6000

tccatgcccc gccttgcggc cgagactcag cccgtcacag atgccagccc catgaagcgc   6060

tccatctcca cgctggccca gcggccccgt gggactcatc tttgcagcac caccccggac   6120

cgcccacccc ctagccaggc gtcgtcgcac caccaccacc accgctgcca ccgccgcagg   6180

gacaggaagc agaggtccct ggagaagggg cccagcctgt ctgccgatat ggatggcgca   6240

ccaagcagtg ctgtggggcc ggggctgccc ccgggagagg ggcctacagg ctgccggcgg   6300

gaacgagagc gccggcagga gcggggccgg tcccaggagc ggaggcagcc ctcatcctcc   6360

tcctcggaga agcagcgctt ctactcctgc gaccgctttg gggcccgtga gccccccgaag   6420

cccaagccct ccctcagcag ccacccaacg tcgccaacag ctggccagga gccgggaccc   6480

cacccacagg gcagtggttc cgtgaatggg agccccttgc tgtcaacatc tggtgctagc   6540

acccccggcc gcggtgggcg gaggcagctc ccccagacgc ccctgactcc ccgccccagc   6600

atcacctaca agacggccaa ctcctcaccc atccacttcg ccggggctca gaccagcctc   6660

cctgccttct ccccaggccg gctcagccgt gggctttccg aacacaacgc cctgctgcag   6720

agagaccccc tcagccagcc cctggcccct ggctctcgaa ttggctctga cccttacctg   6780

gggcagcgtc tggacagtga ggcctctgtc cacgccctgc ctgaggacac tctcactttc   6840

gaggaggctg tggccaccaa ctcgggccgc tcctccagga cttcctacgt gtcctccctg   6900

acctcccagt ctcaccctct ccgccgcgtg cccaacggtt accactgcac cctgggactc   6960

agctcgggtg gccgagcacg gcacagctac caccaccctg accaagacca ctggtgctag   7020
```

<210> SEQ ID NO 4
<211> LENGTH: 2339
<212> TYPE: PRT
<213> ORGANISM: Homo sapiens

<400> SEQUENCE: 4

```
Met Val Arg Phe Gly Asp Glu Leu Gly Gly Arg Tyr Gly Gly Pro Gly
1               5                   10                  15

Gly Gly Glu Arg Ala Arg Gly Gly Gly Ala Gly Gly Ala Gly Gly Pro
            20                  25                  30

Gly Pro Gly Gly Leu Gln Pro Gly Gln Arg Val Leu Tyr Lys Gln Ser
        35                  40                  45

Ile Ala Gln Arg Ala Arg Thr Met Ala Leu Tyr Asn Pro Ile Pro Val
    50                  55                  60

Lys Gln Asn Cys Phe Thr Val Asn Arg Ser Leu Phe Val Phe Ser Glu
65                  70                  75                  80

Asp Asn Val Val Arg Lys Tyr Ala Lys Arg Ile Thr Glu Trp Pro Pro
                85                  90                  95

Phe Glu Tyr Met Ile Leu Ala Thr Ile Ile Ala Asn Cys Ile Val Leu
            100                 105                 110

Ala Leu Glu Gln His Leu Pro Asp Gly Asp Lys Thr Pro Met Ser Glu
        115                 120                 125

Arg Leu Asp Asp Thr Glu Pro Tyr Phe Ile Gly Ile Phe Cys Phe Glu
    130                 135                 140
```

```
Ala Gly Ile Lys Ile Ile Ala Leu Gly Phe Val Phe His Lys Gly Ser
145                 150                 155                 160

Tyr Leu Arg Asn Gly Trp Asn Val Met Asp Phe Val Val Val Leu Thr
                165                 170                 175

Gly Ile Leu Ala Thr Ala Gly Thr Asp Phe Asp Leu Arg Thr Leu Arg
            180                 185                 190

Ala Val Arg Val Leu Arg Pro Leu Lys Leu Val Ser Gly Ile Pro Ser
        195                 200                 205

Leu Gln Val Val Leu Lys Ser Ile Met Lys Ala Met Val Pro Leu Leu
    210                 215                 220

Gln Ile Gly Leu Leu Leu Phe Phe Ala Ile Leu Met Phe Ala Ile Ile
225                 230                 235                 240

Gly Leu Glu Phe Tyr Met Gly Lys Phe His Lys Ala Cys Phe Pro Asn
                245                 250                 255

Ser Thr Asp Ala Glu Pro Val Gly Asp Phe Pro Cys Gly Lys Glu Ala
            260                 265                 270

Pro Ala Arg Leu Cys Glu Gly Asp Thr Glu Cys Arg Glu Tyr Trp Pro
        275                 280                 285

Gly Pro Asn Phe Gly Ile Thr Asn Phe Asp Asn Ile Leu Phe Ala Ile
    290                 295                 300

Leu Thr Val Phe Gln Cys Ile Thr Met Glu Gly Trp Thr Asp Ile Leu
305                 310                 315                 320

Tyr Asn Thr Asn Asp Ala Ala Gly Asn Thr Trp Asn Trp Leu Tyr Phe
                325                 330                 335

Ile Pro Leu Ile Ile Ile Gly Ser Phe Phe Met Leu Asn Leu Val Leu
            340                 345                 350

Gly Val Leu Ser Gly Glu Phe Ala Lys Glu Arg Glu Arg Val Glu Asn
        355                 360                 365

Arg Arg Ala Phe Leu Lys Leu Arg Arg Gln Gln Gln Ile Glu Arg Glu
    370                 375                 380

Leu Asn Gly Tyr Leu Glu Trp Ile Phe Lys Ala Glu Glu Val Met Leu
385                 390                 395                 400

Ala Glu Glu Asp Arg Asn Ala Glu Glu Lys Ser Pro Leu Asp Val Leu
                405                 410                 415

Lys Arg Ala Ala Thr Lys Lys Ser Arg Asn Asp Leu Ile His Ala Glu
            420                 425                 430

Glu Gly Glu Asp Arg Phe Ala Asp Leu Cys Ala Val Gly Ser Pro Phe
        435                 440                 445

Ala Arg Ala Ser Leu Lys Ser Gly Lys Thr Glu Ser Ser Ser Tyr Phe
    450                 455                 460

Arg Arg Lys Glu Lys Met Phe Arg Phe Phe Ile Arg Arg Met Val Lys
465                 470                 475                 480

Ala Gln Ser Phe Tyr Trp Val Val Leu Cys Val Val Ala Leu Asn Thr
                485                 490                 495

Leu Cys Val Ala Met Val His Tyr Asn Gln Pro Arg Arg Leu Thr Thr
            500                 505                 510

Thr Leu Tyr Phe Ala Glu Phe Val Phe Leu Gly Leu Phe Leu Thr Glu
        515                 520                 525

Met Ser Leu Lys Met Tyr Gly Leu Gly Pro Arg Ser Tyr Phe Arg Ser
    530                 535                 540

Ser Phe Asn Cys Phe Asp Phe Gly Val Ile Val Gly Ser Val Phe Glu
545                 550                 555                 560
```

-continued

```
Val Val Trp Ala Ala Ile Lys Pro Gly Ser Ser Phe Gly Ile Ser Val
                565                 570                 575

Leu Arg Ala Leu Arg Leu Leu Arg Ile Phe Lys Val Thr Lys Tyr Trp
            580                 585                 590

Ser Ser Leu Arg Asn Leu Val Val Ser Leu Leu Asn Ser Met Lys Ser
        595                 600                 605

Ile Ile Ser Leu Leu Phe Leu Leu Phe Leu Phe Ile Val Val Phe Ala
    610                 615                 620

Leu Leu Gly Met Gln Leu Phe Gly Gly Gln Phe Asn Phe Gln Asp Glu
625                 630                 635                 640

Thr Pro Thr Thr Asn Phe Asp Thr Phe Pro Ala Ala Ile Leu Thr Val
                645                 650                 655

Phe Gln Ile Leu Thr Gly Glu Asp Trp Asn Ala Val Met Tyr His Gly
            660                 665                 670

Ile Glu Ser Gln Gly Gly Val Ser Lys Gly Met Phe Ser Ser Phe Tyr
        675                 680                 685

Phe Ile Val Leu Thr Leu Phe Gly Asn Tyr Thr Leu Leu Asn Val Phe
    690                 695                 700

Leu Ala Ile Ala Val Asp Asn Leu Ala Asn Ala Gln Glu Leu Thr Lys
705                 710                 715                 720

Asp Glu Glu Glu Met Glu Glu Ala Ala Asn Gln Lys Leu Ala Leu Gln
                725                 730                 735

Lys Ala Lys Glu Val Ala Glu Val Ser Pro Met Ser Ala Ala Asn Ile
            740                 745                 750

Ser Ile Ala Ala Arg Gln Gln Asn Ser Ala Lys Ala Arg Ser Val Trp
        755                 760                 765

Glu Gln Arg Ala Ser Gln Leu Arg Leu Gln Asn Leu Arg Ala Ser Cys
    770                 775                 780

Glu Ala Leu Tyr Ser Glu Met Asp Pro Glu Glu Arg Leu Arg Phe Ala
785                 790                 795                 800

Thr Thr Arg His Leu Arg Pro Asp Met Lys Thr His Leu Asp Arg Pro
                805                 810                 815

Leu Val Val Glu Leu Gly Arg Asp Gly Ala Arg Gly Pro Val Gly Gly
            820                 825                 830

Lys Ala Arg Pro Glu Ala Ala Glu Ala Pro Glu Gly Val Asp Pro Pro
        835                 840                 845

Arg Arg His His Arg His Arg Asp Lys Asp Lys Thr Pro Ala Ala Gly
    850                 855                 860

Asp Gln Asp Arg Ala Glu Ala Pro Lys Ala Glu Ser Gly Glu Pro Gly
865                 870                 875                 880

Ala Arg Glu Glu Arg Pro Arg Pro His Arg Ser His Ser Lys Glu Ala
                885                 890                 895

Ala Gly Pro Pro Glu Ala Arg Ser Glu Arg Gly Arg Gly Pro Gly Pro
            900                 905                 910

Glu Gly Gly Arg Arg His His Arg Arg Gly Ser Pro Glu Glu Ala Ala
        915                 920                 925

Glu Arg Glu Pro Arg Arg His Arg Ala His Arg His Gln Asp Pro Ser
    930                 935                 940

Lys Glu Cys Ala Gly Ala Lys Gly Glu Arg Arg Ala Arg His Arg Gly
945                 950                 955                 960

Gly Pro Arg Ala Gly Pro Arg Glu Ala Glu Ser Gly Glu Glu Pro Ala
                965                 970                 975

Arg Arg His Arg Ala Arg His Lys Ala Gln Pro Ala His Glu Ala Val
```

```
            980                 985                 990

Glu Lys Glu Thr Thr Glu Lys Glu  Ala Thr Glu Lys Glu  Ala Glu Ile
        995                 1000                1005

Val Glu  Ala Asp Lys Glu Lys  Glu Leu Arg Asn His  Gln Pro Arg
    1010                 1015                 1020

Glu Pro  His Cys Asp Leu Glu  Thr Ser Gly Thr Val  Thr Val Gly
    1025                 1030                 1035

Pro Met  His Thr Leu Pro Ser  Thr Cys Leu Gln Lys  Val Glu Glu
    1040                 1045                 1050

Gln Pro  Glu Asp Ala Asp Asn  Gln Arg Asn Val Thr  Arg Met Gly
    1055                 1060                 1065

Ser Gln  Pro Pro Asp Pro Asn  Thr Ile Val His Ile  Pro Val Met
    1070                 1075                 1080

Leu Thr  Gly Pro Leu Gly Glu  Ala Thr Val Val Pro  Ser Gly Asn
    1085                 1090                 1095

Val Asp  Leu Glu Ser Gln Ala  Glu Gly Lys Lys Glu  Val Glu Ala
    1100                 1105                 1110

Asp Asp  Val Met Arg Ser Gly  Pro Arg Pro Ile Val  Pro Tyr Ser
    1115                 1120                 1125

Ser Met  Phe Cys Leu Ser Pro  Thr Asn Leu Leu Arg  Arg Phe Cys
    1130                 1135                 1140

His Tyr  Ile Val Thr Met Arg  Tyr Phe Glu Val Val  Ile Leu Val
    1145                 1150                 1155

Val Ile  Ala Leu Ser Ser Ile  Ala Leu Ala Ala Glu  Asp Pro Val
    1160                 1165                 1170

Arg Thr  Asp Ser Pro Arg Asn  Asn Ala Leu Lys Tyr  Leu Asp Tyr
    1175                 1180                 1185

Ile Phe  Thr Gly Val Phe Thr  Phe Glu Met Val Ile  Lys Met Ile
    1190                 1195                 1200

Asp Leu  Gly Leu Leu Leu His  Pro Gly Ala Tyr Phe  Arg Asp Leu
    1205                 1210                 1215

Trp Asn  Ile Leu Asp Phe Ile  Val Val Ser Gly Ala  Leu Val Ala
    1220                 1225                 1230

Phe Ala  Phe Ser Gly Ser Lys  Gly Lys Asp Ile Asn  Thr Ile Lys
    1235                 1240                 1245

Ser Leu  Arg Val Leu Arg Val  Leu Arg Pro Leu Lys  Thr Ile Lys
    1250                 1255                 1260

Arg Leu  Pro Lys Leu Lys Ala  Val Phe Asp Cys Val  Val Asn Ser
    1265                 1270                 1275

Leu Lys  Asn Val Leu Asn Ile  Leu Ile Val Tyr Met  Leu Phe Met
    1280                 1285                 1290

Phe Ile  Phe Ala Val Ile Ala  Val Gln Leu Phe Lys  Gly Lys Phe
    1295                 1300                 1305

Phe Tyr  Cys Thr Asp Glu Ser  Lys Glu Leu Glu Arg  Asp Cys Arg
    1310                 1315                 1320

Gly Gln  Tyr Leu Asp Tyr Glu  Lys Glu Glu Val Glu  Ala Gln Pro
    1325                 1330                 1335

Arg Gln  Trp Lys Lys Tyr Asp  Phe His Tyr Asp Asn  Val Leu Trp
    1340                 1345                 1350

Ala Leu  Leu Thr Leu Phe Thr  Val Ser Thr Gly Glu  Gly Trp Pro
    1355                 1360                 1365

Met Val  Leu Lys His Ser Val  Asp Ala Thr Tyr Glu  Glu Gln Gly
    1370                 1375                 1380
```

-continued

```
Pro Ser  Pro Gly Tyr Arg Met  Glu Leu Ser Ile Phe  Tyr Val Val
    1385                 1390                 1395

Tyr Phe  Val Val Phe Pro Phe  Phe Phe Val Asn Ile  Phe Val Ala
    1400                 1405                 1410

Leu Ile  Ile Ile Thr Phe Gln  Glu Gln Gly Asp Lys  Val Met Ser
    1415                 1420                 1425

Glu Cys  Ser Leu Glu Lys Asn  Glu Arg Ala Cys Ile  Asp Phe Ala
    1430                 1435                 1440

Ile Ser  Ala Lys Pro Leu Thr  Arg Tyr Met Pro Gln  Asn Arg Gln
    1445                 1450                 1455

Ser Phe  Gln Tyr Lys Thr Trp  Thr Phe Val Val Ser  Pro Pro Phe
    1460                 1465                 1470

Glu Tyr  Phe Ile Met Ala Met  Ile Ala Leu Asn Thr  Val Val Leu
    1475                 1480                 1485

Met Met  Lys Phe Tyr Asp Ala  Pro Tyr Glu Tyr Glu  Leu Met Leu
    1490                 1495                 1500

Lys Cys  Leu Asn Ile Val Phe  Thr Ser Met Phe Ser  Met Glu Cys
    1505                 1510                 1515

Val Leu  Lys Ile Ile Ala Phe  Gly Val Leu Asn Tyr  Phe Arg Asp
    1520                 1525                 1530

Ala Trp  Asn Val Phe Asp Phe  Val Thr Val Leu Gly  Ser Ile Thr
    1535                 1540                 1545

Asp Ile  Leu Val Thr Glu Ile  Ala Glu Thr Asn Asn  Phe Ile Asn
    1550                 1555                 1560

Leu Ser  Phe Leu Arg Leu Phe  Arg Ala Ala Arg Leu  Ile Lys Leu
    1565                 1570                 1575

Leu Arg  Gln Gly Tyr Thr Ile  Arg Ile Leu Leu Trp  Thr Phe Val
    1580                 1585                 1590

Gln Ser  Phe Lys Ala Leu Pro  Tyr Val Cys Leu Leu  Ile Ala Met
    1595                 1600                 1605

Leu Phe  Phe Ile Tyr Ala Ile  Ile Gly Met Gln Val  Phe Gly Asn
    1610                 1615                 1620

Ile Ala  Leu Asp Asp Asp Thr  Ser Ile Asn Arg His  Asn Asn Phe
    1625                 1630                 1635

Arg Thr  Phe Leu Gln Ala Leu  Met Leu Leu Phe Arg  Ser Ala Thr
    1640                 1645                 1650

Gly Glu  Ala Trp His Glu Ile  Met Leu Ser Cys Leu  Ser Asn Gln
    1655                 1660                 1665

Ala Cys  Asp Glu Gln Ala Asn  Ala Thr Glu Cys Gly  Ser Asp Phe
    1670                 1675                 1680

Ala Tyr  Phe Tyr Phe Val Ser  Phe Ile Phe Leu Cys  Ser Phe Leu
    1685                 1690                 1695

Met Leu  Asn Leu Phe Val Ala  Val Ile Met Asp Asn  Phe Glu Tyr
    1700                 1705                 1710

Leu Thr  Arg Asp Ser Ser Ile  Leu Gly Pro His His  Leu Asp Glu
    1715                 1720                 1725

Phe Ile  Arg Val Trp Ala Glu  Tyr Asp Pro Ala Ala  Cys Gly Arg
    1730                 1735                 1740

Ile Ser  Tyr Asn Asp Met Phe  Glu Met Leu Lys His  Met Ser Pro
    1745                 1750                 1755

Pro Leu  Gly Leu Gly Lys Lys  Cys Pro Ala Arg Val  Ala Tyr Lys
    1760                 1765                 1770
```

```
Arg Leu  Val Arg Met Asn Met  Pro Ile Ser Asn Glu  Asp Met Thr
    1775                 1780                 1785

Val His  Phe Thr Ser Thr Leu  Met Ala Leu Ile Arg  Thr Ala Leu
    1790                 1795                 1800

Glu Ile  Lys Leu Ala Pro Ala  Gly Thr Lys Gln His  Gln Cys Asp
    1805                 1810                 1815

Ala Glu  Leu Arg Lys Glu Ile  Ser Val Val Trp Ala  Asn Leu Pro
    1820                 1825                 1830

Gln Lys  Thr Leu Asp Leu Leu  Val Pro Pro His Lys  Pro Asp Glu
    1835                 1840                 1845

Met Thr  Val Gly Lys Val Tyr  Ala Ala Leu Met Ile  Phe Asp Phe
    1850                 1855                 1860

Tyr Lys  Gln Asn Lys Thr Thr  Arg Asp Gln Met Gln  Gln Ala Pro
    1865                 1870                 1875

Gly Gly  Leu Ser Gln Met Gly  Pro Val Ser Leu Phe  His Pro Leu
    1880                 1885                 1890

Lys Ala  Thr Leu Glu Gln Thr  Gln Pro Ala Val Leu  Arg Gly Ala
    1895                 1900                 1905

Arg Val  Phe Leu Arg Gln Lys  Ser Ser Thr Ser Leu  Ser Asn Gly
    1910                 1915                 1920

Gly Ala  Ile Gln Asn Gln Glu  Ser Gly Ile Lys Glu  Ser Val Ser
    1925                 1930                 1935

Trp Gly  Thr Gln Arg Thr Gln  Asp Ala Pro His Glu  Ala Arg Pro
    1940                 1945                 1950

Pro Leu  Glu Arg Gly His Ser  Thr Glu Ile Pro Val  Gly Arg Ser
    1955                 1960                 1965

Gly Ala  Leu Ala Val Asp Val  Gln Met Gln Ser Ile  Thr Arg Arg
    1970                 1975                 1980

Gly Pro  Asp Gly Glu Pro Gln  Pro Gly Leu Glu Ser  Gln Gly Arg
    1985                 1990                 1995

Ala Ala  Ser Met Pro Arg Leu  Ala Ala Glu Thr Gln  Pro Val Thr
    2000                 2005                 2010

Asp Ala  Ser Pro Met Lys Arg  Ser Ile Ser Thr Leu  Ala Gln Arg
    2015                 2020                 2025

Pro Arg  Gly Thr His Leu Cys  Ser Thr Thr Pro Asp  Arg Pro Pro
    2030                 2035                 2040

Pro Ser  Gln Ala Ser Ser His  His His His His Arg  Cys His Arg
    2045                 2050                 2055

Arg Arg  Asp Arg Lys Gln Arg  Ser Leu Glu Lys Gly  Pro Ser Leu
    2060                 2065                 2070

Ser Ala  Asp Met Asp Gly Ala  Pro Ser Ser Ala Val  Gly Pro Gly
    2075                 2080                 2085

Leu Pro  Pro Gly Glu Gly Pro  Thr Gly Cys Arg Arg  Glu Arg Glu
    2090                 2095                 2100

Arg Arg  Gln Glu Arg Gly Arg  Ser Gln Glu Arg Arg  Gln Pro Ser
    2105                 2110                 2115

Ser Ser  Ser Ser Glu Lys Gln  Arg Phe Tyr Ser Cys  Asp Arg Phe
    2120                 2125                 2130

Gly Gly  Arg Glu Pro Pro Lys  Pro Lys Pro Ser Leu  Ser Ser His
    2135                 2140                 2145

Pro Thr  Ser Pro Thr Ala Gly  Gln Glu Pro Gly Pro  His Pro Gln
    2150                 2155                 2160

Gly Ser  Gly Ser Val Asn Gly  Ser Pro Leu Leu Ser  Thr Ser Gly
```

```
    2165                2170                2175

Ala Ser  Thr Pro Gly Arg Gly  Gly Arg Arg Gln Leu  Pro Gln Thr
    2180                2185                2190

Pro Leu  Thr Pro Arg Pro Ser  Ile Thr Tyr Lys Thr  Ala Asn Ser
    2195                2200                2205

Ser Pro  Ile His Phe Ala Gly  Ala Gln Thr Ser Leu  Pro Ala Phe
    2210                2215                2220

Ser Pro  Gly Arg Leu Ser Arg  Gly Leu Ser Glu His  Asn Ala Leu
    2225                2230                2235

Leu Gln  Arg Asp Pro Leu Ser  Gln Pro Leu Ala Pro  Gly Ser Arg
    2240                2245                2250

Ile Gly  Ser Asp Pro Tyr Leu  Gly Gln Arg Leu Asp  Ser Glu Ala
    2255                2260                2265

Ser Val  His Ala Leu Pro Glu  Asp Thr Leu Thr Phe  Glu Glu Ala
    2270                2275                2280

Val Ala  Thr Asn Ser Gly Arg  Ser Ser Arg Thr Ser  Tyr Val Ser
    2285                2290                2295

Ser Leu  Thr Ser Gln Ser His  Pro Leu Arg Arg Val  Pro Asn Gly
    2300                2305                2310

Tyr His  Cys Thr Leu Gly Leu  Ser Ser Gly Gly Arg  Ala Arg His
    2315                2320                2325

Ser Tyr  His His Pro Asp Gln  Asp His Trp Cys
    2330                2335
```

<210> SEQ ID NO 5
<211> LENGTH: 1232
<212> TYPE: DNA
<213> ORGANISM: Artificial Sequence
<220> FEATURE:
<223> OTHER INFORMATION: synthesized

<400> SEQUENCE: 5

```
accggtttgc agatctctgt gctgttggat ccccccttcgc ccgcgccagc ctcaagagcg     60

ggaagacaga gagctcgtca tacttccgga ggaaggagaa gatgttccgg ttttttatcc    120

ggcgcatggt gaaggctcag agcttctact gggtggtgct gtgcgtggtg gccctgaaca    180

cactgtgtgt ggccatggtg cattacaacc agccgcggcg gcttaccacg accctgtatt    240

ttgcagagtt tgttttcctg ggtctcttcc tcacagagat gtccctgaag atgtatggcc    300

tggggcccag aagctacttc cggtcctcct tcaactgctt cgactttggg gtcatcgtgg    360

ggagcgtctt tgaagtggtc tgggcggcca tcaggccggg aagctccttt gggatcagtg    420

tgctgcgggc cctccgcctg ctgaggatct tcaaagtcac gaagtactgg agctccctgc    480

ggaacctggt ggtgtccctg ctgaactcca tgaagtccat catcagcctg ctcttcttgc    540

tcttcctgtt cattgtggtc ttcgccctgc tggggatgca gctgtttggg ggacagttca    600

acttccagga tgagactccc acaaccaact tcgacacctt ccctgccgcc atcctcactg    660

tcttccagat cctgacggga gaggactgga atgcagtgat gtatcacggg atcgaatcgc    720

aaggcggcgt cagcaaaggc atgttctcgt ccttttactt cattgtcctg acactgttcg    780

gaaactacac tctgctgaat gtctttctgg ccatcgctgt ggacaacctg gccaacgccc    840

aagagctgac caaggatgaa gaggagatgg aagaagcagc caatcagaag cttgctctgc    900

aaaaggccaa agaagtggct gaagtcagcc ccatgtctgc cgcgaacatc tccatcgccg    960

ccaggcagca gaactcggcc aaggcgcgct cggtgtggga gcagcgggcc agccagctac   1020
```

```
ggctgcagaa cctgcgggcc agctgcgagg cgctgtacag cgagatggac cccgaggagc   1080

ggctgcgctt cgccactacg cgccacctgc ggcccgacat gaagacgcac ctggaccggc   1140

cgctggtggt ggagctgggc cgcgacggcg cgcgggggcc cgtgggaggc aaagcccgac   1200

ctgaggctgc ggaggccccc gagggcgtcg ac                                 1232


<210> SEQ ID NO 6
<211> LENGTH: 20
<212> TYPE: DNA
<213> ORGANISM: Artificial Sequence
<220> FEATURE:
<223> OTHER INFORMATION: synthesized

<400> SEQUENCE: 6

gtctgggctg ccatcaagcc                                                 20


<210> SEQ ID NO 7
<211> LENGTH: 120
<212> TYPE: DNA
<213> ORGANISM: Artificial Sequence
<220> FEATURE:
<223> OTHER INFORMATION: synthesized

<400> SEQUENCE: 7

ggtactgttt ctttcaggtg attgtgggga gtatctttga agtagtctgg gctgccattc     60

ggccaggaac ctccttcgga atcagtgtgc tgcgggctct ccgactgctg aggattttca    120


<210> SEQ ID NO 8
<211> LENGTH: 2354
<212> TYPE: PRT
<213> ORGANISM: Rattus norvegicus

<400> SEQUENCE: 8

Met Val Arg Phe Gly Asp Glu Leu Gly Gly Arg Tyr Gly Gly Thr Gly
1               5                   10                  15

Gly Gly Glu Arg Ala Arg Gly Gly Gly Ala Gly Gly Ala Gly Gly Pro
            20                  25                  30

Gly Gln Gly Gly Leu Pro Pro Gly Gln Arg Val Leu Tyr Lys Gln Ser
        35                  40                  45

Ile Ala Gln Arg Ala Arg Thr Met Ala Leu Tyr Asn Pro Ile Pro Val
    50                  55                  60

Lys Gln Asn Cys Phe Thr Val Asn Arg Ser Leu Phe Val Phe Ser Glu
65                  70                  75                  80

Asp Asn Val Val Arg Lys Tyr Ala Lys Arg Ile Thr Glu Trp Pro Pro
                85                  90                  95

Phe Glu Tyr Met Ile Leu Ala Thr Ile Ile Ala Asn Cys Ile Val Leu
            100                 105                 110

Ala Leu Glu Gln His Leu Pro Asp Gly Asp Lys Thr Pro Met Ser Glu
        115                 120                 125

Arg Leu Asp Asp Thr Glu Pro Tyr Phe Ile Gly Ile Phe Cys Phe Glu
    130                 135                 140

Ala Gly Ile Lys Ile Ile Ala Leu Gly Phe Val Phe His Lys Gly Ser
145                 150                 155                 160

Tyr Leu Arg Asn Gly Trp Asn Val Met Asp Phe Val Val Val Leu Thr
                165                 170                 175

Gly Ile Leu Ala Thr Ala Gly Thr Asp Phe Asp Leu Arg Thr Leu Arg
            180                 185                 190

Ala Val Arg Val Leu Arg Pro Leu Lys Leu Val Ser Gly Ile Pro Ser
```

```
        195                 200                 205

Leu Gln Val Val Leu Lys Ser Ile Met Lys Ala Met Val Pro Leu Leu
    210                 215                 220

Gln Ile Gly Leu Leu Leu Phe Phe Ala Ile Leu Met Phe Ala Ile Ile
225                 230                 235                 240

Gly Leu Glu Phe Tyr Met Gly Lys Phe His Lys Ala Cys Phe Pro Asn
                245                 250                 255

Ser Thr Asp Ala Glu Pro Val Gly Asp Phe Pro Cys Gly Lys Glu Ala
            260                 265                 270

Pro Ala Arg Leu Cys Asp Ser Asp Thr Glu Cys Arg Glu Tyr Trp Pro
        275                 280                 285

Gly Pro Asn Phe Gly Ile Thr Asn Phe Asp Asn Ile Leu Phe Ala Ile
    290                 295                 300

Leu Thr Val Phe Gln Cys Ile Thr Met Glu Gly Trp Thr Asp Ile Leu
305                 310                 315                 320

Tyr Asn Thr Asn Asp Ala Ala Gly Asn Thr Trp Asn Trp Leu Tyr Phe
                325                 330                 335

Ile Pro Leu Ile Ile Ile Gly Ser Phe Phe Met Leu Asn Leu Val Leu
            340                 345                 350

Gly Val Leu Ser Gly Glu Phe Ala Lys Glu Arg Glu Arg Val Glu Asn
        355                 360                 365

Arg Arg Ala Phe Leu Lys Leu Arg Arg Gln Gln Gln Ile Glu Arg Glu
    370                 375                 380

Leu Asn Gly Tyr Leu Glu Trp Ile Phe Lys Ala Glu Glu Val Met Leu
385                 390                 395                 400

Ala Glu Glu Asp Lys Asn Ala Glu Glu Lys Ser Pro Leu Asp Ala Val
                405                 410                 415

Leu Lys Arg Ala Ala Thr Lys Lys Ser Arg Asn Asp Leu Ile His Ala
            420                 425                 430

Glu Glu Gly Glu Asp Arg Phe Val Asp Leu Cys Ala Ala Gly Ser Pro
        435                 440                 445

Phe Ala Arg Ala Ser Leu Lys Ser Gly Lys Thr Glu Ser Ser Ser Tyr
    450                 455                 460

Phe Arg Arg Lys Glu Lys Met Phe Arg Phe Leu Ile Arg Arg Met Val
465                 470                 475                 480

Lys Ala Gln Ser Phe Tyr Trp Val Val Leu Cys Val Val Ala Leu Asn
                485                 490                 495

Thr Leu Cys Val Ala Met Val His Tyr Asn Gln Pro Gln Arg Leu Thr
            500                 505                 510

Thr Ala Leu Tyr Phe Ala Glu Phe Val Phe Leu Gly Leu Phe Leu Thr
        515                 520                 525

Glu Met Ser Leu Lys Met Tyr Gly Leu Gly Pro Arg Ser Tyr Phe Arg
    530                 535                 540

Ser Ser Phe Asn Cys Phe Asp Phe Gly Val Ile Val Gly Ser Ile Phe
545                 550                 555                 560

Glu Val Val Trp Ala Ala Ile Lys Pro Gly Thr Ser Phe Gly Ile Ser
                565                 570                 575

Val Leu Arg Ala Leu Arg Leu Leu Arg Ile Phe Lys Val Thr Lys Tyr
            580                 585                 590

Trp Asn Ser Leu Arg Asn Leu Val Val Ser Leu Leu Asn Ser Met Lys
        595                 600                 605

Ser Ile Ile Ser Leu Leu Phe Leu Leu Phe Leu Phe Ile Val Val Phe
    610                 615                 620
```

```
Ala Leu Leu Gly Met Gln Leu Phe Gly Gly Gln Phe Asn Phe Gln Asp
625                 630                 635                 640

Glu Thr Pro Thr Thr Asn Phe Asp Thr Phe Pro Ala Ala Ile Leu Thr
                645                 650                 655

Val Phe Gln Ile Leu Thr Gly Glu Asp Trp Asn Ala Val Met Tyr His
            660                 665                 670

Gly Ile Glu Ser Gln Gly Gly Val Ser Lys Gly Met Phe Ser Ser Phe
        675                 680                 685

Tyr Phe Ile Val Leu Thr Leu Phe Gly Asn Tyr Thr Leu Leu Asn Val
    690                 695                 700

Phe Leu Ala Ile Ala Val Asp Asn Leu Ala Asn Ala Gln Glu Leu Thr
705                 710                 715                 720

Lys Asp Glu Glu Glu Met Glu Glu Ala Ala Asn Gln Lys Leu Ala Leu
                725                 730                 735

Gln Lys Ala Lys Glu Val Ala Glu Val Ser Pro Met Ser Ala Ala Asn
            740                 745                 750

Ile Ser Ile Ala Ala Phe Val Lys Gln Thr Arg Gly Thr Val Ser Arg
        755                 760                 765

Ser Ser Ser Val Ser Ser Val Asn Ser Pro Gln Gln Asn Ser Ala Lys
    770                 775                 780

Ala Arg Ser Val Trp Glu Gln Arg Ala Ser Gln Leu Arg Leu Gln Asn
785                 790                 795                 800

Leu Arg Ala Ser Cys Glu Ala Leu Tyr Ser Glu Met Asp Pro Glu Glu
                805                 810                 815

Arg Leu Arg Tyr Ala Ser Thr Arg His Val Arg Pro Asp Met Lys Thr
            820                 825                 830

His Met Asp Arg Pro Leu Val Val Glu Pro Gly Arg Asp Gly Leu Arg
        835                 840                 845

Gly Pro Ala Gly Asn Lys Ser Lys Pro Glu Gly Thr Glu Ala Thr Glu
    850                 855                 860

Gly Ala Asp Pro Pro Arg Arg His His Arg His Arg Asp Arg Asp Lys
865                 870                 875                 880

Thr Ser Ala Ser Thr Pro Ala Gly Gly Glu Gln Asp Arg Thr Asp Cys
                885                 890                 895

Pro Lys Ala Glu Ser Thr Glu Thr Gly Ala Arg Glu Glu Arg Ala Arg
            900                 905                 910

Pro Arg Arg Ser His Ser Lys Glu Ala Pro Gly Ala Asp Thr Gln Val
        915                 920                 925

Arg Cys Glu Arg Ser Arg Arg His His Arg Arg Gly Ser Pro Glu Glu
    930                 935                 940

Ala Thr Glu Arg Glu Pro Arg Arg His Arg Ala His Arg His Ala Gln
945                 950                 955                 960

Asp Ser Ser Lys Glu Gly Lys Glu Gly Thr Ala Pro Val Leu Val Pro
                965                 970                 975

Lys Gly Glu Arg Arg Ala Arg His Arg Gly Pro Arg Thr Gly Pro Arg
            980                 985                 990

Glu Thr Glu Asn Ser Glu Glu Pro  Thr Arg Arg His Arg  Ala Lys His
        995                 1000                1005

Lys Val  Pro Pro Thr Leu Glu  Pro Pro Glu Arg Glu  Val Ala Glu
    1010                1015                1020

Lys Glu  Ser Asn Val Val Glu  Gly Asp Lys Glu Thr  Arg Asn His
    1025                1030                1035
```

```
Gln Pro  Lys Glu Pro Arg Cys  Asp Leu Glu Ala Ile  Ala Val Thr
    1040                 1045                 1050

Gly Val  Gly Ser Leu His Met  Leu Pro Ser Thr Cys  Leu Gln Lys
    1055                 1060                 1065

Val Asp  Glu Gln Pro Glu Asp  Ala Asp Asn Gln Arg  Asn Val Thr
    1070                 1075                 1080

Arg Met  Gly Ser Gln Pro Ser  Asp Pro Ser Thr Thr  Val His Val
    1085                 1090                 1095

Pro Val  Thr Leu Thr Gly Pro  Pro Gly Glu Ala Thr  Val Val Pro
    1100                 1105                 1110

Ser Ala  Asn Thr Asp Leu Glu  Gly Gln Ala Glu Gly  Lys Lys Glu
    1115                 1120                 1125

Ala Glu  Ala Asp Asp Val Leu  Arg Arg Gly Pro Arg  Pro Ile Val
    1130                 1135                 1140

Pro Tyr  Ser Ser Met Phe Cys  Leu Ser Pro Thr Asn  Leu Leu Arg
    1145                 1150                 1155

Arg Phe  Cys His Tyr Ile Val  Thr Met Arg Tyr Phe  Glu Met Val
    1160                 1165                 1170

Ile Leu  Val Val Ile Ala Leu  Ser Ser Ile Ala Leu  Ala Ala Glu
    1175                 1180                 1185

Asp Pro  Val Arg Thr Asp Ser  Phe Arg Asn Asn Ala  Leu Lys Tyr
    1190                 1195                 1200

Met Asp  Tyr Ile Phe Thr Gly  Val Phe Thr Phe Glu  Met Val Ile
    1205                 1210                 1215

Lys Met  Ile Asp Leu Gly Leu  Leu Leu His Pro Gly  Ala Tyr Phe
    1220                 1225                 1230

Arg Asp  Leu Trp Asn Ile Leu  Asp Phe Ile Val Val  Ser Gly Ala
    1235                 1240                 1245

Leu Val  Ala Phe Ala Phe Ser  Gly Ser Lys Gly Lys  Asp Ile Asn
    1250                 1255                 1260

Thr Ile  Lys Ser Leu Arg Val  Leu Arg Val Leu Arg  Pro Leu Lys
    1265                 1270                 1275

Thr Ile  Lys Arg Leu Pro Lys  Leu Lys Ala Val Phe  Asp Cys Val
    1280                 1285                 1290

Val Asn  Ser Leu Lys Asn Val  Leu Asn Ile Leu Ile  Val Tyr Met
    1295                 1300                 1305

Leu Phe  Met Phe Ile Phe Ala  Val Ile Ala Val Gln  Leu Phe Lys
    1310                 1315                 1320

Gly Lys  Phe Phe Tyr Cys Thr  Asp Glu Ser Lys Glu  Leu Glu Arg
    1325                 1330                 1335

Asp Cys  Arg Gly Gln Tyr Leu  Asp Tyr Glu Lys Glu  Glu Val Glu
    1340                 1345                 1350

Ala Gln  Pro Arg Gln Trp Lys  Lys Tyr Asp Phe His  Tyr Asp Asn
    1355                 1360                 1365

Val Leu  Trp Ala Leu Leu Thr  Leu Phe Thr Val Ser  Thr Gly Glu
    1370                 1375                 1380

Gly Trp  Pro Met Val Leu Lys  His Ser Val Asp Ala  Thr Tyr Glu
    1385                 1390                 1395

Glu Gln  Gly Pro Ser Pro Gly  Phe Arg Met Glu Leu  Ser Ile Phe
    1400                 1405                 1410

Tyr Val  Val Tyr Phe Val Val  Phe Pro Phe Phe Phe  Val Asn Ile
    1415                 1420                 1425

Phe Val  Ala Leu Ile Ile Ile  Thr Phe Gln Glu Gln  Gly Asp Lys
```

```
    1430                1435                1440

Val Met  Ser Glu Cys Ser Leu  Glu Lys Asn Glu Arg  Ala Cys Ile
    1445                1450                1455

Asp Phe  Ala Ile Ser Ala Lys  Pro Leu Thr Arg Tyr  Met Pro Gln
    1460                1465                1470

Asn Lys  Gln Ser Phe Gln Tyr  Lys Thr Trp Thr Phe  Val Val Ser
    1475                1480                1485

Pro Pro  Phe Glu Tyr Phe Ile  Met Ala Met Ile Ala  Leu Asn Thr
    1490                1495                1500

Val Val  Leu Met Met Lys Phe  Tyr Asp Ala Pro Tyr  Glu Tyr Glu
    1505                1510                1515

Leu Met  Leu Lys Cys Leu Asn  Ile Val Phe Thr Ser  Met Phe Ser
    1520                1525                1530

Leu Glu  Cys Ile Leu Lys Ile  Ile Ala Phe Gly Val  Leu Asn Tyr
    1535                1540                1545

Phe Arg  Asp Ala Trp Asn Val  Phe Asp Phe Val Thr  Val Leu Gly
    1550                1555                1560

Ser Ile  Thr Asp Ile Leu Val  Thr Glu Ile Ala Glu  Thr Asn Asn
    1565                1570                1575

Phe Ile  Asn Leu Ser Phe Leu  Arg Leu Phe Arg Ala  Ala Arg Leu
    1580                1585                1590

Ile Lys  Leu Leu Arg Gln Gly  Tyr Thr Ile Arg Ile  Leu Leu Trp
    1595                1600                1605

Thr Phe  Val Gln Ser Phe Lys  Ala Leu Pro Tyr Val  Cys Leu Leu
    1610                1615                1620

Ile Ala  Met Leu Phe Phe Ile  Tyr Ala Ile Ile Gly  Met Gln Val
    1625                1630                1635

Phe Gly  Asn Ile Ala Leu Asp  Asp Gly Thr Ser Ile  Asn Arg His
    1640                1645                1650

Asn Asn  Phe Arg Thr Phe Leu  Gln Ala Leu Met Leu  Leu Phe Arg
    1655                1660                1665

Ser Ala  Thr Gly Glu Ala Trp  His Glu Ile Met Leu  Ser Cys Leu
    1670                1675                1680

Gly Asn  Arg Ala Cys Asp Pro  His Ala Asn Ala Ser  Glu Cys Gly
    1685                1690                1695

Ser Asp  Phe Ala Tyr Phe Tyr  Phe Val Ser Phe Ile  Phe Leu Cys
    1700                1705                1710

Ser Phe  Leu Met Leu Asn Leu  Phe Val Ala Val Ile  Met Asp Asn
    1715                1720                1725

Phe Glu  Tyr Leu Thr Arg Asp  Ser Ser Ile Leu Gly  Pro His His
    1730                1735                1740

Leu Asp  Glu Phe Ile Arg Val  Trp Ala Glu Tyr Asp  Pro Ala Ala
    1745                1750                1755

Cys Gly  Arg Ile Ser Tyr Asn  Asp Met Phe Glu Met  Leu Lys His
    1760                1765                1770

Met Ser  Pro Pro Leu Gly Leu  Gly Lys Lys Cys Pro  Ala Arg Val
    1775                1780                1785

Ala Tyr  Lys Arg Leu Val Arg  Met Asn Met Pro Ile  Ser Asn Glu
    1790                1795                1800

Asp Met  Thr Val His Phe Thr  Ser Thr Leu Met Ala  Leu Ile Arg
    1805                1810                1815

Thr Ala  Leu Glu Ile Lys Leu  Ala Pro Ala Gly Thr  Lys Gln His
    1820                1825                1830
```

```
Gln Cys  Asp Ala Glu Leu Arg  Lys Glu Ile Ser Ser  Val Trp Ala
    1835                 1840                 1845

Asn Leu  Pro Gln Lys Thr Leu  Asp Leu Leu Val Pro  Pro His Lys
    1850                 1855                 1860

Pro Asp  Glu Met Thr Val Gly  Lys Val Tyr Ala Ala  Leu Met Ile
    1865                 1870                 1875

Phe Asp  Phe Tyr Lys Gln Asn  Lys Thr Thr Arg Asp  Gln Thr His
    1880                 1885                 1890

Gln Ala  Pro Gly Gly Leu Ser  Gln Met Gly Pro Val  Ser Leu Phe
    1895                 1900                 1905

His Pro  Leu Lys Ala Thr Leu  Glu Gln Thr Gln Pro  Ala Val Leu
    1910                 1915                 1920

Arg Gly  Ala Arg Val Phe Leu  Arg Gln Lys Ser Ala  Thr Ser Leu
    1925                 1930                 1935

Ser Asn  Gly Gly Ala Ile Gln  Thr Gln Glu Ser Gly  Ile Lys Glu
    1940                 1945                 1950

Ser Leu  Ser Trp Gly Thr Gln  Arg Thr Gln Asp Val  Leu Tyr Glu
    1955                 1960                 1965

Ala Arg  Ala Pro Leu Glu Arg  Gly His Ser Ala Glu  Ile Pro Val
    1970                 1975                 1980

Gly Gln  Pro Gly Ala Leu Ala  Val Asp Val Gln Met  Gln Asn Met
    1985                 1990                 1995

Thr Leu  Arg Gly Pro Asp Gly  Glu Pro Gln Pro Gly  Leu Glu Ser
    2000                 2005                 2010

Gln Gly  Arg Ala Ala Ser Met  Pro Arg Leu Ala Ala  Glu Thr Gln
    2015                 2020                 2025

Pro Ala  Pro Asn Ala Ser Pro  Met Lys Arg Ser Ile  Ser Thr Leu
    2030                 2035                 2040

Ala Pro  Arg Pro His Gly Thr  Gln Leu Cys Asn Thr  Val Leu Asp
    2045                 2050                 2055

Arg Pro  Pro Pro Ser Gln Val  Ser His His His His  His Arg Cys
    2060                 2065                 2070

His Arg  Arg Arg Asp Lys Lys  Gln Arg Ser Leu Glu  Lys Gly Pro
    2075                 2080                 2085

Ser Leu  Ser Val Asp Thr Glu  Gly Ala Pro Ser Thr  Ala Ala Gly
    2090                 2095                 2100

Ser Gly  Leu Pro His Gly Glu  Gly Ser Thr Gly Cys  Arg Arg Glu
    2105                 2110                 2115

Arg Lys  Gln Glu Arg Gly Arg  Ser Gln Glu Arg Arg  Gln Pro Ser
    2120                 2125                 2130

Ser Ser  Ser Ser Glu Lys Gln  Arg Phe Tyr Ser Cys  Asp Arg Phe
    2135                 2140                 2145

Gly Ser  Arg Glu Pro Pro Gln  Pro Lys Pro Ser Leu  Ser Ser His
    2150                 2155                 2160

Pro Ile  Ser Pro Thr Ala Ala  Leu Glu Pro Gly Pro  His Pro Gln
    2165                 2170                 2175

Gly Ser  Gly Ser Val Asn Gly  Ser Pro Leu Met Ser  Thr Ser Gly
    2180                 2185                 2190

Ala Ser  Thr Pro Gly Arg Gly  Gly Arg Arg Gln Leu  Pro Gln Thr
    2195                 2200                 2205

Pro Leu  Thr Pro Arg Pro Ser  Ile Thr Tyr Lys Thr  Ala Asn Ser
    2210                 2215                 2220
```

```
Ser Pro  Val His Phe Ala Glu  Gly Gln Ser Gly Leu  Pro Ala Phe
    2225                 2230                 2235

Ser Pro  Gly Arg Leu Ser Arg  Gly Leu Ser Glu His  Asn Ala Leu
    2240                 2245                 2250

Leu Gln  Lys Glu Pro Leu Ser  Gln Pro Leu Ala Ser  Gly Ser Arg
    2255                 2260                 2265

Ile Gly  Ser Asp Pro Tyr Leu  Gly Gln Arg Leu Asp  Ser Glu Ala
    2270                 2275                 2280

Ser Ala  His Asn Leu Pro Glu  Asp Thr Leu Thr Phe  Glu Glu Ala
    2285                 2290                 2295

Val Ala  Thr Asn Ser Gly Arg  Ser Ser Arg Thr Ser  Tyr Val Ser
    2300                 2305                 2310

Ser Leu  Thr Ser Gln Ser His  Pro Leu Arg Arg Val  Pro Asn Gly
    2315                 2320                 2325

Tyr His  Cys Thr Leu Gly Leu  Ser Thr Gly Val Arg  Ala Arg His
    2330                 2335                 2340

Ser Tyr  His His Pro Asp Gln  Asp His Trp Cys
    2345                 2350


<210> SEQ ID NO 9
<211> LENGTH: 2327
<212> TYPE: PRT
<213> ORGANISM: Mus musculus

<400> SEQUENCE: 9

Met Val Arg Phe Gly Asp Glu Leu Gly Gly Arg Tyr Gly Gly Thr Gly
1               5                   10                  15

Gly Gly Glu Arg Ala Arg Gly Gly Gly Ala Gly Gly Ala Gly Gly Pro
            20                  25                  30

Gly Gln Gly Gly Leu Pro Pro Gly Gln Arg Val Leu Tyr Lys Gln Ser
        35                  40                  45

Ile Ala Gln Arg Ala Arg Thr Met Ala Leu Tyr Asn Pro Ile Pro Val
    50                  55                  60

Lys Gln Asn Cys Phe Thr Val Asn Arg Ser Leu Phe Val Phe Ser Glu
65                  70                  75                  80

Asp Asn Val Val Arg Lys Tyr Ala Lys Arg Ile Thr Glu Trp Pro Pro
                85                  90                  95

Phe Glu Tyr Met Ile Leu Ala Thr Ile Ile Ala Asn Cys Ile Val Leu
            100                 105                 110

Ala Leu Glu Gln His Leu Pro Asp Gly Asp Lys Thr Pro Met Ser Glu
        115                 120                 125

Arg Leu Asp Asp Thr Glu Pro Tyr Phe Ile Gly Ile Phe Cys Phe Glu
    130                 135                 140

Ala Gly Ile Lys Ile Ile Ala Leu Gly Phe Val Phe His Lys Gly Ser
145                 150                 155                 160

Tyr Leu Arg Asn Gly Trp Asn Val Met Asp Phe Val Val Val Leu Thr
                165                 170                 175

Gly Ile Leu Ala Thr Ala Gly Thr Asp Phe Asp Leu Arg Thr Leu Arg
            180                 185                 190

Ala Val Arg Val Leu Arg Pro Leu Lys Leu Val Ser Gly Ile Pro Ser
        195                 200                 205

Leu Gln Val Val Leu Lys Ser Ile Met Lys Ala Met Val Pro Leu Leu
    210                 215                 220

Gln Ile Gly Leu Leu Leu Phe Phe Ala Ile Leu Met Phe Ala Ile Ile
225                 230                 235                 240
```

```
Gly Leu Glu Phe Tyr Met Gly Lys Phe His Lys Ala Cys Phe Pro Asn
                245                 250                 255

Ser Thr Asp Thr Glu Pro Val Gly Asp Phe Pro Cys Gly Lys Asp Pro
            260                 265                 270

Pro Ala Arg Gln Cys Asp Gly Asp Thr Glu Cys Arg Glu Tyr Trp Pro
        275                 280                 285

Gly Pro Asn Phe Gly Ile Thr Asn Phe Asp Asn Ile Leu Phe Ala Ile
    290                 295                 300

Leu Thr Val Phe Gln Cys Ile Thr Met Glu Gly Trp Thr Asp Ile Leu
305                 310                 315                 320

Tyr Asn Thr Asn Asp Ala Ala Gly Asn Thr Trp Asn Trp Leu Tyr Phe
                325                 330                 335

Ile Pro Leu Ile Ile Ile Gly Ser Phe Phe Met Leu Asn Leu Val Leu
            340                 345                 350

Gly Val Leu Ser Gly Glu Phe Ala Lys Glu Arg Glu Arg Val Glu Asn
        355                 360                 365

Arg Arg Ala Phe Leu Lys Leu Arg Arg Gln Gln Gln Ile Glu Arg Glu
    370                 375                 380

Leu Asn Gly Tyr Leu Glu Trp Ile Phe Lys Ala Glu Glu Val Met Leu
385                 390                 395                 400

Ala Glu Glu Asp Lys Asn Ala Glu Glu Lys Ser Pro Leu Asp Val Leu
                405                 410                 415

Lys Arg Ala Ala Thr Lys Lys Ser Arg Asn Asp Leu Ile His Ala Glu
            420                 425                 430

Glu Gly Glu Asp Arg Phe Val Asp Leu Cys Ala Val Gly Ser Pro Phe
        435                 440                 445

Ala Arg Ala Ser Leu Lys Ser Gly Lys Thr Glu Ser Ser Ser Tyr Phe
    450                 455                 460

Arg Arg Lys Glu Lys Met Phe Arg Phe Phe Ile Arg Arg Met Val Lys
465                 470                 475                 480

Ala Gln Ser Phe Tyr Trp Val Val Leu Cys Val Val Ala Leu Asn Thr
                485                 490                 495

Leu Cys Val Ala Met Val His Tyr Asn Gln Pro Gln Arg Leu Thr Thr
            500                 505                 510

Ala Leu Tyr Phe Ala Glu Phe Val Phe Leu Gly Leu Phe Leu Thr Glu
        515                 520                 525

Met Ser Leu Lys Met Tyr Gly Leu Gly Pro Arg Ser Tyr Phe Arg Ser
    530                 535                 540

Ser Phe Asn Cys Phe Asp Phe Gly Val Ile Val Gly Ser Ile Phe Glu
545                 550                 555                 560

Val Val Trp Ala Ala Ile Lys Pro Gly Thr Ser Phe Gly Ile Ser Val
                565                 570                 575

Leu Arg Ala Leu Arg Leu Leu Arg Ile Phe Lys Val Thr Lys Tyr Trp
            580                 585                 590

Asn Ser Leu Arg Asn Leu Val Val Ser Leu Leu Asn Ser Met Lys Ser
        595                 600                 605

Ile Ile Ser Leu Leu Phe Leu Leu Phe Leu Phe Ile Val Val Phe Ala
    610                 615                 620

Leu Leu Gly Met Gln Leu Phe Gly Gly Gln Phe Asn Phe Gln Asp Glu
625                 630                 635                 640

Thr Pro Thr Thr Asn Phe Asp Thr Phe Pro Ala Ala Ile Leu Thr Val
                645                 650                 655
```

-continued

```
Phe Gln Ile Leu Thr Gly Glu Asp Trp Asn Ala Val Met Tyr His Gly
            660                 665                 670

Ile Glu Ser Gln Gly Gly Val Ser Lys Gly Met Phe Ser Ser Phe Tyr
        675                 680                 685

Phe Ile Val Leu Thr Leu Phe Gly Asn Tyr Thr Leu Leu Asn Val Phe
    690                 695                 700

Leu Ala Ile Ala Val Asp Asn Leu Ala Asn Ala Gln Glu Leu Thr Lys
705                 710                 715                 720

Asp Glu Glu Glu Met Glu Glu Ala Ala Asn Gln Lys Leu Ala Leu Gln
                725                 730                 735

Lys Ala Lys Glu Val Ala Glu Val Ser Pro Met Ser Ala Ala Asn Ile
            740                 745                 750

Ser Ile Ala Ala Arg Gln Gln Asn Ser Ala Lys Ala Arg Ser Val Trp
        755                 760                 765

Glu Gln Arg Ala Ser Gln Leu Arg Leu Gln Asn Leu Arg Ala Ser Cys
    770                 775                 780

Glu Ala Leu Tyr Ser Glu Met Asp Pro Glu Glu Arg Leu Arg Tyr Ala
785                 790                 795                 800

Ser Thr Arg His Val Arg Pro Asp Met Lys Thr His Met Asp Arg Pro
                805                 810                 815

Leu Val Val Glu Pro Gly Arg Asp Gly Leu Arg Gly Pro Val Gly Ser
            820                 825                 830

Lys Ser Lys Pro Glu Gly Thr Glu Ala Thr Glu Ser Ala Asp Leu Pro
        835                 840                 845

Arg Arg His His Arg His Arg Asp Arg Asp Lys Thr Ser Ala Thr Ala
    850                 855                 860

Pro Ala Gly Gly Glu Gln Asp Arg Thr Glu Ser Thr Glu Thr Gly Ala
865                 870                 875                 880

Arg Glu Glu Arg Ala Arg Pro Arg Arg Ser His Ser Lys Glu Thr Pro
                885                 890                 895

Gly Ala Asp Thr Gln Val Arg Cys Glu Arg Ser Arg Arg His His Arg
            900                 905                 910

Arg Gly Ser Pro Glu Glu Ala Thr Glu Arg Glu Pro Arg Arg His Arg
        915                 920                 925

Ala His Arg His Ala Gln Asp Ser Ser Lys Glu Gly Thr Ala Pro Val
    930                 935                 940

Leu Val Pro Lys Gly Glu Arg Arg Ala Arg His Arg Gly Pro Arg Thr
945                 950                 955                 960

Gly Pro Arg Glu Ala Glu Asn Asn Glu Glu Pro Thr Arg Arg His Arg
                965                 970                 975

Ala Arg His Lys Val Pro Pro Thr Leu Gln Pro Pro Glu Arg Glu Ala
            980                 985                 990

Ala Glu Lys Glu Ser Asn Ala Val  Glu Gly Asp Lys Glu  Thr Arg Asn
        995                 1000                1005

His Gln  Pro Lys Glu Pro His  Cys Asp Leu Glu Ala  Ile Ala Val
    1010                1015                1020

Thr Gly  Val Gly Pro Leu His  Met Leu Pro Ser Thr  Cys Leu Gln
    1025                1030                1035

Lys Val  Asp Glu Gln Pro Glu  Asp Ala Asp Asn Gln  Arg Asn Val
    1040                1045                1050

Thr Arg  Met Gly Ser Gln Pro  Ser Asp Pro Ser Thr  Thr Val His
    1055                1060                1065

Val Pro  Val Thr Leu Thr Gly  Pro Pro Gly Glu Thr  Pro Val Val
```

```
    1070                1075                1080

Pro Ser  Gly Asn Met Asn Leu  Glu Gly Gln Ala Glu  Gly Lys Lys
    1085                1090                1095

Glu Ala  Glu Ala Asp Asp Val  Leu Arg Arg Gly Pro  Arg Pro Ile
    1100                1105                1110

Val Pro  Tyr Ser Ser Met Phe  Cys Leu Ser Pro Thr  Asn Leu Leu
    1115                1120                1125

Arg Arg  Phe Cys His Tyr Ile  Val Thr Met Arg Tyr  Phe Glu Met
    1130                1135                1140

Val Ile  Leu Val Val Ile Ala  Leu Ser Ser Ile Ala  Leu Ala Ala
    1145                1150                1155

Glu Asp  Pro Val Arg Thr Asp  Ser Phe Arg Asn Asn  Ala Leu Lys
    1160                1165                1170

Tyr Met  Asp Tyr Ile Phe Thr  Gly Val Phe Thr Phe  Glu Met Val
    1175                1180                1185

Ile Lys  Met Ile Asp Leu Gly  Leu Leu Leu His Pro  Gly Ala Tyr
    1190                1195                1200

Phe Arg  Asp Leu Trp Asn Ile  Leu Asp Phe Ile Val  Val Ser Gly
    1205                1210                1215

Ala Leu  Val Ala Phe Ala Phe  Ser Ser Phe Met Gly  Gly Ser Lys
    1220                1225                1230

Gly Lys  Asp Ile Asn Thr Ile  Lys Ser Leu Arg Val  Leu Arg Val
    1235                1240                1245

Leu Arg  Pro Leu Lys Thr Ile  Lys Arg Leu Pro Lys  Leu Lys Ala
    1250                1255                1260

Val Phe  Asp Cys Val Val Asn  Ser Leu Lys Asn Val  Leu Asn Ile
    1265                1270                1275

Leu Ile  Val Tyr Met Leu Phe  Met Phe Ile Phe Ala  Val Ile Ala
    1280                1285                1290

Val Gln  Leu Phe Lys Gly Lys  Phe Phe Tyr Cys Thr  Asp Glu Ser
    1295                1300                1305

Lys Glu  Leu Glu Arg Asp Cys  Arg Gly Gln Tyr Leu  Asp Tyr Glu
    1310                1315                1320

Lys Glu  Glu Val Glu Ala Gln  Pro Arg Gln Trp Lys  Lys Tyr Asp
    1325                1330                1335

Phe His  Tyr Asp Asn Val Leu  Trp Ala Leu Leu Thr  Leu Phe Thr
    1340                1345                1350

Val Ser  Thr Gly Glu Gly Trp  Pro Met Val Leu Lys  His Ser Val
    1355                1360                1365

Asp Ala  Thr Tyr Glu Glu Gln  Gly Pro Ser Pro Gly  Phe Arg Met
    1370                1375                1380

Glu Leu  Ser Ile Phe Tyr Val  Val Tyr Phe Val Val  Phe Pro Phe
    1385                1390                1395

Phe Phe  Val Asn Ile Phe Val  Ala Leu Ile Ile Ile  Thr Phe Gln
    1400                1405                1410

Glu Gln  Gly Asp Lys Val Met  Ser Glu Cys Ser Leu  Glu Lys Asn
    1415                1420                1425

Glu Arg  Ala Cys Ile Asp Phe  Ala Ile Ser Ala Lys  Pro Leu Thr
    1430                1435                1440

Arg Tyr  Met Pro Gln Asn Lys  Gln Ser Phe Gln Tyr  Lys Thr Trp
    1445                1450                1455

Thr Phe  Val Val Ser Pro Pro  Phe Glu Tyr Phe Ile  Met Ala Met
    1460                1465                1470
```

```
Ile Ala  Leu Asn Thr Val Val  Leu Met Met Lys Phe  Tyr Asp Ala
    1475                 1480                 1485

Pro Tyr  Glu Tyr Glu Leu Met  Leu Lys Cys Leu Asn  Ile Val Phe
    1490                 1495                 1500

Thr Ser  Met Phe Ser Met Glu  Cys Ile Leu Lys Ile  Ile Ala Phe
    1505                 1510                 1515

Gly Val  Leu Asn Tyr Phe Arg  Asp Ala Trp Asn Val  Phe Asp Phe
    1520                 1525                 1530

Val Thr  Val Leu Gly Ser Ile  Thr Asp Ile Leu Val  Thr Glu Ile
    1535                 1540                 1545

Ala Asn  Asn Phe Ile Asn Leu  Ser Phe Leu Arg Leu  Phe Arg Ala
    1550                 1555                 1560

Ala Arg  Leu Ile Lys Leu Leu  Arg Gln Gly Tyr Thr  Ile Arg Ile
    1565                 1570                 1575

Leu Leu  Trp Thr Phe Val Gln  Ser Phe Lys Ala Leu  Pro Tyr Val
    1580                 1585                 1590

Cys Leu  Leu Ile Ala Met Leu  Phe Phe Ile Tyr Ala  Ile Ile Gly
    1595                 1600                 1605

Met Gln  Val Phe Gly Asn Ile  Ala Leu Asp Asp Asp  Thr Ser Ile
    1610                 1615                 1620

Asn Arg  His Asn Asn Phe Arg  Thr Phe Leu Gln Ala  Leu Met Leu
    1625                 1630                 1635

Leu Phe  Arg Ser Ala Thr Gly  Glu Ala Trp His Glu  Ile Met Leu
    1640                 1645                 1650

Ser Cys  Leu Gly Asn Arg Ala  Cys Asp Pro His Ala  Asn Ala Ser
    1655                 1660                 1665

Glu Cys  Gly Ser Asp Phe Ala  Tyr Phe Tyr Phe Val  Ser Phe Ile
    1670                 1675                 1680

Phe Leu  Cys Ser Phe Leu Met  Leu Asn Leu Phe Val  Ala Val Ile
    1685                 1690                 1695

Met Asp  Asn Phe Glu Tyr Leu  Thr Arg Asp Ser Ser  Ile Leu Gly
    1700                 1705                 1710

Pro His  His Leu Asp Glu Phe  Ile Arg Val Trp Ala  Glu Tyr Asp
    1715                 1720                 1725

Pro Ala  Ala Cys Gly Arg Ile  Ser Tyr Asn Asp Met  Phe Glu Met
    1730                 1735                 1740

Leu Lys  His Met Ser Pro Pro  Leu Gly Leu Gly Lys  Lys Cys Pro
    1745                 1750                 1755

Ala Arg  Val Ala Tyr Lys Arg  Leu Val Arg Met Asn  Met Pro Ile
    1760                 1765                 1770

Ser Asn  Glu Asp Met Thr Val  His Phe Thr Ser Thr  Leu Met Ala
    1775                 1780                 1785

Leu Ile  Arg Thr Ala Leu Glu  Ile Lys Leu Ala Pro  Ala Gly Thr
    1790                 1795                 1800

Lys Gln  His Gln Cys Asp Ala  Glu Leu Arg Lys Glu  Ile Ser Ser
    1805                 1810                 1815

Val Trp  Ala Asn Leu Pro Gln  Lys Thr Leu Asp Leu  Leu Val Pro
    1820                 1825                 1830

Pro His  Lys Pro Asp Glu Met  Thr Val Gly Lys Val  Tyr Ala Ala
    1835                 1840                 1845

Leu Met  Ile Phe Asp Phe Tyr  Lys Gln Asn Lys Thr  Thr Arg Asp
    1850                 1855                 1860
```

```
Gln Thr His Gln Ala Pro Gly Gly Leu Ser Gln Met Gly Pro Val
    1865                1870                1875

Ser Leu Phe His Pro Leu Lys Ala Thr Leu Glu Gln Thr Gln Pro
    1880                1885                1890

Ala Val Leu Arg Gly Ala Arg Val Phe Leu Arg Gln Lys Ser Ala
    1895                1900                1905

Thr Ser Leu Ser Asn Gly Gly Ala Ile Gln Thr Gln Glu Ser Gly
    1910                1915                1920

Ile Lys Glu Ser Leu Ser Trp Gly Thr Gln Arg Thr Gln Asp Ala
    1925                1930                1935

Leu Tyr Glu Ala Arg Ala Pro Leu Glu Arg Gly His Ser Ala Glu
    1940                1945                1950

Ile Pro Val Gly Gln Ser Gly Thr Leu Ala Val Asp Val Gln Met
    1955                1960                1965

Gln Asn Met Thr Leu Arg Gly Pro Asp Gly Glu Pro Gln Pro Gly
    1970                1975                1980

Leu Glu Ser Gln Gly Arg Ala Ala Ser Met Pro Arg Leu Ala Ala
    1985                1990                1995

Glu Thr Gln Pro Ala Pro Asn Ala Ser Pro Met Lys Arg Ser Ile
    2000                2005                2010

Ser Thr Leu Ala Pro Arg Pro His Gly Thr Gln Leu Cys Ser Thr
    2015                2020                2025

Val Leu Asp Arg Pro Pro Pro Ser Gln Ala Ser His His His His
    2030                2035                2040

His Arg Cys His Arg Arg Arg Asp Lys Lys Gln Arg Ser Leu Glu
    2045                2050                2055

Lys Gly Pro Ser Leu Ser Val Asp Pro Glu Gly Ala Pro Ser Thr
    2060                2065                2070

Ala Ala Gly Pro Gly Leu Pro His Gly Glu Gly Ser Thr Ala Cys
    2075                2080                2085

Arg Arg Asp Arg Lys Gln Glu Arg Gly Arg Ser Gln Glu Arg Arg
    2090                2095                2100

Gln Pro Ser Ser Ser Ser Ser Glu Lys Gln Arg Phe Tyr Ser Cys
    2105                2110                2115

Asp Arg Phe Gly Ser Arg Glu Pro Pro Gln Leu Met Pro Ser Leu
    2120                2125                2130

Ser Ser His Pro Thr Ser Pro Thr Ala Ala Leu Glu Pro Ala Pro
    2135                2140                2145

His Pro Gln Gly Ser Gly Ser Val Asn Gly Ser Pro Leu Met Ser
    2150                2155                2160

Thr Ser Gly Ala Ser Thr Pro Gly Arg Gly Gly Arg Arg Gln Leu
    2165                2170                2175

Pro Gln Thr Pro Leu Thr Pro Arg Pro Ser Ile Thr Tyr Lys Thr
    2180                2185                2190

Ala Asn Ser Ser Pro Val His Phe Ala Glu Gly Gln Ser Gly Leu
    2195                2200                2205

Pro Ala Phe Ser Pro Gly Arg Leu Ser Arg Gly Leu Ser Glu His
    2210                2215                2220

Asn Ala Leu Leu Gln Lys Glu Pro Leu Ser Gln Pro Leu Ala Pro
    2225                2230                2235

Gly Ser Arg Ile Gly Ser Asp Pro Tyr Leu Gly Gln Arg Leu Asp
    2240                2245                2250

Ser Glu Ala Ser Ala His Thr Leu Pro Glu Asp Thr Leu Thr Phe
```

```
    2255                2260                2265

Glu Glu  Ala Val Ala Thr Asn  Ser Gly Arg Ser Ser  Arg Thr Ser
    2270                2275                2280

Tyr Val  Ser Ser Leu Thr Ser  Gln Ser His Pro Leu  Arg Arg Val
    2285                2290                2295

Pro Asn  Gly Tyr His Cys Thr  Leu Gly Leu Ser Thr  Gly Val Arg
    2300                2305                2310

Ala Arg  His Ser Tyr His His  Pro Asp Gln Asp His  Trp Cys
    2315                2320                2325


<210> SEQ ID NO 10
<211> LENGTH: 2365
<212> TYPE: PRT
<213> ORGANISM: Oncorhynchus mykiss

<400> SEQUENCE: 10

Met Ala Arg Phe Glu Glu Glu Leu Ser Asn Arg Arg Gly Gly Val Cys
1               5                   10                  15

Gln Ala Gly Pro Pro Arg Gly Ala Gly Arg Pro Ala Gly Pro Pro Ser
            20                  25                  30

Gly Pro Arg Val Tyr Lys Gln Ser Met Ala Gln Arg Ala Arg Thr Met
        35                  40                  45

Ala Ile Tyr Asn Pro Ile Pro Val Lys Gln Ser Cys Leu Thr Val Asn
    50                  55                  60

Arg Ser Leu Phe Ile Phe Ser Glu Asp Cys Ile Ile Arg Lys Tyr Ala
65                  70                  75                  80

Lys Lys Ile Thr Glu Trp Pro Pro Phe Glu Tyr Leu Ile Leu Ala Thr
                85                  90                  95

Ile Ile Ala Asn Cys Ile Val Leu Ala Leu Glu Gln His Leu Pro Ala
            100                 105                 110

Ser Asp Lys Thr Pro Met Ser Glu Arg Leu Asp Asp Thr Glu Pro Tyr
        115                 120                 125

Phe Ile Ala Ile Phe Cys Phe Glu Ala Gly Ile Lys Ile Ile Ala Leu
    130                 135                 140

Gly Phe Ala Phe His Lys Gly Ser Tyr Leu Arg Asn Gly Trp Asn Val
145                 150                 155                 160

Met Asp Phe Val Val Val Leu Thr Gly Met Leu Ala Thr Val Gly Ala
                165                 170                 175

Asp Phe Asp Leu Arg Thr Leu Arg Ala Val Arg Val Leu Arg Pro Leu
            180                 185                 190

Lys Leu Val Ser Gly Ile Pro Ser Leu Gln Val Val Leu Lys Ser Ile
        195                 200                 205

Met Lys Ala Met Val Pro Leu Leu Gln Ile Gly Met Leu Leu Phe Phe
    210                 215                 220

Ala Ile Leu Met Phe Ala Ile Ile Gly Leu Asp Phe Tyr Met Gly Lys
225                 230                 235                 240

Phe His Arg Thr Cys Phe Arg Thr Asp Thr Gly Glu Gln Ala Ala Glu
                245                 250                 255

Phe Pro Cys Gly Leu Glu Ala Pro Ala Arg Thr Cys Glu Asn Gly Thr
            260                 265                 270

Val Cys Gln Glu Tyr Trp Ile Gly Pro Thr Tyr Gly Ile Thr Asn Phe
        275                 280                 285

Asp Asn Ile Leu Phe Ala Val Leu Ser Val Phe Gln Cys Ile Thr Met
    290                 295                 300
```

```
Glu Gly Trp Val Asp Ile Leu Tyr Asn Ala Asn Asp Ala Ser Gly Asn
305                 310                 315                 320

Thr Trp Asn Trp Leu Tyr Phe Ile Pro Leu Ile Ile Ile Gly Ser Phe
                325                 330                 335

Phe Met Leu Asn Leu Val Leu Gly Val Leu Ser Gly Glu Phe Ala Lys
            340                 345                 350

Glu Arg Glu Arg Val Glu Lys Arg Gln Asp Phe Leu Lys Leu Arg Arg
        355                 360                 365

Gln Gln Gln Ile Glu Arg Glu Leu Thr Gly Tyr Leu Glu Trp Ile Cys
    370                 375                 380

Lys Ala Glu Glu Val Leu Leu Glu Glu Glu Asp Glu Asn Ala Glu Glu
385                 390                 395                 400

Lys Ser Pro Leu Asp Val Leu Lys Arg Gly Lys Val Lys Lys Ser Lys
                405                 410                 415

Asn Asp Leu Ile Gly Ala Glu Glu Gly Glu Asp His Phe Thr Asp Met
            420                 425                 430

Ser Ser Val Ala Pro Pro Gly Ser Pro Phe Gly Arg Ala Ser Val Lys
        435                 440                 445

Ser Ser Lys Leu Glu Ser Ser Ser Tyr Phe Arg Arg Lys Glu Arg Arg
    450                 455                 460

Met Arg Phe Phe Ile Arg Arg Met Val Lys Ala Gln Ser Phe Tyr Trp
465                 470                 475                 480

Ile Val Leu Cys Leu Val Gly Leu Asn Thr Leu Cys Val Ala Ile Val
                485                 490                 495

His Tyr Asp Gln Pro Glu Trp Leu Thr Thr Gly Leu Tyr Leu Ala Glu
            500                 505                 510

Phe Val Phe Leu Gly Leu Phe Leu Ser Glu Met Ser Leu Lys Met Tyr
        515                 520                 525

Gly Leu Gly Ala Arg Asn Tyr Phe His Ser Ser Phe Asn Cys Phe Asp
    530                 535                 540

Phe Ser Val Ile Ile Gly Ser Ile Leu Glu Val Val Trp Ser Met Ile
545                 550                 555                 560

Lys Pro Gly Ala Ser Tyr Gly Ile Ser Val Leu Arg Ala Leu Arg Leu
                565                 570                 575

Leu Arg Leu Phe Lys Phe Thr Lys Tyr Trp Asn Ser Leu Arg Asn Leu
            580                 585                 590

Val Val Ser Leu Leu Asn Ser Met Lys Ser Ile Ile Ser Leu Leu Phe
        595                 600                 605

Leu Leu Phe Leu Phe Ile Val Val Phe Ala Leu Leu Gly Met Gln Leu
    610                 615                 620

Phe Gly Gly Gln Phe Asn Phe Glu Glu Glu Thr Pro Thr Thr Asn Phe
625                 630                 635                 640

Asp Thr Phe Pro Ala Ala Ile Leu Thr Val Phe Gln Ile Leu Thr Gly
                645                 650                 655

Glu Asp Trp Asn Ala Val Met Tyr His Gly Ile Glu Ser Gln Gly Gly
            660                 665                 670

Val Arg Arg Gly Met Phe Ser Ser Val Tyr Phe Ile Val Leu Thr Leu
        675                 680                 685

Phe Gly Asn Tyr Thr Leu Leu Asn Val Phe Leu Ala Ile Ala Val Asp
    690                 695                 700

Asn Leu Ala Asn Ala Gln Glu Leu Thr Lys Asp Glu Glu Lys Gln Glu
705                 710                 715                 720

Glu Glu Ala Asn Lys Lys Leu Ala Leu Gln Lys Ala Met Glu Val Lys
```

```
                725                 730                 735

Glu Val Ser Pro Val Ser Ala Ala Asn Ile Ser Ile Ala Val Phe Val
            740                 745                 750

Lys Gln Asn Arg Asp Ala Arg Ser Arg Ser Ser Ser Val Ser Ser Val
        755                 760                 765

His Ser Pro Lys Glu Gln Gln Arg Ala Asn Lys Ile Met Ser Val Trp
    770                 775                 780

Glu Gln Arg Thr Asn Gln Leu Arg Gln Asn Asn Leu Arg Ala Ser Ser
785                 790                 795                 800

Glu Ala Leu Phe Asn Glu Leu Asp Pro Glu Glu Arg Leu Arg Val Ser
                805                 810                 815

Ser Ala Leu His Leu Arg Pro Asp Met Lys Thr His Asn Asp Arg Pro
            820                 825                 830

Leu Val Val Glu Pro Gly Asn Gly Asp Asn Pro Arg Pro Pro Glu Glu
        835                 840                 845

Asp Arg Asp Gly Ala Asp Pro Gln Gln Glu Gly Gly Glu Pro His Gly
    850                 855                 860

Pro Gln Pro Arg Lys His Tyr Arg His Arg Glu Arg Asn Gly Glu Ile
865                 870                 875                 880

Gly Glu Ser Arg His His Thr His His Ser Arg Ser Arg Asp His Tyr
                885                 890                 895

His Pro Asp Gly Pro Arg Ser Lys Glu Gly Lys Val Glu Arg Asn His
            900                 905                 910

Ser Arg Glu Gly Gly Gln Gly His Arg His His His Gln Ala Glu Ser
        915                 920                 925

Pro Glu Glu Gly Val Asn Gly Gly Gly Glu Gly Arg Glu Asp Arg His
    930                 935                 940

His His Ser Asp Arg Gln Gly Asn Gly Ala Leu Ala Thr Arg Asp Arg
945                 950                 955                 960

Leu Glu Ser Arg Gly Arg Gly His Arg Glu Glu Asn Gly Glu Arg Arg
                965                 970                 975

Lys His Arg Ser Arg Arg Val Arg Ala Gln Ser Thr Leu Asp Gly Asp
            980                 985                 990

Glu Cys Arg Glu Asn Gly Glu Arg  Asn Gly Asp Gly Asp  Gln Gly His
        995                 1000                1005

Arg Asp  Arg Gln Thr Asp Ser  Gln Gly Glu Ser Leu  Ala Thr Ser
    1010                1015                1020

Pro Val  Gln Pro Pro Ala Gly  Leu Gln Ala Gly Glu  Lys Gln Glu
    1025                1030                1035

Asp Ala  Asp Asn Gln Lys Asn  Ser His Arg Ala Ser  Gln Ala Gly
    1040                1045                1050

Leu Asn  Ser Asn Thr Val His  Ile Pro Val Thr Ile  Thr Ala Pro
    1055                1060                1065

Ser Arg  Glu Thr Thr Ile Ile  Pro Met Asp Asn Ile  Asp Cys Glu
    1070                1075                1080

Ser Leu  Pro Leu Asn Lys Glu  Lys Lys Asp Leu Glu  Glu Glu Leu
    1085                1090                1095

Lys Asn  Gly Pro Lys His Ile  Leu Pro Tyr Ser Ser  Met Phe Val
    1100                1105                1110

Phe Gly  Gln Thr Asn Pro Val  Arg Arg Leu Cys His  Tyr Val Val
    1115                1120                1125

Asn Leu  Arg Tyr Phe Glu Met  Cys Ile Leu Ser Val  Ile Thr Met
    1130                1135                1140
```

```
Ser Ser  Ile Ala Leu Ala Ala  Glu Asp Pro Val Gln  Ala Asn Ala
    1145                 1150                 1155

Pro Arg  Asn Asn Val Leu Lys  Tyr Leu Asp Tyr Val  Phe Thr Gly
    1160                 1165                 1170

Val Phe  Thr Phe Glu Met Val  Ile Lys Met Ile Asp  Leu Gly Leu
    1175                 1180                 1185

Leu Leu  His Pro Gly Ser Tyr  Phe Arg Asp Leu Trp  Asn Ile Leu
    1190                 1195                 1200

Asp Phe  Ile Val Val Ser Gly  Ala Leu Val Ala Phe  Ala Cys Ser
    1205                 1210                 1215

Gly Thr  Lys Gly Lys Asp Ile  Asn Thr Ile Lys Ser  Leu Arg Val
    1220                 1225                 1230

Leu Arg  Val Leu Arg Pro Leu  Lys Thr Ile Lys Arg  Leu Pro Lys
    1235                 1240                 1245

Leu Lys  Ala Val Phe Asp Cys  Val Val Asn Ser Leu  Lys Asn Val
    1250                 1255                 1260

Leu Asn  Ile Leu Ile Val Tyr  Met Leu Phe Met Phe  Ile Phe Ala
    1265                 1270                 1275

Val Ile  Ala Val Gln Leu Phe  Lys Gly Lys Phe Phe  Tyr Cys Thr
    1280                 1285                 1290

Asp Glu  Ser Lys Gly Leu Glu  Lys Asp Cys Arg Gly  Lys Phe Leu
    1295                 1300                 1305

Asp Tyr  Asp Gly Asp Glu Val  Ala Ala Gln Asp Arg  Glu Trp Arg
    1310                 1315                 1320

Lys Tyr  Glu Phe His Tyr Asp  Asn Val Leu Trp Ala  Phe Leu Thr
    1325                 1330                 1335

Leu Phe  Thr Val Ser Thr Gly  Glu Gly Trp Pro Met  Val Leu Lys
    1340                 1345                 1350

His Ser  Val Asp Ala Thr Tyr  Glu Asp Glu Gly Pro  Ser Pro Gly
    1355                 1360                 1365

Phe Arg  Met Glu Thr Ser Ile  Phe Tyr Val Val Tyr  Phe Val Val
    1370                 1375                 1380

Phe Pro  Phe Phe Phe Val Asn  Ile Phe Val Ala Leu  Ile Ile Ile
    1385                 1390                 1395

Thr Phe  Gln Glu Gln Gly Asp  Lys Ala Met Ser Glu  Cys Ser Leu
    1400                 1405                 1410

Glu Lys  Asn Glu Arg Ala Cys  Ile Asp Phe Ala Ile  Asn Ala Lys
    1415                 1420                 1425

Pro Leu  Thr Arg Tyr Met Pro  Ala Asp Lys Gln Ser  Phe Gln Tyr
    1430                 1435                 1440

Lys Met  Trp Gln Phe Val Val  Ser Pro Pro Phe Glu  Tyr Ser Ile
    1445                 1450                 1455

Met Thr  Met Ile Met Thr Met  Ile Ala Leu Asn Thr  Val Val Leu
    1460                 1465                 1470

Met Met  Lys Phe His Gly Ala  Pro Glu Leu Tyr Glu  Ala Met Leu
    1475                 1480                 1485

Lys His  Leu Asn Ile Val Phe  Thr Ala Leu Phe Thr  Leu Glu Cys
    1490                 1495                 1500

Ile Leu  Lys Ile Ile Ala Phe  Gly Pro Leu Asn Tyr  Leu Lys Ala
    1505                 1510                 1515

Ala Trp  Asn Val Phe Asp Phe  Val Thr Val Leu Gly  Ser Ile Thr
    1520                 1525                 1530
```

```
Asp Ile  Leu Val Thr Glu Ile  Lys Thr Asp Lys Leu  Ile Asn Leu
    1535                 1540                 1545

Ser Phe  Leu Arg Leu Phe Arg  Ala Ala Arg Leu Ile  Lys Leu Leu
    1550                 1555                 1560

Arg Gln  Gly Tyr Thr Ile Arg  Ile Leu Leu Trp Thr  Phe Val Gln
    1565                 1570                 1575

Ser Phe  Lys Gly Leu Pro Tyr  Val Cys Leu Leu Ile  Ala Met Leu
    1580                 1585                 1590

Phe Phe  Ile Tyr Ala Ile Ile  Gly Met Gln Val Phe  Gly Asn Ile
    1595                 1600                 1605

Glu Leu  Asn Glu Glu Thr Ala  Ile Asn Pro His Asn  Asn Phe Arg
    1610                 1615                 1620

Thr Phe  Phe Gln Ala Leu Met  Leu Leu Phe Arg Ser  Ala Thr Gly
    1625                 1630                 1635

Glu Ala  Trp His Glu Ile Met  Leu Ser Cys Leu Ser  Asn Arg Pro
    1640                 1645                 1650

Cys Asp  Lys Leu Ser Gly Ser  Gly Gly Lys Glu Cys  Gly Ser Asp
    1655                 1660                 1665

Phe Ala  Tyr Phe Tyr Phe Val  Ser Phe Ile Phe Leu  Cys Ser Phe
    1670                 1675                 1680

Leu Met  Leu Asn Leu Phe Val  Ala Val Ile Met Asp  Asn Phe Glu
    1685                 1690                 1695

Tyr Leu  Thr Arg Asp Ala Ser  Ile Leu Gly Pro His  His Leu Asp
    1700                 1705                 1710

Glu Phe  Ile Arg Val Trp Ala  Glu Tyr Asp Pro Ala  Ala Cys Gly
    1715                 1720                 1725

Arg Met  Thr Tyr Leu Asp Met  Tyr Glu Met Leu Arg  His Met Ser
    1730                 1735                 1740

Pro Pro  Leu Gly Leu Gly Lys  Lys Cys Pro Pro Arg  Ile Ala Tyr
    1745                 1750                 1755

Lys Arg  Leu Val Lys Met Asn  Met Pro Ile Ala Asp  Asp Asn Thr
    1760                 1765                 1770

Val His  Phe Thr Ser Thr Leu  Met Ala Leu Ile Arg  Thr Ala Leu
    1775                 1780                 1785

Glu Ile  Lys Leu Ala Ser Gly  Val Leu Ala Gln Arg  Leu Cys Asp
    1790                 1795                 1800

Ala Asp  Leu Arg Lys Glu Ile  Ser Arg Val Trp Pro  Asn Leu Pro
    1805                 1810                 1815

Gln Lys  Thr Ile Asp Leu Leu  Val Thr Pro Tyr Lys  Asn Asp Glu
    1820                 1825                 1830

Phe Asn  Glu Leu Leu Cys Pro  Phe Ala Val Val Asn  Arg Glu Leu
    1835                 1840                 1845

Thr Val  Gly Lys Val Tyr Ala  Ala Leu Met Ile Phe  Asp Tyr Tyr
    1850                 1855                 1860

Lys Gln  Asn Arg Ala Lys Arg  Leu Glu Gln Gln Leu  Gly Leu Asp
    1865                 1870                 1875

Phe Thr  Gly Thr Ile Lys Asn  Lys Lys Gly Pro Ala  Phe Phe Arg
    1880                 1885                 1890

Pro Met  Met Pro Met Thr His  Met Gln Glu Glu Gly  Thr Thr Val
    1895                 1900                 1905

Ala Gly  Ala Asn Pro Leu Pro  Ser Ser Gln Pro Glu  Pro Glu Ser
    1910                 1915                 1920

Gln Pro  Glu Pro Thr Pro Ser  Thr Thr Ser Leu Thr  Asn Gly Glu
```

```
    1925                1930                1935

Ala Val  Pro Ser Thr Arg Ser  Pro Ile Lys Glu Ser  Gly Glu Gln
    1940                1945                1950

Leu Ser  Gln Glu Gly Gln Arg  Ser Ser Ser Arg Lys  Arg Ile Leu
    1955                1960                1965

Gln Arg  Gly Gln Ser Glu Asp  Val Pro Tyr Ser Asn  Lys Pro Gln
    1970                1975                1980

Glu Ser  Val Glu Met Arg Gln  Val Glu Asn Gly Ala  Asp Ile Gly
    1985                1990                1995

Gly Tyr  Ser Gly Leu Asp Gly  His Gly Arg Ala Ala  Ser Met Pro
    2000                2005                2010

Arg Leu  Asp Ser Gln Tyr Asn  Arg Thr His Pro Arg  His Arg Pro
    2015                2020                2025

Gly Ser  Tyr Leu Ala Pro Ile  Ala Asp Ile Ser Pro  Ile Arg Arg
    2030                2035                2040

Ser Ala  Ser Thr Leu Ala Ser  Gln Cys His Arg Glu  Met Ser Leu
    2045                2050                2055

Arg Val  Tyr Thr Leu Glu Arg  Pro Ser Gln Ala Gln  Ala Ser Ser
    2060                2065                2070

Ala Pro  Gly Gln Ala Gln Asp  Arg Pro His His His  His His His
    2075                2080                2085

Arg Cys  His Arg Arg Arg Asp  Lys Asp Arg Asp Lys  Lys Gln Lys
    2090                2095                2100

Ser Leu  Asp Arg Ala Thr Ser  Val Gln Pro Ser Ser  Thr Ala Cys
    2105                2110                2115

Ser Ser  Val Asp Pro Pro Val  Glu Gly Leu Thr Arg  Ala Arg Glu
    2120                2125                2130

Cys Asp  Arg Gly Arg Pro His  Glu Lys Arg His His  Ser Ala Ala
    2135                2140                2145

Gly Glu  Thr Lys Arg Tyr Tyr  Ser Cys Glu Arg Tyr  Val Gly Arg
    2150                2155                2160

Glu His  Cys His Thr Lys Ser  Ala Gly Pro Ser Arg  Ser Thr Ser
    2165                2170                2175

Pro Gly  Glu Thr His Asp Leu  Gly Leu Leu Lys Gln  Ser Ile Arg
    2180                2185                2190

Met Ser  Lys Gly Ser Gln Val  Val Leu Thr Phe Gly  Ser Ser Pro
    2195                2200                2205

Ser Cys  Arg Gly Arg Arg Gln  Leu Pro Gln Thr Pro  Leu Thr Pro
    2210                2215                2220

Arg Pro  Ala Val Ala Tyr Lys  Thr Gly Asn Ser Leu  Pro Met Gln
    2225                2230                2235

Phe Gly  Ser Thr Gly His Gln  Ser Phe Leu Ser Arg  Gly Leu Ser
    2240                2245                2250

Glu Arg  Asn Ala Leu Leu Glu  Ser Pro Pro Ile Pro  Val Thr Leu
    2255                2260                2265

Ile Gly  Leu Asp Pro Asn Leu  Ser Pro Cys Pro Arg  Asn Pro Pro
    2270                2275                2280

Pro Cys  Arg Leu Ser Glu Glu  Pro Asp Asp Phe Gln  Asp Ala Val
    2285                2290                2295

Ser Asn  His Gly Gly Ser His  Ser Pro Arg Ile Ile  Ala Ser Ala
    2300                2305                2310

Ser His  Gly Ala Ala Gly Pro  Ser Ser Ala Pro Ala  Pro Gln Gly
    2315                2320                2325
```

```
Arg Val  Gly Ile Pro Asn Gly  Tyr His Phe Thr Leu  Gly Val Asn
    2330                 2335                 2340

Ala Val  Ser Ser Ser Ser Pro  Arg Gly Thr Gly Ser  Phe Arg Glu
    2345                 2350                 2355

Lys Glu  Glu Asp Asp Trp Cys
    2360                 2365


<210> SEQ ID NO 11
<211> LENGTH: 2357
<212> TYPE: PRT
<213> ORGANISM: Gallus gallus

<400> SEQUENCE: 11

Met Ala Arg Phe Gly Asp Asp Leu Pro Thr Arg Tyr Gly Gly Gly Gly
1               5                   10                  15

Pro Ala Gly Ala Gly Arg Gly Ser Ser Arg Gln Gly Gly Pro Gln Ala
            20                  25                  30

Gly Gln Arg Met Tyr Lys Gln Ser Met Ala Gln Arg Ala Arg Thr Met
        35                  40                  45

Ala Leu Tyr Asn Pro Ile Pro Val Lys Gln Asn Cys Phe Thr Val Asn
    50                  55                  60

Arg Ser Leu Phe Ile Phe Ser Glu Asp Asn Val Ile Arg Lys Tyr Ala
65                  70                  75                  80

Lys Arg Ile Thr Glu Trp Pro Pro Phe Glu Tyr Met Ile Leu Ala Thr
                85                  90                  95

Ile Ile Ala Asn Cys Ile Val Leu Ala Leu Glu Gln His Leu Pro Asp
            100                 105                 110

Gly Asp Lys Thr Pro Met Ser Glu Arg Leu Asp Asp Thr Glu Pro Tyr
        115                 120                 125

Phe Ile Gly Ile Phe Cys Phe Glu Ala Gly Ile Lys Ile Ile Ala Leu
    130                 135                 140

Gly Phe Val Phe His Lys Gly Ser Tyr Leu Arg Asn Gly Trp Asn Val
145                 150                 155                 160

Met Asp Phe Val Val Val Leu Thr Gly Ile Leu Ala Thr Ala Gly Thr
                165                 170                 175

Asp Phe Asp Leu Arg Thr Leu Arg Ala Val Arg Val Leu Arg Pro Leu
            180                 185                 190

Lys Leu Val Ser Gly Ile Pro Ser Leu Gln Val Val Leu Lys Ser Ile
        195                 200                 205

Met Lys Ala Met Val Pro Leu Leu Gln Ile Gly Leu Leu Leu Phe Phe
    210                 215                 220

Ala Ile Val Met Phe Ala Ile Ile Gly Leu Glu Phe Tyr Met Gly Lys
225                 230                 235                 240

Phe His Lys Thr Cys Phe Ser Asn Lys Thr Gly Glu Glu Val Gly Asp
                245                 250                 255

Phe Pro Cys Gly Glu Glu Pro Pro Ala Arg Gln Cys Glu Ser Gly Thr
            260                 265                 270

Thr Cys Arg Glu Tyr Trp Gln Gly Pro Asn Tyr Gly Ile Thr Asn Phe
        275                 280                 285

Asp Asn Ile Leu Phe Ala Val Leu Thr Val Phe Gln Cys Ile Thr Met
    290                 295                 300

Glu Gly Trp Thr Asp Ile Leu Tyr Asn Thr Asn Asp Ala Ala Gly Asn
305                 310                 315                 320

Thr Trp Asn Trp Leu Tyr Phe Ile Pro Leu Ile Ile Ile Gly Ser Phe
```

```
                325                 330                 335

Phe Met Leu Asn Leu Val Leu Gly Val Leu Ser Gly Glu Phe Ala Lys
            340                 345                 350

Glu Arg Glu Arg Val Glu Asn Arg Arg Ala Phe Leu Lys Leu Arg Arg
        355                 360                 365

Gln Gln Gln Ile Glu Arg Glu Leu Asn Gly Tyr Leu Glu Trp Ile Phe
    370                 375                 380

Lys Ala Glu Glu Val Met Leu Ala Glu Glu Asp Lys Asn Ala Glu Glu
385                 390                 395                 400

Lys Ser Pro Leu Asp Gly Arg Ala Ala Ser Glu Gly Pro Ile Gln Gln
                405                 410                 415

Gly Thr Ala Pro Ala Glu Thr Ser Ser Gly Ser Ser Tyr Asn Met Leu
            420                 425                 430

Lys Arg Ala Ala Ile Lys Lys Ser Lys Asn Asp Leu Ile His Ala Glu
        435                 440                 445

Glu Gly Glu Asp His Phe Thr Asp Ile Cys Ser Val Gly Ser Pro Phe
    450                 455                 460

Ala Arg Ala Ser Leu Lys Ser Gly Lys Asn Glu Ser Ser Ser Tyr Phe
465                 470                 475                 480

Arg Arg Lys Glu Lys Met Phe Arg Phe Phe Ile Arg Arg Met Val Lys
                485                 490                 495

Ala Gln Ser Phe Tyr Trp Ile Val Leu Cys Val Val Ala Leu Asn Thr
            500                 505                 510

Leu Cys Val Ala Met Val His Tyr Asp Gln Pro Glu Lys Leu Thr Thr
        515                 520                 525

Ala Leu Tyr Phe Ala Glu Phe Val Phe Leu Gly Leu Phe Leu Thr Glu
    530                 535                 540

Met Ser Leu Lys Met Tyr Gly Leu Gly Pro Arg Asn Tyr Phe His Ser
545                 550                 555                 560

Ser Phe Asn Tyr Phe Asp Phe Gly Val Ile Val Gly Ser Ile Phe Glu
                565                 570                 575

Val Ile Trp Ala Ala Val Lys Pro Gly Thr Ser Phe Gly Ile Ser Val
            580                 585                 590

Leu Arg Ala Leu Arg Leu Leu Arg Ile Phe Lys Val Thr Lys Tyr Trp
        595                 600                 605

Asn Ser Leu Arg Asn Leu Val Val Ser Leu Leu Asn Ser Met Lys Ser
    610                 615                 620

Ile Ile Ser Leu Leu Phe Leu Leu Phe Leu Phe Ile Val Val Phe Ala
625                 630                 635                 640

Leu Leu Gly Met Gln Leu Phe Gly Gly Gln Phe Asn Phe Arg Asp Glu
                645                 650                 655

Thr Pro Thr Thr Asn Phe Asp Thr Phe Pro Ala Ala Ile Leu Thr Val
            660                 665                 670

Phe Gln Ile Leu Thr Gly Glu Asp Trp Asn Ala Val Met Tyr His Gly
        675                 680                 685

Ile Glu Ser Gln Gly Gly Val His Ser Gly Met Phe Ser Ser Ile Tyr
    690                 695                 700

Phe Ile Val Leu Thr Leu Phe Gly Asn Tyr Thr Leu Leu Asn Val Phe
705                 710                 715                 720

Leu Ala Ile Ala Val Asp Asn Leu Ala Asn Ala Gln Glu Leu Thr Lys
                725                 730                 735

Asp Glu Glu Glu Met Glu Glu Ala Thr Asn Gln Lys Leu Ala Leu Gln
            740                 745                 750
```

```
Lys Ala Lys Glu Val Ala Glu Val Ser Pro Met Ser Ala Ala Asn Ile
      755                 760                 765

Ser Ile Ala Ala Lys Gln Gln Asn Ser Ser Lys Ser Lys Ser Val Trp
    770                 775                 780

Glu Gln Arg Thr Ser Gln Ile Arg Met His Asn Phe Arg Ala Ser Cys
785                 790                 795                 800

Glu Ala Leu Tyr Asn Glu Leu Asp Pro Glu Glu Arg Val Arg Tyr Ala
                805                 810                 815

Thr Thr Leu His Ile Arg Pro Asp Met Lys Thr His Leu Asp Arg Pro
            820                 825                 830

Leu Val Val Glu Pro Arg Gly Glu Gly Arg Asn Asn Ile Ser Lys Leu
        835                 840                 845

Ser Pro Val Asp Val Gln Glu Val Glu Gln Thr Lys Val Ser Ser Thr
    850                 855                 860

Asp Gly Ala Glu Ala Pro Arg Lys His His Arg His Arg Asp Lys Glu
865                 870                 875                 880

Lys Leu Gly Glu Gln Glu Lys Gly Asp Val Thr Lys Asp Glu Asn Gly
                885                 890                 895

Glu Ser Gly Ile Asn Asn Lys Glu Glu Arg His Arg Gln His Arg Ser
            900                 905                 910

Arg Ser Lys Glu Val Glu Gly Gly Ser Lys Glu Gly Lys Ser Asp Arg
        915                 920                 925

Ser Arg Gly Gln Glu Gly Gly Lys Arg His His Arg Arg Gly Ser Val
    930                 935                 940

Glu Glu Gly Val Glu Lys Glu His Arg Arg His Arg Thr His Arg His
945                 950                 955                 960

Ser Ala Glu Arg Gln Gly Lys Glu Gly Asn Gly Thr Ile Asn Gly Ala
                965                 970                 975

Arg Ser Glu Arg Arg Thr Arg His Arg Gly Gly Ser Arg Ser Gly Asn
            980                 985                 990

Arg Glu Gly Glu Pro Gly Ser Lys  Gly Glu Asn Gly Glu  Glu Pro His
        995                 1000                1005

Arg Arg  His Arg Phe Arg Ser  Arg Ala Leu Ser Thr  Tyr Asp Ser
    1010                1015                1020

Val Glu  Lys Glu Asn Arg Glu  Lys Glu Gly Glu Thr  Ala Glu Lys
    1025                1030                1035

Glu His  Gln Asn His Gln Pro  Lys Glu Asn Gln Cys  Glu Ile Glu
    1040                1045                1050

Ala Ser  Gly Ser Val Ser Ile  Pro Val His Thr Leu  Pro Ser Thr
    1055                1060                1065

Tyr Leu  Gln Lys Val Pro Glu  Gln Pro Glu Asp Ala  Asp Asn Gln
    1070                1075                1080

Lys Asn  Val Thr Arg Met Ile  Gln Pro Pro Leu Asp  Lys Thr Thr
    1085                1090                1095

Thr Val  Asn Ile Pro Val Thr  Ile Thr Ala Pro Pro  Gly Glu Thr
    1100                1105                1110

Thr Val  Ile Pro Met Asn Asn  Val Glu Phe Glu Ser  Lys Thr Glu
    1115                1120                1125

Glu Lys  Lys Asp Val Asp Asp  Leu Thr Lys Asn Gly  Pro Lys Pro
    1130                1135                1140

Ile Leu  Pro Tyr Ser Ser Met  Phe Ile Leu Ser Pro  Thr Asn Pro
    1145                1150                1155
```

```
Ile Arg  Arg Leu Phe His Tyr  Ile Val Asn Leu Arg  Tyr Phe Glu
    1160                 1165                 1170

Met Val  Ile Leu Ile Val Ile  Ala Leu Ser Ser Ile  Ala Leu Ala
    1175                 1180                 1185

Ala Glu  Asp Pro Val Gln Ala  Glu Ser Pro Arg Asn  Asp Ala Leu
    1190                 1195                 1200

Lys Tyr  Leu Asp Tyr Ile Phe  Thr Gly Val Phe Thr  Phe Glu Met
    1205                 1210                 1215

Val Ile  Lys Met Ile Asp Leu  Gly Leu Leu Leu His  Pro Gly Ser
    1220                 1225                 1230

Tyr Phe  Arg Asp Leu Trp Asn  Ile Leu Asp Phe Ile  Val Val Ser
    1235                 1240                 1245

Gly Ala  Leu Val Ala Phe Ala  Phe Ser Gly Thr Lys  Gly Lys Asp
    1250                 1255                 1260

Ile Asn  Thr Ile Lys Ser Leu  Arg Val Leu Arg Val  Leu Arg Pro
    1265                 1270                 1275

Leu Lys  Thr Ile Lys Arg Leu  Pro Lys Leu Lys Ala  Val Phe Asp
    1280                 1285                 1290

Cys Val  Val Asn Ser Leu Lys  Asn Val Leu Asn Ile  Leu Ile Val
    1295                 1300                 1305

Tyr Met  Leu Phe Met Phe Ile  Phe Ala Val Ile Ala  Val Gln Leu
    1310                 1315                 1320

Phe Lys  Gly Arg Phe Phe Tyr  Cys Thr Asp Glu Ser  Lys Glu Leu
    1325                 1330                 1335

Glu Lys  Asp Cys Arg Gly Gln  Tyr Leu Asp Tyr Glu  Lys Asn Glu
    1340                 1345                 1350

Val Glu  Ala Gln Pro Arg Glu  Trp Lys Lys Tyr Glu  Phe His Tyr
    1355                 1360                 1365

Asp Asn  Val Leu Trp Ala Leu  Leu Thr Leu Phe Thr  Val Ser Thr
    1370                 1375                 1380

Gly Glu  Gly Trp Pro Thr Val  Leu Lys His Ser Val  Asp Ala Thr
    1385                 1390                 1395

Tyr Glu  Glu Gln Gly Pro Ser  Pro Gly Tyr Arg Met  Glu Met Ser
    1400                 1405                 1410

Ile Phe  Tyr Val Val Tyr Phe  Val Val Phe Pro Phe  Phe Phe Val
    1415                 1420                 1425

Asn Ile  Phe Val Ala Leu Ile  Ile Ile Thr Phe Gln  Glu Gln Gly
    1430                 1435                 1440

Asp Lys  Val Met Ser Glu Cys  Ser Leu Glu Lys Asn  Glu Arg Ala
    1445                 1450                 1455

Cys Ile  Asp Phe Ala Ile Ser  Ala Lys Pro Leu Thr  Arg Tyr Met
    1460                 1465                 1470

Pro Gln  Asn Lys Gln Ser Phe  Gln Tyr Lys Met Trp  Lys Phe Val
    1475                 1480                 1485

Val Ser  Pro Pro Phe Glu Tyr  Phe Ile Met Val Met  Ile Ala Leu
    1490                 1495                 1500

Asn Thr  Ile Val Leu Met Met  Lys Phe Tyr Asp Ala  Pro Glu Ala
    1505                 1510                 1515

Tyr Glu  Glu Met Leu Lys Cys  Leu Asn Ile Val Phe  Thr Ser Met
    1520                 1525                 1530

Phe Ser  Met Glu Cys Val Leu  Lys Ile Ile Ala Phe  Gly Val Leu
    1535                 1540                 1545

Asn Tyr  Phe Arg Asp Ala Trp  Asn Val Phe Asp Phe  Val Thr Val
```

```
    1550                1555                1560

Leu Gly  Ser Ile Thr Asp Ile  Leu Val Thr Glu Ile  Ala Asp Thr
    1565                1570                1575

Asp Asn  Phe Ile Asn Leu Ser  Phe Leu Arg Leu Phe  Arg Ala Ala
    1580                1585                1590

Arg Leu  Ile Lys Leu Leu Arg  Gln Gly Tyr Thr Ile  Arg Ile Leu
    1595                1600                1605

Leu Trp  Thr Phe Val Gln Ser  Phe Lys Ala Leu Pro  Tyr Val Cys
    1610                1615                1620

Leu Leu  Ile Ala Met Leu Phe  Phe Ile Tyr Ala Ile  Ile Gly Met
    1625                1630                1635

Gln Val  Phe Gly Asn Ile Ala  Leu Asn Asp Glu Thr  Ser Ile Asn
    1640                1645                1650

Arg His  Asn Asn Phe Arg Thr  Phe Leu Gln Ala Leu  Met Leu Leu
    1655                1660                1665

Phe Arg  Ser Ala Thr Gly Glu  Ala Trp His Glu Ile  Met Leu Ser
    1670                1675                1680

Cys Leu  Ser Asn Arg Ala Cys  Asp Pro Leu Ser Gly  Leu Thr Lys
    1685                1690                1695

Asn Glu  Cys Gly Ser Asp Phe  Ala Tyr Phe Tyr Phe  Val Ser Phe
    1700                1705                1710

Ile Phe  Leu Cys Ser Phe Leu  Met Leu Asn Leu Phe  Val Ala Val
    1715                1720                1725

Ile Met  Asp Asn Phe Glu Tyr  Leu Thr Arg Asp Ser  Ser Ile Leu
    1730                1735                1740

Gly Pro  His His Leu Asp Glu  Phe Val Arg Val Trp  Ala Glu Tyr
    1745                1750                1755

Asp Pro  Ala Ala Cys Cys Arg  Ile His Tyr Lys Asp  Met Tyr Asn
    1760                1765                1770

Leu Leu  Arg Val Ile Ala Pro  Pro Leu Gly Leu Gly  Lys Lys Cys
    1775                1780                1785

Pro His  Arg Val Ala Tyr Lys  Arg Leu Val Arg Met  Asn Met Pro
    1790                1795                1800

Ile Ser  Pro Glu Asp Leu Thr  Val His Phe Thr Ser  Thr Leu Met
    1805                1810                1815

Ala Leu  Ile Arg Thr Ala Leu  Glu Ile Lys Leu Ala  Ser Gly Gly
    1820                1825                1830

Val Lys  Gln His Gln Cys Asp  Ala Glu Leu Arg Lys  Glu Ile Ser
    1835                1840                1845

Leu Val  Trp Pro Asn Leu Ser  Gln Lys Thr Leu Asp  Leu Leu Val
    1850                1855                1860

Pro Pro  His Lys Pro Asp Glu  Met Thr Val Gly Lys  Val Tyr Ala
    1865                1870                1875

Ala Leu  Met Ile Phe Asp Phe  Tyr Lys Gln Asn Lys  Ser Ser Arg
    1880                1885                1890

Glu Gln  Val His Gln Pro Pro  Gly Gly Leu Cys Gln  Pro Gly Pro
    1895                1900                1905

Val Ser  Leu Phe His Pro Leu  Lys Ala Thr Leu Glu  Gln Thr Gln
    1910                1915                1920

Pro Ser  Ala Phe Ser Ser Ala  Lys Ala Phe Leu Arg  Gln Lys Ser
    1925                1930                1935

Ser Ala  Ser Leu Asn Asn Gly  Gly Thr Leu Pro Ala  Pro Glu Gly
    1940                1945                1950
```

```
Gly Ile Lys Glu Ser Ser Ser Trp Gly Thr Gln Arg Thr Gln Asp
    1955                1960                1965

Val Phe Tyr Glu Thr Arg Thr Pro Ala Phe Glu Arg Gly His Ser
    1970                1975                1980

Glu Glu Ile Pro Ile Glu Arg Val Val Glu Met Arg Glu Ile Ser
    1985                1990                1995

Pro Thr Leu Ala Asn Gly Glu His Gln Pro Gly Leu Glu Ser Gln
    2000                2005                2010

Gly Arg Ala Ala Ser Met Pro Arg Leu Ala Ala Glu Thr Gln Arg
    2015                2020                2025

Ser Lys Ala Arg Ser Pro Gly Ser Tyr Leu Ala Pro Ile Pro Asp
    2030                2035                2040

Thr Ser Pro Met Lys Arg Ser Ile Ser Thr Leu Thr Pro Gln Arg
    2045                2050                2055

Pro His Pro Met His Leu Tyr Glu Tyr Ser Leu Glu Arg Val Pro
    2060                2065                2070

Thr Asp Gln Val His His His His His His Arg Cys His Arg Arg
    2075                2080                2085

Lys Glu Lys Lys Gln Lys Ser Leu Asp Arg Thr Thr His Gln Leu
    2090                2095                2100

Ala Asp Gly Glu Ala Val Ala Gln Ser Gly Glu Ser Ser Ser Lys
    2105                2110                2115

Asp Lys Lys Gln Glu Arg Gly Arg Ser Gln Glu Arg Lys Gln His
    2120                2125                2130

Ser Ser Ser Ser Ser Glu Lys Gln Arg Phe Tyr Ser Cys Asp Arg
    2135                2140                2145

Tyr Gly Ser Arg Asp Arg Ser Gln Pro Lys Ser Ala Asp Gln Ser
    2150                2155                2160

Arg Pro Thr Ser Pro Asn Gly Gly Pro Glu Gln Gly Pro His Arg
    2165                2170                2175

Gln Gly Ser Gly Ser Val Asn Gly Ser Pro Leu Leu Ser Thr Ser
    2180                2185                2190

Gly Ala Ser Thr Pro Cys Arg Gly Arg Arg Gln Leu Pro Gln Thr
    2195                2200                2205

Pro Leu Thr Pro Arg Pro Ser Ile Thr Tyr Lys Thr Ala Asn Ser
    2210                2215                2220

Ser Pro Val His Phe Ser Thr Ser Pro Gly Gly Leu Pro Pro Phe
    2225                2230                2235

Ser Pro Gly Arg Leu Ser Arg Gly Leu Ser Glu His Asn Ala Leu
    2240                2245                2250

Leu Arg Gly Asp Gln Gln Pro Pro Pro Ala Ala Val Ala Arg Ile
    2255                2260                2265

Gly Ser Asp Pro Tyr Leu Gly His Arg Asp Ala Ala Asp Ser Pro
    2270                2275                2280

Ile Gly Ala Ala Pro Glu Asp Thr Leu Thr Phe Glu Glu Ala Val
    2285                2290                2295

Ala Thr Asn Ser Gly Arg Ser Ser Arg Thr Ser Tyr Val Ser Ser
    2300                2305                2310

Leu Thr Ser Gln Ser His Gln Ala Arg Arg Val Pro Asn Gly Tyr
    2315                2320                2325

His Tyr Thr Leu Gly Leu Asn Thr Gly Pro Gly Thr Gly Thr Arg
    2330                2335                2340
```

```
Gly Arg Ser Tyr Tyr His Glu Ala Asp Glu Asp Asp Trp Cys
    2345                2350                2355
```

<210> SEQ ID NO 12
<211> LENGTH: 9783
<212> TYPE: DNA
<213> ORGANISM: Rattus norvegicus

<400> SEQUENCE: 12

```
gggtgcggta gcagctggcg ggcgaggtcc agacagctcg ctgcggctag gttaggagcc     60

cctggcgcgc cgcgccctcg gtgccgggcc gcggagccgg ggatgcgcgc ggcgcccggg    120

agtcatggtc cgcttcgggg acgagctagg cggccgctat gggggcaccg gcggcgggga    180

gcgggctcgg ggcggcgggg ccggcggggc cggtggcccg ggccaggggg gtctgccgcc    240

gggccagcgg gtcctgtaca agcagtccat tgcgcaacgc gcacggacca tggccctgta    300

caaccccatc ccagtcaagc agaactgctt caccgtcaac cgctcgctct tcgtcttcag    360

cgaggacaac gtcgtccgca aatatgctaa gcgcatcacc gaatggccgc ccttcgaata    420

tatgatcctg gccaccatca tcgccaactg tattgtcctg gccctggagc agcacctccc    480

tgatggggac aagactccca tgtctgaacg actggatgac acggaacctt acttcatcgg    540

catcttttgc ttcgaggcgg gcatcaagat catagctctg ggcttcgtgt tccacaaagg    600

ctcctacctc cggaatggct ggaacgtcat ggacttcgtg gtggtcctca cagggattct    660

tgccacagct ggaactgact ttgatctgcg caccctgagg gctgtgcgtg tgcttaggcc    720

cctgaagttg gtgtctggaa ttccaagctt gcaggtggtg ctcaagtcca tcatgaaggc    780

catggtcccg ctgctgcaga tcgggctgct gctcttcttc gccatcctca tgttcgctat    840

catcggcctc gagttctata tgggcaaatt ccataaggcc tgcttcccca acagcacaga    900

tgcagagcct gtgggtgact ttccttgtgg caaggaggcc cctgctcgtc tgtgtgacag    960

tgacaccgaa tgccgggagt actggccagg acccaacttt ggcatcacca attttgacaa   1020

catcctgttt gccatcttga ccgtgttcca gtgtatcacc atggagggct ggactgacat   1080

cctctacaat acaaatgatg cggccggcaa cacgtggaac tggttgtact tcatccccct   1140

catcatcatt ggctccttct tcatgctcaa cctggtgctc ggtgtgcttt caggagagtt   1200

tgccaaagag cgggagcgag tcgagaaccg ccgtgccttc ctgaagctcc gcaggcagca   1260

gcagattgag cgagaactga atgggtactt ggagtggatc ttcaaggcgg aggaagtcat   1320

gttggcagag gaggacaaga acgcagaaga gaagtcccct ttggatgcag tgttgaagag   1380

agctgctacc aagaagagcc gaaatgacct catccatgca gaagaggggg aggaccggtt   1440

tgtagacctc tgtgctgctg ggtctccctt tgctcgtgcc agcctcaaga gtgggaagac   1500

agagagctca tcgtacttcc ggaggaagga gaagatgttc cggttcctta tccgtcgtat   1560

ggtgaaagca cagagcttct actgggtggt actgtgcgtg gtggccctga acacgttgtg   1620

tgtggccatg gtacactata atcagcctca gcggcttacc actgcactgt actttgcaga   1680

gtttgttttc ctgggtctct tcctcacaga gatgtccctg aagatgtacg gtctagggcc   1740

cagaagctac ttccggtctt ccttcaactg ctttgacttt ggggtgattg tggggagtat   1800

ctttgaagta gtctgggctg ccatcaagcc aggaacctcc ttcggaatca gtgtgctgcg   1860

ggctctccga ctgctgagga ttttcaaagt caccaagtat tggaactccc tgaggaacct   1920

ggttgtttcc ctcctcaact ccatgaagtc catcatcagc cttctcttcc tgcttttcct   1980

tttcattgtg gtcttcgctc tgttggggat gcagctgttt gggggacagt tcaactttca   2040
```

```
agatgagact ccaaccacca attttgatac cttcccagct gccatcctca ctgtgtttca   2100
gattctgaca ggagaggact ggaatgcagt catgtatcat gggattgagt cacaaggagg   2160
agtcagcaaa ggcatgtttt catcctttta cttcatcgtc ctgacactgt ttggaaacta   2220
caccctgttg aacgttttct tggccattgc tgtggacaac cttgccaatg cccaggagtt   2280
gaccaaggat gaagaggaga tggaagaggc agccaatcag aagcttgctc ttcagaaggc   2340
caaagaagta gctgaagtca gccccatgtc tgctgccaac atctccattg ctgcttttgt   2400
aaagcaaact cgaggtactg tatctcgcag ctcatctgtc tccagcgtaa actcaccgca   2460
gcagaactcg gccaaggcgc gctcagtatg ggagcagcgg gccagtcagc taaggctcca   2520
gaacctgcgt gccagctgtg aggcactgta cagtgagatg gacccggagg agcgcctgcg   2580
ttatgccagc acgcgccacg tgaggccaga catgaagaca cacatggacc gacccctagt   2640
ggtggaacct ggtcgggatg gcctgcgggg acccgccggg aacaagtcaa agcctgaggg   2700
cacggaggcc accgaaggtg cggatccacc acgccgacac caccggcatc gtgataggga   2760
caagacctca gcctcaaccc ctgctggagg cgaacaggac aggacagact gcccaaaggc   2820
cgaaagcacc gagaccgggg cccgggagga acgtgcgcgc cctcgtcgaa gtcacagcaa   2880
ggaggctcca ggggctgaca cacaagtgcg ttgtgagcgc agtagacgtc accaccggcg   2940
cggatccccg gaggaggcca ctgaacggga acctcggcgc caccgtgccc accggcacgc   3000
acaggactca agcaaggaag gcaaggaggg cactgcaccg gtgcttgtac ccaagggcga   3060
gcgtcgcgca agacatcgag gcccgcgtac gggcccccgt gagacagaga acagtgagga   3120
gcccacacgc aggcaccgtg caaagcataa ggtgccacca acacttgagc cccagagag    3180
ggaggttgca gagaaggaga gcaacgtggt ggaaggggat aaggaaactc gaaatcacca   3240
gcccaaggaa cctcgctgtg acctggaggc cattgcggtt acaggcgtgg gctctctgca   3300
catgctgccc agcacctgtc tccagaaagt ggacgaacag ccagaggatg cagacaacca   3360
gcgtaatgtc acccggatgg gcagtcagcc ctcagacccc agcaccactg tgcatgtccc   3420
agtgacactg acaggccctc ccggggaggc cactgtagtt cccagtgcta acacggacct   3480
ggaaggccaa gcggagggca agaaggaggc agaggctgac gatgtgctga gaagaggccc   3540
caggcccatc gttccctaca gttccatgtt ctgcctcagc cccaccaacc tactccgtcg   3600
cttctgccat tacattgtga ccatgcggta ctttgagatg gtgattcttg tggtcatcgc   3660
cttgagcagc attgccctgg ctgctgagga tcccgtgcgg accgactcat tccggaacaa   3720
tgctctgaag tacatggact acatctttac aggagtcttc acctttgaga tggtcataaa   3780
gatgatagac ttgggcctgc tgctgcaccc tggggcctac ttccgggacc tgtggaacat   3840
tctggacttc attgttgtca gtggagccct ggtggcattt gcattctcag gatccaaagg   3900
gaaagacatc aataccatca agtctctgag agtcctgcga gtcctgcggc ccctcaagac   3960
catcaagcgg ctgcctaaac tcaaggctgt gtttgactgt gtggtgaact ctctgaagaa   4020
tgtcttgaac atcctgatcg tctacatgct cttcatgttt atatttgccg tcatcgccgt   4080
ccaactcttc aaagggaagt tcttttactg cactgatgag tccaaggagc tggagcggga   4140
ctgcaggggt cagtatttgg attatgagaa ggaagaggta gaagcccagc caaggcagtg   4200
gaagaaatat gacttccact atgacaatgt gctctgggcc ttgctgactc tgtttacggt   4260
gtccacagga gaggggtggc ccatggtgct gaaacactct gtggacgcca cctatgagga   4320
gcaggggcca agccccgggt ttcggatgga gctttccatc ttctatgtgg tctactttgt   4380
ggtcttccct tttttctttg tcaacatctt tgtggccttg atcatcatca ccttccagga   4440
```

```
gcagggggac aaggtgatgt ctgagtgcag tctggaaaag aatgagaggg cttgcattga   4500
ctttgccatc agcgccaaac ccctgacacg gtacatgcct cagaacaagc agtcgttcca   4560
gtataagaca tggacatttg tggtctctcc accctttgag tacttcatta tggccatgat   4620
agccctcaac acagtggtgc tgatgatgaa gttctacgat gccccttatg agtacgagct   4680
gatgctgaag tgcttgaaca tcgtcttcac atccatgttc tctctggagt gcatcctgaa   4740
gatcatcgcc ttcggggtgt tgaactactt cagagatgcc tggaacgtct ttgactttgt   4800
cactgttttg ggaagtatta ctgatatttt agtaacggag attgcggaaa cgaacaactt   4860
catcaacttg agcttccttc gcctcttccg ggcagcacgg ctgatcaagc tgcttcgcca   4920
gggctacacc atccgcatct tgttatggac ctttgtccag tcctttaagg cgctgcccta   4980
cgtgtgcctc ctcattgcca tgctgttctt catctacgcc atcatcggca tgcaggtttt   5040
tggaaacatt gcccttgatg atggcaccag catcaaccga cacaacaact tccggacatt   5100
tctgcaagcc ttaatgctgt tgttcaggag tgccactggg gaggcctggc acgaaatcat   5160
gctgtcttgc ctgggcaacc gggcctgcga cccacatgcc aacgccagcg aatgcgggag   5220
cgactttgcc tatttttatt ttgtctcctt catcttcctc tgttcctttc tgatgctgaa   5280
cctctttgtt gctgtgatca tggacaattt cgaatacctc acgcgggatt cttccatcct   5340
agggccgcac cacctcgatg aattcattcg cgtctgggct gaatacgacc cagctgcgtg   5400
tgggcgcatc agttacaatg acatgtttga gatgctgaaa cacatgtccc cacctctggg   5460
tttggggaag aaatgcccgg ctcgagttgc atacaagcgc ctggttcgaa tgaacatgcc   5520
catatccaat gaggacatga cggtacactt tacatccaca ctgatggccc tcatccggac   5580
ggcactggag atcaagcttg ccccagcggg gacaaaacag caccaatgtg atgctgagct   5640
gaggaaggag atctcttctg tgtgggctaa tctgccccag aagactctgg acttactggt   5700
gccaccccac aaacctgacg agatgacagt ggggaaggtc tatgcggctc tcatgatatt   5760
tgacttctac aaacagaaca aaaccaccag agatcagact caccaagctc ctggaggcct   5820
gtcccagatg ggtcctgttt ccctgttcca tcctctgaag gccaccctgg agcagacaca   5880
gcccgctgtg ctccgaggag ctcgggtttt ccttcgacaa aagagtgcaa cttccctcag   5940
caatgggggc gccatacaaa cccaggaaag tggcatcaag gagtccctgt cctggggcac   6000
gcagaggacc caggacgtac tttatgaggc cagagcacct ctagaacgtg gccattctgc   6060
agagatccct gtggggcagc caggagcact ggctgtagat gtccagatgc agaacatgac   6120
attgagagga ccggatgggg agccccagcc tggcctggag agccaaggcc gagcggcctc   6180
tatgccacgc ctggcggcag aaacacagcc ggcccctaat gccagcccca tgaagcgctc   6240
catctccaca ctggctccac gcccgcatgg gactcagctt tgcaacacag tcctggaccg   6300
gccacctcct agccaggtgt cccatcacca ccaccaccgc tgccaccggc gcagggacaa   6360
gaagcagagg tccctggaaa aggggcccag cctgtctgtt gacacagaag gtgcaccaag   6420
tactgctgca ggatctggcc tgccccatgg agaagggtcc acaggctgcc ggcgggagcg   6480
taagcaagag cgaggccggt cccaggagcg gaggcagccc tcctcctctt cttcagagaa   6540
gcagcgcttc tattcctgtg accgctttgg gagccgggag cccccacaac ctaagccctc   6600
cctcagtagc caccccatat cgccaacagc ggcactagag ccaggacccc acccgcaggg   6660
cagtggttcc gttaatggga gcccettgat gtcaacatct ggtgctagca cgccgggccg   6720
aggtgggcgg aggcagctcc cccagactcc cctgacccca cgccccagca tcacctacaa   6780
```

```
gacggccaat tcctcgcctg tccactttgc tgagggtcag agtggccttc cagccttctc   6840
ccctggccgt ctcagccgcg gcctttctga acacaatgcc ctgctccaga aagagcccct   6900
gagccagcct ctagcttctg gctcccgcat tggctctgac ccttacctag ggcagcgtct   6960
ggacagtgag gcctctgccc acaacctgcc tgaggataca ctcacctttg aagaggccgt   7020
ggccaccaac tctggccgct cctccaggac ttcctatgtg tcctccctca cttcccaatc   7080
ccaccctctc cgccgtgtac ccaatggcta ccactgcact ttgggactca gcaccggcgt   7140
ccgggcgcgg cacagctacc accacccaga ccaggatcac tggtgctagc tgcaccacga   7200
ccacccatgc accagctcgt gggtgcgggt tccagttgat gagttttatc atccgctctg   7260
ggttgtgcgg tcacagccct gggaggaggg tcctcacatc gcggcctctg tggtggaggt   7320
tcctgcttct ctccctccct cccttttaca ctggacagac taataaagcc ctttcttaga   7380
gggatatggt cctctctatc ctcctgtgta ctgccttcct gggttccatg ccagatgttg   7440
gatcctaagc agaggtagct gagttgagat agacccagca aatccaaatc ctatgtcatg   7500
gcctccagct tccagggtgg gtacttggga ctttcttagg aggtctgagc ctcatggaga   7560
ttgtggtttg tccaaatgtg tggcatgggg gatagggtac cctcaaaggc aaggaaagga   7620
gcccaactgt gtggcctggc agcacctgcc agcatcacta ctctcatgtc tattgtggtc   7680
ttggagtcaa atagcacatg tatatagaga tatgctcaag ggcctgcctt tcacctacat   7740
tgtcaccata atagggacca aatctagagg atgtccttgc tgttgattct ggttttcagt   7800
cacaacactt tcactttttg tcatttctat atagttgatc tagaaaaaca gaaatcaaaa   7860
cagggaagaa aatgttcgtg taacttaaaa aagaaatcaa cgtgtaggaa ggtctccatt   7920
ttgcattgtt tctgtgactt gtatgcaatg ttcctgtatg tattctaccc ttcccgggaa   7980
gtccccaatg accctggttc ctctgctcaa ccaagtgcct gatctctggc tctgagcatc   8040
gtggctgagg tgcggcctca ggaagcatcg gggagctgct cagagcagca ctaggacttg   8100
tgtcttaggg acactgaccg tgtccagcag catgtcagag aagcagctgt agtgcccatg   8160
ttcctccctg agtgatgggt tctgaagaag ccagagcagc acaatgtgtg cttgcgtgag   8220
gcactttccg ccttttaaaa tctgattctc agggatggga tgcctgccaa gtagggtgtg   8280
atctctgttg tgttttaaaa aacaacaaca acaaacaaac aaaacctagt attcactgaa   8340
tgctgaagag agcaaaatgc aagcaaagaa gggactgggg ttagagggag aagcccgcac   8400
tggcagcata ataagaaact ggcagggagg ggatggtcct ggaacaggcc aggtgcctag   8460
agctgagtcc agcccctggc ccggaactgg ggacacagca ctcaaataaa acctcatggc   8520
tacttggtga aggcaaaccc atgctcagga aggtgttcag tgtgcagaga tggctgtgag   8580
gccatgagag aaaggtttca cataggcagg cagtccttgg tgtgttctct gtgttttgaa   8640
acgtctgatg acttcttggt ggactgttgg tttctacccc atgtttctca cagaagctgt   8700
gtatatgtgt gattgcgcgt gtgattgcat gtgtgtggta gtgtgcgtgc gtgagcatgc   8760
atgagtcata ggaaatgtgt gtgtgtgtgt gtgtgtgtgt gtaggtgtgt gtacgtgtgt   8820
tcagcaagtg gcttttgtca accatagggc tatgcaacaa aagacacatt actagaaaca   8880
aaacacaaga ccaccactcg gtctagggtt tcagcatgat tgtgaccaaa ccttttatag   8940
aatttcctta tatgaaggca caataccctg aaactttaaa gataacagag tattttattc   9000
cagtagggta agattaaaca ggaccctgga ctgcatgtga ctgcactcat gtacaacaga   9060
ggaggatgtg cattttgata ctgttctgtc tctgtcccag ccccagccct tttctcttga   9120
gtgttgaatg tatacattct gtgtggaact acagctgctc cagacagtcc tgggttggga   9180
```

-continued

```
atcatcttta tcccacatta acatagctgg cttttcttcc aagcactggt acacaggaaa   9240

ggagacatga tgtcttgctt cctgactttg ggtttgtttc tgtactgtct cttctcaaga   9300

tgttgtctgt tccccctgaa atttcatagt gagttgccaa atttgaaatg caacaaccag   9360

ctgtctgcat ctggaacctg tcaagcagtg ctgtagtttg aaaaagttat gtgtgcatgt   9420

aaaatataca catatatata tatacattat acaagtatgt gcatgaaatg tatatcttca   9480

tactttttga tacaatgtat tcatttgtta atttttaatt atatttgata taaattgaag   9540

gtttgttgca aaaatttata tttaacagtg ttgagagaga gagaaagagc gagagaggga   9600

gagagagaga aagatccaat catgcaacag aaatgggact actttaaaaa tcagtccttt   9660

gactagtttg ctgcctgaat aatatttaca aaccaaactt tggattctgc tcttgtttct   9720

acaatgactt tttgtataaa gcaaagtcct tggattaaat aaaaacaacc aaaaaaatca   9780

aaa                                                                 9783
```